US008317858B2

(12) United States Patent
Straubinger et al.

(10) Patent No.: US 8,317,858 B2
(45) Date of Patent: Nov. 27, 2012

(54) STENT FOR THE POSITIONING AND ANCHORING OF A VALVULAR PROSTHESIS IN AN IMPLANTATION SITE IN THE HEART OF A PATIENT

(75) Inventors: Helmut Straubinger, Aschheim (DE); Johannes Jung, Karlsruhe (DE)

(73) Assignee: JenaValve Technology, Inc., Wilmington, DE (US)

( * ) Notice: Subject to any disclaimer, the term of this patent is extended or adjusted under 35 U.S.C. 154(b) by 256 days.

(21) Appl. No.: 12/392,467

(22) Filed: Feb. 25, 2009

(65) Prior Publication Data
US 2009/0216312 A1 Aug. 27, 2009

Related U.S. Application Data

(63) Continuation-in-part of application No. 12/285,544, filed on Oct. 8, 2008, which is a continuation-in-part of application No. 12/071,814, filed on Feb. 26, 2008.

(51) Int. Cl.
*A61F 2/24* (2006.01)
*A61F 2/82* (2006.01)
(52) U.S. Cl. ............... 623/2.12; 623/1.26; 623/1.15
(58) Field of Classification Search ............ 623/1.24, 623/2.11–2.18, 1.15, 1.26; *A61F 2/24*
See application file for complete search history.

(56) References Cited

U.S. PATENT DOCUMENTS

| 4,922,905 | A | 5/1990 | Strecker |
| 5,002,566 | A | 3/1991 | Carpentier et al. |
| 5,061,277 | A | 10/1991 | Carpentier et al. |
| B15061277 | I5 | 10/1991 | Carpentier et al. |
| 5,094,661 | A | 3/1992 | Levy et al. |
| 5,104,407 | A | 4/1992 | Lam et al. |
| B15104407 | I5 | 4/1992 | Lam et al. |

(Continued)

FOREIGN PATENT DOCUMENTS

| AU | 2006310681 A1 | 5/2007 |
| CA | 2436258 A1 | 1/2005 |
| CA | 2595233 | 7/2006 |
| CA | 2627555 | 5/2007 |

(Continued)

OTHER PUBLICATIONS

Aortenklappenbioprothese erfolgreich in der Entwicklung, (1 page) May 16, 2003.

(Continued)

*Primary Examiner* — Thomas J Sweet
*Assistant Examiner* — Jason-Dennis Stewart
(74) *Attorney, Agent, or Firm* — Bookoff McAndrews, PLLC

(57) ABSTRACT

The present invention relates to a stent for the positioning and anchoring of a valvular prosthesis in an implantation site in the heart of a patient. Specifically, the present invention relates to an expandable stent for an endoprosthesis used in the treatment of a narrowing of a cardiac valve and/or a cardiac valve insufficiency. So as to ensure that no longitudinal displacement of a valvular prosthesis fastened to a stent will occur relative the stent in the implanted state of the stent, even given the peristaltic motion of the heart, the stent according to the invention comprises at least one fastening portion via which the valvular prosthesis is connectable to the stent. The stent further comprises positioning arches and retaining arches, whereby at least one positioning arch is connected to at least one retaining arch via a first connecting web. The stent moreover comprises at least one auxiliary retaining arch which connects the respective arms of the at least one retaining arch connected to the at least one positioning arch.

20 Claims, 36 Drawing Sheets

U.S. PATENT DOCUMENTS

| | | |
|---|---|---|
| 5,197,979 A | 3/1993 | Quintero et al. |
| 5,279,612 A | 1/1994 | Eberhardt |
| 5,332,402 A | 7/1994 | Teitelbaum |
| 5,336,258 A | 8/1994 | Quintero et al. |
| 5,352,240 A | 10/1994 | Ross |
| 5,368,608 A | 11/1994 | Levy et al. |
| 5,411,552 A | 5/1995 | Andersen et al. |
| 5,456,713 A | 10/1995 | Chuter |
| 5,509,930 A | 4/1996 | Love |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,876,434 A | 3/1999 | Flomenblit et al. |
| 5,880,242 A | 3/1999 | Hu et al. |
| 5,899,936 A | 5/1999 | Goldstein |
| 5,928,281 A | 7/1999 | Huynh et al. |
| 5,935,163 A | 8/1999 | Gabbay |
| 6,001,126 A | 12/1999 | Nguyen-Thien-Nhon |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,254,564 B1 | 7/2001 | Wilk et al. |
| 6,254,636 B1 | 7/2001 | Peredo |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,137,184 B2 | 11/2006 | Schreck et al. |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 7,896,915 B2 | 3/2011 | Guyenot et al. |
| 7,914,575 B2 | 3/2011 | Guyenot et al. |
| 2001/0011187 A1 | 8/2001 | Pavcnik et al. |
| 2001/0039450 A1 | 11/2001 | Pavcnik et al. |
| 2002/0032481 A1 | 3/2002 | Gabbay |
| 2002/0055775 A1 | 5/2002 | Carpentier et al. |
| 2002/0123790 A1 | 9/2002 | White et al. |
| 2002/0133226 A1 | 9/2002 | Marquez et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0153974 A1 | 8/2003 | Spenser et al. |
| 2003/0195620 A1 | 10/2003 | Huynh et al. |
| 2003/0236570 A1 | 12/2003 | Cook et al. |
| 2004/0006380 A1 | 1/2004 | Buck et al. |
| 2004/0039436 A1 | 2/2004 | Spenser et al. |
| 2004/0049262 A1 | 3/2004 | Obermiller et al. |
| 2004/0073289 A1 | 4/2004 | Hartley et al. |
| 2004/0078950 A1 | 4/2004 | Schreck et al. |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0210301 A1 | 10/2004 | Obermiller et al. |
| 2004/0210304 A1 | 10/2004 | Seguin et al. |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075725 A1 | 4/2005 | Rowe |
| 2005/0075776 A1 | 4/2005 | Cho |
| 2005/0096726 A1 | 5/2005 | Sequin et al. |
| 2005/0096735 A1* | 5/2005 | Hojeibane et al. ........... 623/1.24 |
| 2005/0096736 A1 | 5/2005 | Osse et al. |

| | | | |
|---|---|---|---|
| 2005/0098547 A1 | 5/2005 | Cali et al. | |
| 2005/0113910 A1 | 5/2005 | Paniagua et al. | |
| 2005/0119728 A1 | 6/2005 | Sarac | |
| 2005/0119736 A1 | 6/2005 | Zilla et al. | |
| 2005/0137687 A1 | 6/2005 | Salahieh et al. | |
| 2005/0137688 A1 | 6/2005 | Salahieh et al. | |
| 2005/0137690 A1 | 6/2005 | Salahieh et al. | |
| 2005/0137697 A1 | 6/2005 | Salahieh et al. | |
| 2005/0137698 A1* | 6/2005 | Salahieh et al. | 623/2.11 |
| 2005/0137702 A1 | 6/2005 | Haug et al. | |
| 2005/0143804 A1 | 6/2005 | Haverkost | |
| 2005/0143807 A1 | 6/2005 | Pavcnik et al. | |
| 2005/0149166 A1 | 7/2005 | Schaeffer et al. | |
| 2005/0150775 A1 | 7/2005 | Zhang et al. | |
| 2005/0171597 A1 | 8/2005 | Boatman et al. | |
| 2005/0171598 A1 | 8/2005 | Schaeffer | |
| 2005/0192665 A1 | 9/2005 | Spenser et al. | |
| 2005/0197695 A1 | 9/2005 | Stacchino et al. | |
| 2005/0222668 A1 | 10/2005 | Schaeffer et al. | |
| 2005/0234546 A1 | 10/2005 | Nugent et al. | |
| 2005/0267560 A1 | 12/2005 | Bates | |
| 2006/0009842 A1 | 1/2006 | Huynh et al. | |
| 2006/0025857 A1 | 2/2006 | Bergheim et al. | |
| 2006/0047343 A1 | 3/2006 | Oviatt et al. | |
| 2006/0058864 A1 | 3/2006 | Schaeffer et al. | |
| 2006/0074484 A1 | 4/2006 | Huber | |
| 2006/0111770 A1 | 5/2006 | Pavcnik et al. | |
| 2006/0142846 A1 | 6/2006 | Pavcnik et al. | |
| 2006/0149360 A1 | 7/2006 | Schwammenthal et al. | |
| 2006/0155366 A1 | 7/2006 | LaDuca et al. | |
| 2006/0167543 A1 | 7/2006 | Bailey et al. | |
| 2006/0178740 A1* | 8/2006 | Stacchino et al. | 623/2.18 |
| 2006/0193885 A1 | 8/2006 | Neethling et al. | |
| 2006/0210597 A1 | 9/2006 | Hiles | |
| 2006/0224183 A1 | 10/2006 | Freudenthal | |
| 2006/0229718 A1 | 10/2006 | Marquez | |
| 2006/0229719 A1 | 10/2006 | Marquez et al. | |
| 2006/0246584 A1 | 11/2006 | Covelli | |
| 2006/0259134 A1 | 11/2006 | Schwammenthal et al. | |
| 2006/0259136 A1 | 11/2006 | Nguyen et al. | |
| 2006/0259137 A1 | 11/2006 | Artof et al. | |
| 2006/0265056 A1 | 11/2006 | Nguyen et al. | |
| 2006/0287717 A1 | 12/2006 | Rowe et al. | |
| 2006/0287719 A1 | 12/2006 | Rowe et al. | |
| 2006/0290027 A1 | 12/2006 | O'Connor et al. | |
| 2006/0293745 A1 | 12/2006 | Carpentier et al. | |
| 2007/0005129 A1 | 1/2007 | Damm et al. | |
| 2007/0005131 A1 | 1/2007 | Taylor | |
| 2007/0005132 A1 | 1/2007 | Simionescu et al. | |
| 2007/0010876 A1* | 1/2007 | Salahieh et al. | 623/2.11 |
| 2007/0020248 A1 | 1/2007 | Everaerts et al. | |
| 2007/0021826 A1 | 1/2007 | Case et al. | |
| 2007/0027535 A1 | 2/2007 | Purdy, Jr. et al. | |
| 2007/0038291 A1 | 2/2007 | Case et al. | |
| 2007/0038295 A1 | 2/2007 | Case et al. | |
| 2007/0043435 A1 | 2/2007 | Seguin et al. | |
| 2007/0050014 A1 | 3/2007 | Johnson | |
| 2007/0088431 A1 | 4/2007 | Bourang et al. | |
| 2007/0093887 A1 | 4/2007 | Case et al. | |
| 2007/0100435 A1 | 5/2007 | Case et al. | |
| 2007/0100440 A1 | 5/2007 | Figulla et al. | |
| 2007/0112422 A1 | 5/2007 | Dehdashtian | |
| 2007/0123700 A1 | 5/2007 | Ueda et al. | |
| 2007/0123979 A1 | 5/2007 | Perier et al. | |
| 2007/0142906 A1 | 6/2007 | Figulla et al. | |
| 2007/0162103 A1 | 7/2007 | Case et al. | |
| 2007/0173932 A1 | 7/2007 | Cali et al. | |
| 2007/0179592 A1 | 8/2007 | Schaeffer | |
| 2007/0185565 A1 | 8/2007 | Schwammenthal et al. | |
| 2007/0203576 A1 | 8/2007 | Lee et al. | |
| 2007/0213813 A1 | 9/2007 | Von Segesser et al. | |
| 2007/0239271 A1 | 10/2007 | Nguyen | |
| 2007/0244551 A1 | 10/2007 | Stobie | |
| 2007/0260327 A1 | 11/2007 | Case et al. | |
| 2007/0288087 A1 | 12/2007 | Fearnot et al. | |
| 2008/0004688 A1 | 1/2008 | Spenser et al. | |
| 2008/0021546 A1 | 1/2008 | Patz et al. | |
| 2008/0033534 A1 | 2/2008 | Cook et al. | |
| 2008/0065011 A1 | 3/2008 | Marchand et al. | |
| 2008/0071361 A1 | 3/2008 | Tuval et al. | |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0071368 A1* | 3/2008 | Tuval et al. | 623/2.17 |
| 2008/0071369 A1 | 3/2008 | Tuval et al. | |
| 2008/0077236 A1 | 3/2008 | Letac et al. | |
| 2008/0086205 A1 | 4/2008 | Gordy et al. | |
| 2008/0097586 A1 | 4/2008 | Pavcnik et al. | |
| 2008/0102439 A1 | 5/2008 | Tian et al. | |
| 2008/0133003 A1 | 6/2008 | Seguin et al. | |
| 2008/0140189 A1 | 6/2008 | Nguyen et al. | |
| 2008/0154355 A1 | 6/2008 | Benichou et al. | |
| 2008/0200977 A1 | 8/2008 | Paul et al. | |
| 2008/0215143 A1 | 9/2008 | Seguin | |
| 2008/0255661 A1 | 10/2008 | Straubinger et al. | |
| 2008/0262602 A1 | 10/2008 | Wilk et al. | |
| 2008/0269878 A1 | 10/2008 | Iobbi | |
| 2008/0275549 A1 | 11/2008 | Rowe | |
| 2009/0222076 A1 | 9/2009 | Figulla et al. | |
| 2010/0249915 A1 | 9/2010 | Zhang | |
| 2010/0249916 A1 | 9/2010 | Zhang | |
| 2010/0249917 A1 | 9/2010 | Zhang | |
| 2010/0249918 A1 | 9/2010 | Zhang | |

FOREIGN PATENT DOCUMENTS

| | | |
|---|---|---|
| DE | 19546692 A1 | 6/1997 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 101 21 210 A1 | 11/2002 |
| DE | 19546692 C2 | 11/2002 |
| DE | 10301026 A1 | 2/2004 |
| DE | 10335948 B3 | 7/2004 |
| DE | 10302447 A1 | 2/2005 |
| DE | 10010074 B4 | 4/2005 |
| DE | 19857887 B4 | 5/2005 |
| DE | 10010073 B4 | 12/2005 |
| DE | 10 2005 051 849 | 5/2007 |
| DE | 10 2005 052628 A1 | 5/2007 |
| DE | 202007005491 U1 | 7/2007 |
| EP | 0084395 A1 | 7/1983 |
| EP | 0458877 | 8/1990 |
| EP | 0402036 B1 | 12/1990 |
| EP | 0402176 B1 | 12/1990 |
| EP | 0458877 B1 | 4/1991 |
| EP | 0515324 A1 | 11/1992 |
| EP | 0547135 B1 | 6/1993 |
| EP | 0871414 | 9/1995 |
| EP | 0 592 410 B1 | 10/1995 |
| EP | 0756498 | 10/1995 |
| EP | 0 592 410 B1 | 11/1995 |
| EP | 0786970 | 5/1996 |
| EP | 0729364 B1 | 9/1996 |
| EP | 0756498 B1 | 5/1997 |
| EP | 0778775 B1 | 6/1997 |
| EP | 0786970 | 8/1997 |
| EP | 0888142 | 9/1997 |
| EP | 0971649 | 10/1998 |
| EP | 0928615 A1 | 7/1999 |
| EP | 1051204 | 7/1999 |
| EP | 1089676 | 12/1999 |
| EP | 0986348 B1 | 3/2000 |
| EP | 1117446 | 4/2000 |
| EP | 1 164 976 | 8/2000 |
| EP | 1158937 | 9/2000 |
| EP | 1 251 805 B1 | 10/2000 |
| EP | 1041942 B1 | 10/2000 |
| EP | 1041943 B1 | 10/2000 |
| EP | 1171061 | 10/2000 |
| EP | 1206179 | 2/2001 |
| EP | 1 233 731 | 5/2001 |
| EP | 1117446 B1 | 7/2001 |
| EP | 1 255 510 | 8/2001 |
| EP | 1259193 | 9/2001 |
| EP | 1 233 731 B1 | 5/2002 |
| EP | 1 330 213 | 5/2002 |
| EP | 1206179 B1 | 5/2002 |

| | | |
|---|---|---|
| EP | 1347785 | 8/2002 |
| EP | 1235537 | 9/2002 |
| EP | 1248655 | 10/2002 |
| EP | 1251804 B1 | 10/2002 |
| EP | 1257305 | 11/2002 |
| EP | 0 971 649 B1 | 12/2002 |
| EP | 1395208 | 12/2002 |
| EP | 1 401 359 | 1/2003 |
| EP | 1406561 | 1/2003 |
| EP | 1281357 A2 | 2/2003 |
| EP | 1281375 A2 | 2/2003 |
| EP | 1408882 | 2/2003 |
| EP | 1 435 878 | 4/2003 |
| EP | 1 435 879 | 4/2003 |
| EP | 1 441 672 | 6/2003 |
| EP | 1 017 868 B1 | 9/2003 |
| EP | 1354569 A1 | 10/2003 |
| EP | 1494616 | 10/2003 |
| EP | 1 519 697 | 1/2004 |
| EP | 1 539 047 | 4/2004 |
| EP | 1551274 | 4/2004 |
| EP | 1 560 542 | 5/2004 |
| EP | 1414295 | 5/2004 |
| EP | 1 603 493 | 9/2004 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1 663 070 | 3/2005 |
| EP | 1 253 875 B1 | 4/2005 |
| EP | 1 667 614 | 4/2005 |
| EP | 1 251 803 B1 | 6/2005 |
| EP | 1 702 247 | 7/2005 |
| EP | 1734902 | 8/2005 |
| EP | 1469797 B1 | 11/2005 |
| EP | 1835948 | 6/2006 |
| EP | 1 690 515 A | 8/2006 |
| EP | 1863545 | 9/2006 |
| EP | 1893132 | 11/2006 |
| EP | 1901681 | 12/2006 |
| EP | 1 255 510 B1 | 3/2007 |
| EP | 1835948 | 9/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| FR | 2828263 A1 | 2/2003 |
| GB | 2433700 A | 7/2007 |
| GB | 2440809 A | 2/2008 |
| JP | 2003-523262 | 8/2003 |
| JP | 2003-524504 | 8/2003 |
| JP | 2005-118585 | 5/2005 |
| JP | 2007-296375 | 11/2007 |
| JP | 2008539305 | 11/2008 |
| WO | WO-90/09102 | 8/1990 |
| WO | WO 95/11055 A1 | 4/1995 |
| WO | WO-95/24873 | 9/1995 |
| WO | WO-95/28183 | 10/1995 |
| WO | WO-96/13227 | 5/1996 |
| WO | WO-97/32615 | 9/1997 |
| WO | WO-98/43556 | 10/1998 |
| WO | WO-98/46165 | 10/1998 |
| WO | WO-99/37337 | 7/1999 |
| WO | WO-99/66863 | 12/1999 |
| WO | WO 00/15148 | 3/2000 |
| WO | WO-00/18445 | 4/2000 |
| WO | WO 00/25702 A1 | 5/2000 |
| WO | WO 00/47139 A1 | 8/2000 |
| WO | WO-00/53125 | 9/2000 |
| WO | WO-00/62714 | 10/2000 |
| WO | WO-01/10209 A1 | 2/2001 |
| WO | WO 01/35870 A1 | 5/2001 |
| WO | WO 01/41679 A1 | 6/2001 |
| WO | WO-01/51104 A1 | 7/2001 |
| WO | WO 01/54625 A1 | 8/2001 |
| WO | WO-01/58503 A1 | 8/2001 |
| WO | WO 01/62189 A1 | 8/2001 |
| WO | WO 01/64137 A1 | 9/2001 |
| WO | WO 02/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO-03/009785 A1 | 2/2003 |
| WO | WO 03/011195 A2 | 2/2003 |
| WO | WO 03/013239 | 2/2003 |
| WO | WO 03/028592 A1 | 4/2003 |
| WO | WO 03/047468 A1 | 6/2003 |
| WO | WO-03/079928 A2 | 10/2003 |
| WO | WO 03/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO 2004/043301 A1 | 5/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/021063 A2 | 3/2005 |
| WO | WO 2005/034812 A1 | 4/2005 |
| WO | WO 2005/062980 A1 | 7/2005 |
| WO | WO 2005/062980 A2 | 7/2005 |
| WO | WO-2005/072654 A1 | 8/2005 |
| WO | WO 2006/066327 | 6/2006 |
| WO | WO-2006/066327 A1 | 6/2006 |
| WO | WO 2005/076890 A1 | 7/2006 |
| WO | WO 2006/076890 A1 | 7/2006 |
| WO | WO-2006/102063 A2 | 9/2006 |
| WO | WO 2006/108090 A2 | 10/2006 |
| WO | WO-2006/124649 A2 | 11/2006 |
| WO | WO 2006/124649 A2 | 11/2006 |
| WO | WO 2006/127756 A2 | 11/2006 |
| WO | WO 2006/127765 A1 | 11/2006 |
| WO | WO-2006/132948 A1 | 12/2006 |
| WO | WO 2007/047488 A2 | 4/2007 |
| WO | WO 2007/047945 A2 | 4/2007 |
| WO | WO 2007/051620 A1 | 5/2007 |
| WO | WO 2007/059252 A1 | 5/2007 |
| WO | WO-2007/071436 A2 | 6/2007 |
| WO | WO 2007/098232 A2 | 8/2007 |
| WO | WO 2007/120543 A1 | 10/2007 |
| WO | WO-2008/028569 A1 | 3/2008 |
| WO | WO 2008/035337 A | 3/2008 |
| WO | WO 2008/045949 | 4/2008 |
| WO | WO 2008/070797 A2 | 6/2008 |
| WO | WO 2006/076890 | 7/2008 |
| WO | WO 2008/079962 A1 | 7/2008 |
| WO | WO 2008/101083 A2 | 8/2008 |
| WO | WO 2008/125153 A1 | 10/2008 |
| WO | WO 2008/138584 A1 | 11/2008 |
| WO | WO 2008/150529 A | 12/2008 |

OTHER PUBLICATIONS

Translation of Aortenklappenbioprothese erfolgreich in der Entwicklung (2 pages).
Screen shots from http://www.fraunhofer.de/presse/filme/2006/index.jsp (2 pages), 2006.
Liang, Ma, et al., "Double-crowned valved stents for off-pump mitral valve replacement," European Journal of Cardio-Thoracic Surgery, 194-198 (5 pages), Jun. 13, 2005.
Huber, Christoph, et al. "Direct Access Valve Replacement (DAVR)—are we entering a new era in cardiac surgery?" European Journal of Cardio-Thoracic Surgery, 380-385, (6 pages), Jan. 19, 2006.
Translation of DE 19546692 A1 (4 pages).
Translation of EP 1469797 B1 (16 pages).
File history for German Patent DE 195 46 692 filed Dec. 14, 1995 and patented Jul. 11, 2002.

* cited by examiner

STENT FOR THE POSITIONING AND ANCHORING OF A VALVULAR PROSTHESIS IN AN IMPLANTATION SITE IN THE HEART OF A PATIENT

This application is a continuation in part application of U.S. patent application Ser. No. 12/285,544 filed Oct. 8, 2008, which is a continuation in part application of U.S. patent application Ser. No. 12/071,814 filed Feb. 26, 2008, the entire contents of which are hereby incorporated herein by reference.

The present invention relates to a stent for the positioning and anchoring of a valvular prosthesis in an implantation site in the heart of a patient. Specifically, the present invention relates to an expandable stent for an endoprosthesis used in the treatment of a stenosis (narrowing) of a cardiac valve and/or a cardiac valve insufficiency.

The expression "narrowing (stenosis) of a cardiac valve and/or cardiac valve insufficiency" is intended to include a functional defect of one or more cardiac valves, which is either genetic or has developed. A cardiac defect of this type might affect each of the four heart valves, although the valves in the left ventricle (aortic and mitral valves) are affected much more often than the right-sided part of the heart (pulmonary and tricuspid valves). The functional defect can result in narrowing (stenosis), inability to close (insufficiency) or a combination of the two (combined vitium). This invention relates to an expandable stent for inserting a heart valve stent in a patient's body for treating such a heart valve defect.

In the current treatment of severe narrowing of a cardiac valve and/or cardiac valve insufficiency, the narrowed or diseased cardiac valve is replaced with a valvular prosthesis. Biological or mechanical valves models, which are typically surgically sewn into the cardiac valve bed through an opening in the chest after removal of the diseased cardiac valve, are used for this purpose. This operation necessitates the use of a heart-lung machine to maintain the patient's circulation during the procedure and cardiac arrest is induced during implantation of the prosthesis. This is a risky surgical procedure with associated dangers for the patient, as well as a long post-operative treatment and recovery phase. Such an operation can often not be considered with justifiable risk in the case of polypathic patients.

Minimally-invasive forms of treatment have been developed recently which are characterized by allowing the procedure to be performed under local anesthesia. One approach provides for the use of a catheter system to implant a self-expandable stent to which is connected a collapsible valvular prosthesis. Such a self-expandable endoprosthesis can be guided via a catheter system to the implantation site within the heart through an inguinal artery or vein. After reaching the implantation site, the stent can then be unfolded.

To this end, it is known that a stent may be comprised of, for example, a plurality of self-expanding longitudinal stent segments, the segments being articulated relative to one another. In order to anchor the stent securely in position in an appropriate blood vessel close to the heart, anchoring barbs are frequently used to engage with the vascular wall.

An expandable stent for the fastening and anchoring of a valvular prosthesis is known from printed publication DE 10 010 074 A1, whereby the stent is essentially formed from wire-shaped, interconnected segments. DE 10 010 074 A1 proposes a stent for fastening and anchoring a valvular prosthesis, the stent having different arched elements which assume the function of fastening and supporting the valvular prosthesis at the site of implantation. Specifically, three identically-configured positioning arches spaced 120° from one another respectively are used. These positioning arches are connected to one another by means of solid body articulations. In addition to the positioning arches, complementary curved retaining arches serve to anchor the endoprosthesis by pressing radially against the vascular wall following the unfolding of the stent.

However, there is a risk of inexact or incorrect implantation of a valvular prosthesis using the solutions described above. Expressed in another way, there is a need for exact positioning and longitudinal alignment of an implanted valvular prosthesis. In particular, it is only possible using great skill on the part of the attending surgeon or cardiologist—if at all—to position a stent sufficiently precisely, in both a lateral and longitudinal direction, to ensure that the associated valvular prosthesis is located in the correct area of the patient's diseased heart valve.

Among other things, inexact implantation of a sub-optimally positioned valvular prosthesis can lead to leakage or valvular insufficiency which results in considerable ventricular stress. For example, if a valvular prosthesis is implanted too far above the plane of the native heart valve, this can lead to closure or blocking of the coronary artery ostia (inlet orifice of coronaries) and thus to fatal coronary ischemia and myocardial infarction.

Therefore, for the optimal treatment of a narrowed cardiac valve or a cardiac valve insufficiency, it is necessary to position a stent, to which a valvular prosthesis is affixed, as precisely as possible at the site of implantation of the cardiac valve to be treated.

An endoprosthesis for treating aortic valve insufficiency is known from printed publication DE 20 2007 005 491 U1. The endoprosthesis comprises a valvular prosthesis and a stent to position and anchor the valvular prosthesis at the implantation site in the patient's heart. A stent having several (multiple, normally three, but two in case of bicuspid valve) positioning arches is employed in this endoprosthesis. In the implanted state of the stent, these positioning arches extend radially and serve to engage in the pockets of the native (diseased) cardiac valve to be treated. The valvular prosthesis affixed to the stent can then self-position into the plane of the cardiac valve. Retaining arches abut against the vascular wall of the aorta in the implanted state of the endoprosthesis, form a force-fit connection and are used to anchor the endoprosthesis.

While the positioning arches enable optimal positioning of the stent of this endoprosthesis at the site of implantation in the patient's heart, what cannot be ensured is that the valvular prosthesis attached to the proximal end of the stent is actually also positioned in the plane of the cardiac valve. In particular, substantial forces act on the valvular prosthesis during the filling phase of the heart cycle (diastole), which can lead to the valvular prosthesis displacing longitudinally relative the stent. Due to this longitudinal displacement of the implanted valvular prosthesis, which occurs in the heart and blood vessels especially because of the peristaltic motion of the heart, the implanted valvular prosthesis may no longer be able to provide a secure seal.

Moreover, there is the danger that, because of the longitudinal displacement of the valvular prosthesis relative to the stent occurring with the peristaltic motion, the threads or sutures used to fasten the valvular prosthesis to the stent may chafe against the stent. It can therefore not be excluded that the fastening threads may fray over the course of time and thus lose their fastening function. This would result in at least a partial separation of the valvular prosthesis from the stent, which in turn can lead to leakages, an inappropriate positioning or even complete detachment of the valvular prosthesis.

On the basis of the problems outlined above, certain embodiments of the present invention address the issue of providing a self-expandable endoprosthesis for treating a narrowed cardiac valve or a cardiac valve insufficiency which realizes optimum positioning accuracy and anchoring of a valvular prosthesis to be implanted. In addition, the treatment of the narrowed cardiac valve or cardiac valve insufficiency should be by way of a simple procedure to enable routine treatment of narrowed cardiac valve or cardiac valve insufficiency without major stress to the patient.

A further task of certain embodiments of the present invention lies in specifying an endoprosthesis for the treatment of a stenosed cardiac valve or a cardiac valve insufficiency, whereby the endoprosthesis can be anchored securely at the site of implantation in the patient's heart. In addition, certain embodiments of the present invention also address the issue of substantially preventing displacement of an implanted valvular prosthesis from its ideal site of implantation in spite of the forces acting on the endoprosthesis during the filling phase of the heart cycle.

From one aspect, an expandable stent is proposed in accordance with certain embodiments of the present invention, the stent comprising at least one fastening portion by means of which a valvular prosthesis is connected to the stent. In addition, the stent comprises positioning arches and retaining arches. At least one positioning arch of the stent is connected with at least one retaining arch of the stent by a first connecting web. Additionally, the stent further comprises at least one auxiliary arch which interconnects the arms of respective retaining arches.

The at least one fastening portion extends along the longitudinal axis of the stent and comprises a plurality of fastening holes distributed in a longitudinal direction at discrete positions along the length of the at least one fastening portion. Thread or thin wire may be guided through each fastening hole to secure the valvular prosthesis to the stent. The advantage of this feature is that longitudinal displacement of the valvular relative to the stent is substantially minimized once implanted and so the prosthesis is not unduly disturbed or weakened as a result of the heart's peristaltic motion.

In addition to fastening holes, the fastening portion may include one or more notches to assist the seating and retaining of suture material. The notches also assist with even attachment of the prosthesis to the stent and, similarly to the fastening holes, minimise longitudinal displacement of the prosthesis.

Depending from and between a pair of fastening portions is a fastening arch, over which valve tissue is laid. The fastening arch is located inside the circumference of the stent. In this way, the prosthesis tissue is separated and held away from positioning and retaining arches, thereby reducing the likelihood of these arches chaffing the tissue which, in turn may result in damage and weakening of the prosthesis. The fastening arch serves to anchor the lower edge of the valvular prosthesis and to tension the material so the prosthesis is effective as a valve. By having a fastening portion and fastening arches, the prosthesis is fully supported and anchored within the boundary of the stent. The combination of the two fastening mechanisms also provides a failsafe should one fastening mechanism fail. This is of particular relevance with suturing since a poorly sutured prosthesis will not be as effective as it should due to additional stresses and strains imparted to the prosthesis by the sutures. Thus, the arches allow fastening of the prosthesis in a manner that does not rely solely on suturing.

In an implanted configuration, the at least one positioning arches of the stent extends from the circumference of the stent in a generally radial direction. These positioning arches are designed to engage in the pockets of the native (diseased) cardiac valve that is being replaced which, in turn allows accurate positioning of the stent. Furthermore, on implantation, a positioning arch sits between the vascular wall and a leaflet of the native heart valve. The positioning arch then co-operates with a corresponding retaining arch resulting in clipping of the native leaflet between the two arches. In this way, the positioning and retaining arches together hold the stent in position and substantially eliminate axial rotation of the stent.

In a preferred embodiment, the positioning arch may be shaped to have a substantially convex shape. In other words, the end of the arch that is positioned in the native valve leaflet may be curved towards the inside of the stent or towards the longitudinal axis of the stent. In this way, the shape of the each positioning arch provides an additional clipping force against the native valve leaflet.

The at least one retaining arch is connected to a positioning arch by a connecting web. The retaining arch extends radially in the implanted state of the stent such that the at least one retaining arch presses against the wall of the blood vessel in which the stent is deployed with a radially-acting tensioning force. In situ, the ends of each retaining arch also fits underneath the aortic valve annulus, providing further means for locating and anchoring the stent. In addition to the at least one retaining arch, certain embodiments of the invention provide for the stent to further comprise at least one auxiliary arch which interconnects the respective arms of the at least one retaining arch connected to the at least one positioning arch. As with the at least one retaining arch, the at least one auxiliary arch also protrudes radially in the expanded state of the stent such that the at least one auxiliary arch also presses against the wall of the blood vessel in which the stent is deployed with a radially-acting tensioning force.

The stent may also include radial arches positioned between each positioning arch, with each radial arch extending upwards towards the distal end of the stent. The radial arches provide additional means by which the stent may be retained within a catheter before and during implantation, and provide means by which the stent may be recaptured after implantation. The arches also add radial strength to the distal end of the stent.

In the at least one fastening portion of the stent, by means of which the valvular prosthesis can be fastened to the stent, a plurality of fastening holes and optionally one or more notches is provided. These fastening holes and notches are longitudinally distributed at given positions on the fastening portion and guide at least one thread or thin wire to fasten the valvular prosthesis to the stent, thereby enabling a precise positioning of the valvular prosthesis on the stent. Each individual fastening hole and notch provided in the at least one fastening portion thereby serves to guide a thread or thin wire with which the valvular prosthesis is affixed or sewn to the fastening portion of the stent.

The means provided for fastening the valvular prosthesis to the fastening portion of the stent (thread or thin wire) is guided by way of the fastening holes and notches so that a longitudinal displacement of the valvular prosthesis relative to the stent is substantially minimized. This also allows exact positioning of the valvular prosthesis relative the stent.

The secure and defined fixing of the valvular prosthesis to the at least one fastening portion of the stent moreover effectively prevents the means used to fasten the valvular prosthesis to the stent (threads or thin wires) from rubbing against the stent and thus degrading after a longer period of use.

In order to configure the plurality of fastening holes and any notches in the fastening portion, the at least one fastening portion is preferably configured as—in comparison to the respective arms of the positioning arch, retaining arch and auxiliary retaining arch—a widened segment. Thus, the fastening portion is a stent segment which comprises a relatively large amount of material, facilitating movement and position analysis when the stent is being implanted. For example, when fluoroscopy (cardiac catheterization=LHK) or ultrasound (trans-esophageal echocardiogram=TEE) is used to monitor the insertion procedure, the fastening portion of the stent is particularly distinguishable.

A preferred realization of the stent according to a particular embodiment the invention provides for a fastening portion to be configured within each arm of the stent's retaining arch.

In order to reinforce the respective retaining arches of the stent, the auxiliary arch as already mentioned above is provided. The auxiliary arch extends from the lower ends of the fastening portion and connects the respective arms of two neighboring retaining arches.

In manufacturing the stent used in the endoprosthesis according to a particular embodiment of the invention, it is conceivable for the stent to exhibit a structure integrally cut from a portion of tube, in particular from a small metal tube, which incorporates the positioning arches, retaining arches and auxiliary retaining arches as well as the at least one fastening portion with defined fastening holes and notches. Specifically, it is conceivable to use a laser to cut the stent structure from the small metal tube, whereby the structure is thereafter subject to an applicable shaping and thermal treatment process so that the stent can transform from a collapsed state during implantation into an expanded state at the site of implantation. This shaping and thermal treatment process is advantageously performed gradually in order to prevent damage to the stent structure.

Particularly preferred is for the stent to exhibit a structure integrally cut from a small metal tube in which each positioning arch is allocated one retaining arch, and in which each upper end portion of the positioning arch towards the upper end of the stent is connected with the upper end portion of the associated retaining arch via a first connecting web. The at least one fastening portion, in which the plurality of fastening holes is provided, is thereby preferably configured within an arm of the retaining arch.

The stent preferably exhibits an integrally-formed structure which can transform from a first predefinable shape into a second predefinable shape, whereby the stent exhibits a first predefinable shape (collapsed shape) during insertion into the patient's body and a second predefinable shape (expanded shape) once implanted. Because of the stent's design, during the transition of the stent from the first predefinable shape into the second predefinable shape, the positioning arches, retaining arches and auxiliary arches are radially expanded as a function of the cross-sectional expansion of the stent. The stent's second shape is thereby preferably selected such that when the stent is expanded, the retaining arch and the auxiliary arch abut against the wall of the blood vessel in which the stent is deployed. In addition, the ends of the retaining arches are positioned beneath the native valve annulus, thereby providing additional anchoring of the stent.

To achieve a secure anchoring of the stent at the site of implantation, both the retaining and auxiliary arches should press against the wall of the vessel with a radial force, whereby this radial force can be set by subjecting the stent structure to a suitable shaping and thermal treatment process.

It is to be understood that the term "upper" refers to the stent when viewed in its implanted state. In other words, the term "upper" refers to the distal end of the stent which, when implanted, is sited away from the heart. Similarly, use of the term "lower" refers to a proximal position on the stent which is located towards the ventricle side of the heart when the stent is viewed in its implanted position.

A preferred embodiment of the stent according to the invention provides for the positioning arches and the associated retaining arches as well as auxiliary arches each to exhibit an essentially U-shaped, T-shaped or V-shaped structure which is closed toward the lower end of the stent. It is particularly preferred for each positioning arch to be cut from the material portion of a small metal tube from which the essentially U-shaped, T-shaped or V-shaped structure of the associated retaining arch was taken. The respective auxiliary arches are preferably cut from a material portion of the small metal tube situated between the essentially U-shaped, T-shaped or V-shaped retaining arch structures.

This preferred embodiment of the stent structure thus provides for the respective retaining and auxiliary arches of the stent to form the lower region of the endoprosthesis, whereby the positioning arches are configured symmetrically to the retaining arches although preferably disposed somewhat further toward the upper region of the endoprosthesis.

The respective upper ends of the positioning arches are connected to the respective upper ends of the associated retaining arches by means of a first connecting web in the upper region of the endoprosthesis. The fastening portions are configured in the respective arms of the retaining arch. In the expanded state of the stent, both the lower region with the fastening portions, as well as the connecting web disposed at the upper end of the stent between the respective positioning and retaining arches, spread out so that a radially-acting force is exerted on the blood vessel wall from both the lower region of the stent as well as the upper end of the stent, thereby enabling secure anchoring of the stent at the site of implantation.

In a preferred embodiment, the stent exhibits in its first shape (collapsed shape) an outer diameter of approximately 4 to 8 mm and a length of between 30 mm and 40 mm, preferably between 34.0 and 39.0 mm, and more preferably between 34.37 mm and 38.37 mm. This allows the stent to be inserted easily into the patient's body, for example with a 21F delivery system, and to be used with a valvular prosthesis having a diameter of between 19 mm and 28 mm. The aforementioned length specifications are the dimensions currently preferred, based on which the stent becomes suitable for the majority of patients to be treated.

In order to achieve a particularly secure anchoring of the implanted stent with the stretched valvular prosthesis affixed thereto, it is further conceivable for the stent to be subject to a shaping and thermal treatment process during its manufacture such that the finished stent exhibits a slightly concave configuration tapering toward its lower end in its second shape.

In other words, the lower end portion of the stent, i.e., that area in which the valvular prosthesis is fastened, exhibits a somewhat tapered diameter in comparison to the upper end portion. Specifically, it has been seen that, when the stent is in it second shape and the upper end of the stent exhibits a diameter approximately 10-25% larger than the diameter of its lower end, radial forces are generated particularly at the stent's upper end. This enables a secure hold of the stent in the blood vessel without damaging the arterial wall. This configuration also provides secure anchoring that is able to withstand the peristaltic motion of the heart and the arterial wall. The somewhat lesser radial force exerted by the lower end of the stent not only serves to anchor the stent in the blood vessel but also to stretch the valvular prosthesis attached at the lower end and reliably seal the prosthesis against the arterial wall. It is of course also conceivable to design the concave configuration of the stent in its second shape to be of greater or lesser concavity.

It is preferable for the lower end area of the stent, when in its second shape, to exhibit a diameter of between 22 mm and 33 mm, preferably between 25 mm and 31 mm. It is conceivable for the stent to exhibit two or more differently dimensioned sizes whereby the optimal stent size can be selected depending upon specific patient. In addition, exact and patient-specific dimensions of the stent—starting from a given stent size—can be realized by appropriately curing the stent, in particular by a thermal treatment process.

In a particularly preferred realization, the stent comprises a valvular prosthesis, preferably a biological or pericardial valvular prosthesis, which is attached to the at least one fastening portion of the stent by means of a thread or the like.

A shape memory material is preferably used as the material for the stent, the material being designed such that the stent can transform from a temporary shape into a permanent shape under the influence of an external stimulus. The temporary shape is thereby the stent's first shape (i.e. the collapsed state of the stent), while the permanent shape is assumed in the stent's second shape (i.e. in the expanded state of the stent). In particular, use of a shape memory material such as nitinol, i.e. an equiatomic alloy of nickel and titanium, allows for a particularly gentle implantation procedure when implanting the stent.

When manufacturing the stent preferably made from a shape memory material, the stent structure is preferably shaped after it has been cut from a tube. Once the desired shape has been formed, this shape is "fixed", this process being known as "programming". Programming may be effected by heating the stent structure, forming the stent into the desired shape and then cooling the stent. Programming may also be effected by forming and shaping the stent structure at lower temperature, this being known as "cold stretching." The permanent shape is thus saved, enabling the stent to be stored and implanted in a temporary, non-formed shape. If an external stimulus then acts on the stent structure, the shape memory effect is activated and the saved, permanent shape restored.

A particularly preferred embodiment provides for the external stimulus to be a definable switching temperature. It is thus conceivable that the stent material needs to be heated to a higher temperature than the switching temperature in order to activate the shape memory effect and thus regenerate the saved permanent shape of the stent. A specific switching temperature can be preset by the relevant selection of the chemical composition of the shape memory material.

It is particularly preferred to set the switching temperature to be in the range of between room temperature and the patient's body temperature. Doing so is of advantage, especially with regard to the medical device being used as an implant in a patient's body. Accordingly, all that needs to be ensured in this regard when implanting the stent is that the stent is warmed up to the patient's body temperature (36° C.) at the site of implantation to activate the shape memory effect of the stent material.

The following will make reference to the included drawings in describing preferred embodiments of the stent according to the present invention in greater detail.

Shown are:

FIG. 1a a perspective side view of a cardiac valve stent in accordance with a first embodiment of the invention, where the cardiac valve stent is shown in its collapsed state;

FIG. 1b a perspective side view of the cardiac valve stent in accordance with the first embodiment of the invention, where the cardiac valve stent is shown in its expanded state;

FIG. 1c a perspective top plan view of the proximal end of the cardiac valve stent in accordance with the first embodiment of the invention, where the cardiac valve stent is shown in its expanded state;

FIG. 1d a perspective side view of an endoprosthesis for treating a narrowed cardiac valve or a cardiac valve insufficiency, where the endoprosthesis comprises the cardiac valve stent according to the first embodiment of the invention for holding a valvular prosthesis;

FIG. 1e a two-dimensional projection of a cutting pattern applicable to manufacturing the cardiac valve stent according to the first embodiment of the invention in order to cut a cardiac valve stent pursuant to FIG. 1a integrally from a portion of tube, in particular a small metal tube;

FIG. 2a a perspective side view of a cardiac valve stent according to a second embodiment of the invention, where the cardiac valve stent is shown in its collapsed state;

FIG. 2b a first perspective side view of the cardiac valve stent according to the second embodiment of the invention, whereby the cardiac valve stent is shown in its expanded state;

FIG. 2c a second perspective side view of the cardiac valve stent according to the second embodiment of the invention, where the cardiac valve stent is shown in its expanded state;

FIG. 2d a perspective side view of an endoprosthesis for treating a narrowed cardiac valve or a cardiac valve insufficiency, where the endoprosthesis comprises the cardiac valve stent according to the second embodiment of the invention for holding a valvular prosthesis;

FIG. 2e a two-dimensional projection of a cutting pattern for manufacturing the cardiac valve stent according to the second embodiment of the invention to enable a cardiac valve stent pursuant FIG. 2a to be cut integrally from a portion of a tube, in particular a small metal tube;

FIG. 3 a two-dimensional projection of a cutting pattern for manufacturing a cardiac valve stent according to the third embodiment of the invention to enable a cardiac valve stent to be cut integrally from a portion of a tube, in particular a small metal tube;

FIG. 4 a two-dimensional projection of a cutting pattern for manufacturing a cardiac valve stent according to the fourth embodiment of the invention to enable a cardiac valve stent to be cut integrally from a portion of a tube, in particular a small metal tube;

FIG. 5a a first perspective side view of the cardiac valve stent according to the fifth embodiment of the invention, whereby the cardiac valve stent is shown in its expanded state;

FIG. 5b a second perspective side view of the cardiac valve stent according to the fifth embodiment of the invention, whereby the cardiac valve stent is shown in its expanded state;

FIG. 5c a top view of the upper end of the cardiac valve stent according to the fifth embodiment of the invention, whereby the cardiac valve stent is shown in its expanded state;

FIG. 5d a two-dimensional projection of a cutting pattern applicable to manufacturing a cardiac valve stent according to the fifth embodiment of the invention in order to cut a cardiac valve stent pursuant to FIG. 5a integrally from a portion of tube, in particular a small metal tube;

FIG. 6a a first perspective side view of the cardiac valve stent according to the sixth embodiment of the invention, whereby the cardiac valve stent is shown in its expanded state;

FIG. 6b a second perspective side view of the cardiac valve stent according to the sixth embodiment of the invention, whereby the cardiac valve stent is shown in its expanded state;

FIG. 6c a third perspective side view of the cardiac valve stent according to the sixth embodiment of the invention, whereby the cardiac valve stent is shown in its expanded state;

FIG. 6d a two-dimensional projection of a cutting pattern applicable to manufacturing a cardiac valve stent according to the sixth embodiment of the invention in order to cut a cardiac valve stent pursuant to FIG. 6a integrally from a portion of a tube, in particular a small metal tube;

FIG. 6e a perspective side view of an endoprosthesis for treating a narrowed cardiac valve or a cardiac valve insufficiency, where the endoprosthesis comprises the cardiac valve stent according an embodiment of the invention for holding a valvular prosthesis, whereby the cardiac valve stent is shown in a partly expanded state;

FIG. 6f a perspective side view of an endoprosthesis for treating a narrowed cardiac valve or a cardiac valve insufficiency, where the endoprosthesis comprises the cardiac valve stent according to the sixth embodiment of the invention for holding a valvular prosthesis, whereby the cardiac valve stent is shown in an expanded state;

FIG. 6g a perspective detail view of the head portion of a retaining arch belonging to the cardiac valve stent of the endoprosthesis shown in FIG. 6f;

FIG. 6h a perspective detail view of an additional fastening portion belonging to the cardiac valve stent of the endoprosthesis shown in FIG. 6f;

FIG. 6i a top view of the lower end of the endoprosthesis shown in FIG. 6f;

FIG. 7a a two-dimensional projection of a cutting pattern for manufacturing a cardiac valve stent according to the seventh embodiment of the invention to enable a cardiac valve stent to be cut integrally from a portion of a tube, in particular a small metal tube;

FIG. 7b a first perspective side view of the cardiac valve stent according to the seventh embodiment of the invention, whereby the cardiac valve stent is shown in its expanded state;

FIG. 7c a second perspective side view of the cardiac valve stent according to the seventh embodiment of the invention, whereby the cardiac valve stent is shown in its expanded state;

FIG. 8a a two-dimensional projection of a cutting pattern for manufacturing a cardiac valve stent according to the eighth embodiment of the invention to enable a cardiac valve stent to be cut integrally from a portion of a tube, in particular a small metal tube;

FIG. 8b a first perspective side view of the cardiac valve stent according to the eighth embodiment of the invention, whereby the cardiac valve stent is shown in its expanded state;

FIG. 8c a second perspective side view of the cardiac valve stent according to the eighth embodiment of the invention, whereby the cardiac valve stent is shown in its expanded state;

FIG. 9a a two-dimensional projection of a cutting pattern for manufacturing a cardiac valve stent according to the ninth embodiment of the invention to enable a cardiac valve stent to be cut integrally from a portion of a tube, in particular a small metal tube;

FIG. 9b a perspective side view of the cardiac valve stent according to the ninth embodiment of the invention, whereby the cardiac valve stent is shown in its expanded state;

FIG. 10 a two-dimensional projection of a cutting pattern for manufacturing a cardiac valve stent according to the tenth embodiment of the invention to enable a cardiac valve stent to be cut integrally from a portion of a tube, in particular a small metal tube;

FIG. 11 a two-dimensional projection of a cutting pattern for manufacturing a cardiac valve stent according to the eleventh embodiment of the invention to enable a cardiac valve stent to be cut integrally from a portion of a tube, in particular a small metal tube; and FIG. 12a-c a process sequence illustrating a transarterial implantation of an endoprosthesis comprising a cardiac valve stent in accordance with certain embodiments of the invention.

Both the right and left halves of the human heart consist of a ventricle and an atrium. These cavities are separated by the septum of the heart, divided into the atrial septum (septum interatriale) and the ventricular septum (septum interventriculare). Blood can only flow in one direction through the chambers of the heart due to the cardiac valves situated between the atria and ventricles and in the arteries connected to the ventricles which function like mechanical valves. The superior and inferior vena cava (vena cava superior et inferior) flow into the right atrium. They supply the oxygen-depleted (venous) blood from the systemic circulation to the heart. The tricuspid valve which, like a mechanical valve, prevents a reverse flow of blood into the atrium upon ventricular contraction (systole) is situated between the right atrium and the right ventricle. It comprises three segments which are affixed like flaps to the ventricular musculature by ligaments (hence also called the "flap valve"). The two pulmonary arteries depart the right ventricle of the heart via a common trunk (truncus pulmonalis). There is also a valve between the ventricle and the pulmonary trunk, the so-called pulmonary valve. This type of valve is also called a semilunar valve due to its shape. The pulmonary arteries supply the oxygen-depleted blood to the pulmonary circulation.

Oxygen-rich (arterial) blood then usually flows through four pulmonary veins from the pulmonary circulation to the left atrium. From there, it reaches the left ventricle through a further flap valve, the mitral valve. The outflow is carried by the aorta which, like the pulmonary artery, has a semilunar valve (aortic valve).

During a heart cycle, the atria fill first while the ventricles concurrently disgorge the blood into the arteries. When the ventricular musculature relaxes, the flap valves open due to the drop in pressure in the ventricle and the blood flows in from the atria (auricular systole). This is supported by a contraction of the atria. Ventricular contraction follows: the ventricular musculature contracts, the pressure rises, the flap valves close and the blood can now only flow into the arteries through the now-opened semilunar valves. A reverse blood flow from the arteries during the relaxation phase (diastole) is prevented by the closing of the semilunar valves such that the direction of flow is determined solely by the valves.

The four cardiac valves work like mechanical valves in the heart and prevent a reverse flow of blood in the wrong direction. Each half of the heart has a flap valve (atrioventricular valve) and a semilunar valve. The atrioventricular valves are situated between the atrium and the ventricle and are called the bicuspid/mitral valve and the tricuspid valve. The semilunar valves are situated between the ventricle and the vascular outflow and are called the pulmonary valve and the aortic valve respectively.

A valve defect; i.e. a dysfunction of a cardiac valve's function, can affect any of the four cardiac valves, although the valves on the left side of the heart (aortic and mitral valves) are affected considerably more frequently than those on the right side of the heart (pulmonary and tricuspid valves). Dysfunction can encompass constriction (stenosis), insufficiency or a combination of the two (combined vitium).

In medicine, the term "aortic valve insufficiency", or "aortic insufficiency" for short, refers to the defective closing of the heart's aortic valve and the diastolic reverse flow of blood from the aorta into the left ventricle as a result. Depending on the severity of the aortic insufficiency and the extent of resistance to aortic depletion, the volume of reverse flow can be up to two thirds of the left ventricle's ejection volume (normal cardiac output 40 to 70 ml). This results in characteristically high blood pressure amplitude. This regurgitate blood flow increases the diastolic filling of the left chamber and leads to a volume overload of this section of the heart, a consequence of which is eccentric hypertrophy.

Aortic valve stenosis is a valvular heart disease caused by the incomplete opening of the aortic valve. When the aortic valve becomes stenotic, it causes a pressure gradient between the left ventricle and the aorta. The more constricted the valve, the higher the gradient between the left ventricle and the aorta. For instance, with a mild aortic valve stenosis, the gradient may be 20 mmHg. This means that, at peak systole, while the left ventricle may generate a pressure of 140 mmHg, the pressure that is transmitted to the aorta will only be 120 mm Hg.

In individuals with aortic valve stenosis, the left ventricle has to generate an increased pressure in order to overcome the increased after load caused by the stenotic aortic valve and eject blood out of the left ventricle. The more severe the aortic stenosis, the higher the gradient is between the left ventricular systolic pressures and the aortic systolic pressures. Due to the increased pressures generated by the left ventricle, the myocardium (muscle) of the left ventricle undergoes hypertrophy (increase in muscle mass).

Angina in the setting of aortic valve stenosis is secondary to the left ventricular hypertrophy that is caused by the constant production of increased pressure required to overcome the pressure gradient caused by the aortic valve stenosis. While the myocardium (i.e. heart muscle) of the left ventricle gets thicker, the arteries that supply the muscle do not get significantly longer or bigger, so the muscle may become ischemic (i.e. doesn't receive an adequate blood supply). The ischemia may first be evident during exercise, when the heart muscle requires increased blood supply to compensate for the increased workload. The individual may complain of exertional angina. At this stage, a stress test with imaging may be suggestive of ischemia.

Mitral valve insufficiency (also called mitral insufficiency) is a frequent cardiac valve defect in human medicine and also in at least some animal species. It involves a closing defect or "leakage" of the heart's mitral valve which leads to reverse blood flow from the left ventricle into the left atrium during the ejection phase (systole).

The mitral valve functions like a mechanical valve between the left atrium and the left ventricle of the heart. It opens during the filling phase of the ventricle (diastole) and thus enables the inflow of blood from the atrium. At the beginning of the ejection phase (systole), the sudden increase in pressure in the ventricle leads to the closing of the valve and thus to a "sealing" of the atrium. In so doing, a pressure of only about 8 mmHg prevails in the atrium, while at the same time the systolic pressure of about 120 mmHg in the ventricle forces the blood along its usual path into the main artery (aorta).

In cases of severe mitral insufficiency, however, the regurgitation opening is larger than 40 mm$^2$ and the regurgitation volume greater than 60 ml, which can lead to serious and at times life-threatening changes.

In the acute stage, with a normal size to the left ventricle and the left atrium, there is a considerable increase of the pressure in the atrium and thus also in the pulmonary veins. This can be up to 100 mmHg which, given a normal condition to the pulmonary vessels, leads to immediate pulmonary oedema. The then predominantly reverse blood flow can result in insufficient outflow into the aorta and thus decreased blood flow to all the organs.

To treat a severe narrowed cardiac valve or cardiac valve insufficiency, it is necessary for a valvular prosthesis to perform the valve function of the narrowed, diseased or diseased cardiac valve. Essential in this respect is that the valvular prosthesis is securely positioned and anchored in the implantation site in the heart; i.e. in the plane of the (diseased) cardiac valve to be replaced, so that the valvular prosthesis is not displaced or shifted despite the, at times considerable, forces acting on it. An effective seal during systole is also important.

A cardiac valve stent 10, to which the valvular prosthesis 100 is appropriately affixed, is employed in accordance with at least certain embodiments of the invention to position and anchor said valvular prosthesis. A medical device for the treating of a narrowed cardiac valve or a cardiac valve insufficiency consisting of a cardiac valve stent 10 and a valvular prosthesis 100 affixed to the stent 10 will be referred to herein simply as endoprosthesis 1.

FIG. 1d shows a perspective side view of such an endoprosthesis 1 for treating a narrowed cardiac valve or a cardiac valve insufficiency, whereby the endoprosthesis 1 comprises a cardiac valve stent 10 to hold a valvular prosthesis 100 in accordance with a first embodiment of the invention. FIG. 2d likewise shows a perspective side view of a further endoprosthesis 1 for treating a narrowed cardiac valve or a cardiac valve insufficiency, whereby a cardiac valve stent 10 in accordance with a second embodiment of the invention is employed.

The following description will make reference to the drawings to describe preferred embodiments of the present invention in detail. The cardiac valve stent 10 according to certain embodiments of the invention (hereinafter referred to simply as "stent") exhibits an expandable structure which is able to transform from a first predefinable shape in which the stent 10 is in a collapsed state into a second predefinable shape in which the stent 10 is in an expanded state. FIG. 1a shows a side view of the stent 10 according to the first embodiment of the invention, whereby the stent 10 is in its collapsed state. FIG. 2a shows the collapsed stent 10 according to a second embodiment of the invention.

In the two embodiments, the stent 10 is introduced in a minimally-invasive fashion into the body of a patient in its first shape (cf. FIG. 1a and FIG. 2a) using an insertion catheter system (not explicitly shown in the drawings). During insertion, a valvular prosthesis 100 affixed to the stent 10 is likewise in a collapsed state. For the sake of clarity, however, both FIGS. 1a and 2a dispense with a representation of the valvular prosthesis 100 affixed to the stent 10.

Upon reaching the site of implantation in the patient's heart, the stent 10 transforms, through increments, into its second (expanded) shape in which also the valvular prosthesis 100 affixed to the stent 10 also unfolds and expands. The second, expanded shape is a permanent shape that has been set by programming. The completely expanded stent 10 according to the first/second embodiment of the invention with the likewise completely unfolded and expanded valvular prosthesis 100 affixed thereto is shown in FIG. 1d and FIG. 2d.

FIG. 1b and FIG. 1c show the completely expanded stent 10 according to the first embodiment of the invention from different perspectives without the valvular prosthesis 100. FIGS. 2b and 2c show the completely expanded stent 10 according to the second embodiment of the invention, likewise without the valvular prosthesis 100, from different perspectives.

The following will initially make reference to FIGS. 1a to 1e in describing the first embodiment of the stent 10.

The stent 10 according to the first embodiment exhibits a structure integrally cut from a portion of tube, in particular a small metal tube. The cutting pattern used to form the design of the stent is depicted in a two-dimensional projection in FIG. 1e.

In detail, the stent 10 has three positioning arches 15a, 15b, 15c which assume the function of self-positioning the stent into the plane of the pulmonary valve (valva trunci pulmonalis) or aortic valve (valva aortae). The positioning arches 15a, 15b, 15c exhibit a rounded head portion 20 which engages in the pockets T of the (diseased) cardiac valve to be treated during positioning of the stent 10 at the site of implantation in the heart (cf. FIG. 12a).

As well as providing a symmetry that matches that of the native valve, the provision of three positioning arches 15a, 15b, 15c also provides rotational accuracy, symmetry and stability. The stent 10 is of course not limited to the use of a total of three positioning arches.

The head portions 20 of the positioning arches 15a, 15b, 15c, respectively pointing towards the lower end 2 of the stent 10, are rounded so that the vascular wall will not be damaged when the positioning arches 15a, 15b, 15c engage in the pockets T of the cardiac valve H to be replaced. To improve movement and position analysis during the implanting of the stent 10 reference markers 21 are provided on or within the head portions 20 of the positioning arches 15a, 15b, 15c. Radio opaque markers or markers which can be activated by infrared or ultrasound lend themselves particularly well hereto.

The positioning arches 15a, 15b, 15c respectively exhibit an essentially U-shaped or V-shaped structure which is closed to the lower end of stent 10. Accordingly, each positioning arch 15a, 15b, 15c has a total of two arms 15a', 15a", 15b', 15b", 15c', 15c" respectively extending from the head portion 20 of the associated positioning arch 15a, 15b, 15c towards the upper end 3 of stent 10. By doing so, each two adjoining arms of two neighbouring positioning arches are connected to one another via a connecting portion 22.

For implanting and explanting the stent 10 with a suitable catheter system, the stent 10 comprises catheter retaining means 23 at its upper end 3. The connecting portions 22 are respectively connected to catheter retaining means 23 via a connecting web 25. The connecting webs 25 will hereinafter be referred to as "second connecting web 25".

The catheter retaining means 23 comprise oval-shaped heads which each comprise a corresponding oval-shaped eyelet 24. The shape of the catheter retaining means 23 complements a crown on the tip of a catheter of a catheter system used to implant/explant stent 10. The crown on the catheter tip has protruding elements that are configured as a negative of the catheter retaining means 23. Alternatively, the protruding elements are shaped to be complementary to the eyelets 24 and are configured as catheter retaining heads. This realization enables the protruding elements of the crown to form a releasable engagement with the upper area 3 of stent 10 to allow releasable attachment of the stent 10 to the tip of the catheter.

A first connecting web 17 extends essentially in the longitudinal direction L of stent 10 and has an upper end portion 17d and a lower end portion 17p. The upper end portion 17d opens into connecting portion 22 between the two arms 15a', 15a", 15b', 15b", 15c', 15c" of two neighboring positioning arches 15a, 15b, 15c, in addition to the previously-mentioned second connecting web 25. As can be seen in FIG. 1b, the first connecting webs 17 have an essentially inverted Y-shaped configuration and each exhibit a structure that diverges at its lower end portion 17p to give way to the respective arms 16a', 16a", 16b', 16b", 16c', 16c" of two neighboring retaining arches 16a, 16b, 16c.

In between each positioning arch 15 and retaining arch 16 is a fastening arch 19. As is shown particularly clearly in FIG. 1b, the fastening arch depends from the proximal end of fastening portion 11 and has a substantially U-shaped or V-shaped structure which is closed to the lower end of stent 10. As is shown in FIG. 1d, the fastening arches serve to support the lower end of valve prosthesis 100. The prosthesis 100 is shaped so that fastening arches 191, 19b and 19c are located in pockets of the valve material. The fastening arches 19a, 19b and 19c have a longitudinal shape that allows the arches to lie in line with the circumference of the stent 10. In this way, the arches 19 sit inside the positioning and retaining arches, thereby holding the valve material away from the stent structure. This reduces wear on the valve material by the stent once the prosthesis 1 has been implanted.

This stent design achieves an axially symmetrical structure, whereby each positioning arch 15a, 15b, 15c is allocated one fastening arch 19a, 19b, 19c and one retaining arch 16a, 16b, 16c. The stent 10 of the first embodiment depicted in FIGS. 1a to 1d thus comprises a total of three retaining arches 16a, 16b, 16c which constitutes a retaining segment of stent 10 for accommodating a valvular prosthesis 100 as depicted for example in FIG. 1d.

In the state of the stent 10 shown in FIG. 1a, in which stent 10 is in its first (collapsed) shape, the respective arms 15a', 15a", 15b', 15b", 15c', 15c" of the positioning arches 15a, 15b, 15c directly adjoin the respective arms 19a', 19a", 19b', 19b", 19c', 10c" of the fastening arches 19a, 19b, 19c which, in turn, directly adjoin the respective arms 16a', 16a", 16b', 16b", 16c', 16c" of the associated retaining arches 16a, 16b, 16c.

Reference is made to FIG. 1b, in which the stent 10 pursuant to the first embodiment is shown in its second, expanded shape. It can be particularly recognized from this representation that each positioning arch 15a, 15b, 15c and associated fastening arch 19a, 19b, 19c and retaining arch 16a, 16b, 16c respectively exhibit an essentially U-shaped or V-shaped structure which is closed towards the lower end 2 of the stent 10. Specifically, each positioning arch 15a, 15b, 15c is cut from a material section of a portion of a tube from which the essentially U-shaped or V-shaped structure of the associated fastening arch 19a, 19b, 19c was taken, as can be seen from the cutting pattern depicted in FIG. 1e.

A comparison of FIG. 1a to FIG. 1b shows that, upon the stent 10 expanding; i.e. when the stent 10 transforms from its first shape into its second shape, the stent 10 shortens in the longitudinal direction L while simultaneously enlarging in cross-section. In the expanded state of stent 10, the positioning arches 15a, 15b, 15c are expanded more in the radial direction at the lower end 2 of the stent 10 compared to the upper end 3 of stent 10. Since they protrude more in the radial direction, the positioning arches 15a, 15b, 15c can be deployed into the cardiac valve pockets T of the cardiac valve H to be replaced in a particularly easy manner.

Even when a certain anchoring of the stent 10 is achieved at the site of implantation in the heart due to the positioning arches 15a, 15b, 15c already protruding radially from stent 10 in the expanded state of the stent 10, it is noted that the contact force acting on the vascular wall from the positioning arches 15a, 15b, 15c is insufficient to securely anchor the stent 10 at the site of implantation. The previously-mentioned retaining arches 16a, 16b, 16c, which form the lower end 2 of stent 10, are provided for this reason. The retaining arches 16a, 16b, 16c protrude radially from the circumference of the stent 10 in its expanded state such that the retaining arches 16a, 16b, 16c press against the wall of the blood vessel in which the stent is deployed with a radially-acting contact force. In addition, the closed ends of the retaining arches 16a, 16b, 16c flare outwards, protruding radially still further from the circumference of the stent 10. This shape allows the ends of the retaining arches 16a, 16b, 16c to be positioned below the native valve annulus or to be positioned at least on the native valve annulus, thereby providing additional anchoring for the stent 10.

In addition to retaining arches 16a, 16b, 16c, the stent 10 further comprises auxiliary arches 18a, 18b, 18c, which likewise exert a radially-acting contact force against the wall of the blood vessel in the implanted state of stent 10, thereby further improving anchoring of stent 10 at the site of implantation.

As can be seen from FIG. 1b, stent 10 comprises a total of three essentially U-shaped or V-shaped auxiliary arches 18a, 18b, 18c which are closed towards the lower end 2 of said stent 10. Each auxiliary arch 18a, 18b, 18c connects a first retaining arch 16a, 16b, 16c with a second retaining arch neighboring the first retaining arch.

In a top plan view of the lower end region 2 of the expanded stent 10 (cf. FIG. 1c), the lower end region 2 exhibits a dodecagonal polygonal structure formed from the individual arms 16a', 16a", 16b', 16b", 16c', 16c" of retaining arches 16a, 16b, 16c and the individual arms 18a', 18a", 18b', 18b", 18c', 18c" of the auxiliary arches 18a, 18b, 18c. This stent design particularly provides a total of six arches 16a, 16b, 16c, 18a, 18b, 18c uniformly distributed around the lower end region 2 of stent 10, each of which press against the vascular wall and effectively hold the stent 10 in position in the expanded and implanted state of stent 10.

To recapitulate, providing retaining arches 16a, 16b, 16c on the one hand and auxiliary arches 18a, 18b, 18c on the other results in a radial force being exerted on the vascular wall by the respective lower end portions of these arches. This ensures both a secure seal of a valvular prosthesis 100 affixed to stent 10 relative the vascular wall, as well as a secure anchoring of the stent 10, at the site of implantation in the heart.

In addition to the contact force exerted on the vascular wall by way of the retaining arches 16a, 16b, 16c and auxiliary arches 18a, 18b, 18c, it is conceivable for the upper end region 3 of stent 10 to expand radially 10% to 25% more—in the expanded state of stent 10—compared to the lower end region 2. This gives the stent 10 a slight concave structure which tapers towards the lower end region 2. This ensures secure anchoring of the stent 10 within the vessel by the upper end region 2 of the stent 10 pressing against the vascular wall.

To ensure that minimal longitudinal displacement of a valvular prosthesis affixed to stent 10 can occur relative stent 10, even during the peristaltic movement of the heart and the blood vessel in which stent 10 is deployed, the embodiment of the inventive stent 10 depicted in the drawings provides for the stent 10 to comprise a plurality of fastening portions 11 extending in the longitudinal direction L of stent 10, by means of which a valvular prosthesis 100 is affixed to the stent 10. Reference is made to FIG. 1d which shows a perspective side view of an endoprosthesis 1 for treating a narrowed cardiac valve or a cardiac valve insufficiency. The endoprosthesis 1 comprises the stent 10 pursuant the first embodiment of the invention holding a valvular prosthesis 100. The valvular prosthesis 100 comprises at least one valve flap 102 made from a biological or synthetic material.

It will be appreciated that the valvular prosthesis may be made from any suitable material, including biological valves removed from animals such as pigs and horses, man-made biological valves created from connective tissue such as pericardium, tissue grown from cell cultures, and man-made materials and fabrics such as nitinol.

In detail, the first connecting webs 17 of stent 10 connect with connecting portions 22 via their upper ends 17d and with the upper ends 13 of fastening portions 11 via their lower ends 17p. The respective lower ends 14 of the fastening portions which are connected to one and the same connecting web 17 are thereby connected together via an essentially U-shaped or V-shaped auxiliary arch 18a, 18b, 18c which is closed towards the lower end 2 of stent 10.

Specifically, the first embodiment of the inventive stent 10 is shown in FIG. 1d in its expanded state, whereby a valvular prosthesis 100 is fastened to said stent 10 by means of a thread 101 or a thin wire and stretched by the stent 10. It is easily recognized that the widening of the centre area and the lower end region 2 of stent 10 at which the valvular prosthesis 100 is disposed achieves spreading of the valvular prosthesis. At the same time, the lower end portions of the retaining arches 16a, 16b, 16c and the auxiliary arches 18a, 18b, 18c exert a radial force on the (not shown in FIG. 1d) vascular wall.

As can be seen from FIG. 1d, a defined plurality of fastening holes 12 are configured in the respective fastening portions 11 of stent 10, and are arranged to be distributed at predefined longitudinal positions along the fastening portions 11. The thread 101 or thin wire with which the valvular prosthesis 100 is attached to stent 10 is guided through each respective fastening hole 12.

Both components constituting the endoprosthesis 1, namely the stent 10 and the valvular prosthesis 100, are preferably not connected together until directly prior to the surgical procedure. This is of advantage in terms of transport and storage since the stent 10 is a relatively sturdy component mechanically and can be stored for a long period of time without degradation. This is particularly true when the stent 10 is stored in its second shape; i.e. in the expanded state, and not brought into its first (collapsed) shape until directly prior the surgical procedure.

It can be noted from FIGS. 1b and 1d that the respective fastening portions 11 are configured in the respective arms 16a', 16a", 16b', 16b", 16c', 16c" of retaining arches 16a, 16b, 16c of stent 10. The size of the fastening holes 12 configured in the fastening portions 11 should be adapted to the thickness of the thread 101 or wire used to fasten the valvular prosthesis 100 to the stent 10.

The cross-sectional shape to the fastening holes 12 may also be adapted to the cross-sectional shape of the thread 101 or wire used to fasten the valvular prosthesis 100. This allows fixing of the valvular prosthesis 100 to the stent 10 at a precise predefined position relative to the stent 10. By providing of a plurality of fastening holes 12 to anchor the valvular prosthesis 100 to the stent 10, precise positioning of the valvular prosthesis on stent 10 is achieved.

Because the fastening holes 12 are adapted to the thickness and/or the cross-sectional shape of the thread 101 or wire used to affix the valvular prosthesis 100 to the stent 10, relative movement between the stent 10 and the valvular prosthesis 100 due to the peristaltic motion of the heart can be effectively prevented when the endoprosthesis 1 is implanted. The valvular prosthesis 100 is thus fastened to the stent 10 with minimal play, based on which friction-induced wear of the thread 101 or wire used to affix the valvular prosthesis is minimized. As shown in the figures the fastening holes 12 have a circular cross-sectional shape.

As already mentioned, the fastening holes 12 configured in the respective fastening portions 11 may be of different diameters, numbers or cross-sectional shapes (oval, square, etc) according to the diameter of a thread 101 used for affixing the valvular prosthesis 100 to the stent 10, and/or according to the sewing technique utilized for affixing the valvular prosthesis 100 to the stent 10. The diameter, number and/or cross-sectional shape of at least one of the fastening holes 12 may also serve as an indication of the type of the endoprosthesis 1, i.e. the medical device used in the treatment of a narrowing of a cardiac valve and/or a cardiac valve insufficiency. In this respect, the diameter, number and/or cross-sectional shape of the at least one fastening hole 12 may be used for identification to differentiate between different sizes or types of valvular prostheses 100 adapted to be fixed on the stent 10, or may be used for identification to differentiate between different sizes or types of endoprostheses 1, if a valvular prosthesis 100 is already fixed to the stent 10. For example, a small-sized stent 10 having a small-sized valvular prosthesis 100 fixed thereto or a small-sized stent 10 adapted and configured for carrying a small-sized valvular prosthesis 100 could have circular fastening holes 12 whilst a large-sized stent 10 having a large-sized valvular prosthesis 100 fixed thereto or a large-sized stent 10 adapted and configured for carrying a large-sized valvular prosthesis 100 may have triangular fastening holes 12. This allows the surgeon/cardio staff to easily and visually tell different valve sizes, stent types and/or types of the endoprosthesis apart without the need to measure.

The fastening portions 11 of the stent 10 (onto which the valvular prosthesis 100 is sewn or sewable) do not change their shape when the stent 10 is compressed, e.g. when the stent 10 is in its first (collapsed) shape shown in FIG. 1a. This phenomenon occurs when standard tube stents are used. Thus the risk of thread wear is minimal.

A stent 10 in accordance with a second embodiment is depicted in FIGS. 2a to 2c and is similar in structure and function to the first embodiment of the stent 10 depicted in FIGS. 1a to 1c. The same also holds true for the cutting pattern depicted in FIG. 2e which is, in principle, comparable to the cutting pattern according to FIG. 1e. A detailed description of the common features will therefore not be provided.

A difference to be seen is in the configuration of the catheter retaining means 23 provided at the distal end 3 of stent 10. In contrast to the first embodiment of the inventive stent 10, heads of an essentially round configuration are used as catheter retaining means 23 in the second embodiment, in each case provided with essentially oval eyelets 24. Due to the round configuration of the heads the risk of producing injury or damage is lowered. Hence, an essentially round configuration of the heads is more atraumatic.

As already indicated, the stent 10 according to certain embodiments of the present invention preferably exhibits a structure integrally cut from a portion of tube, and in particular from a small metal tube. A fastening arch 19a, 19b, 19c and a retaining arch 16a, 16b, 16c is allocated to each positioning arch 15a, 15b, 15c, and each retaining arch 16a, 16b, 16c is connected to a neighboring retaining arch by means of an auxiliary arch 18a, 18b, 18c. A fastening portion 11 with a specific number of fastening holes 12 is configured in each arm 16a', 16a'', 16b', 16b'', 16c', 16c'' of retaining arch 16a, 16b, 16c.

FIGS. 1e and 2e each show a two-dimensional projection of a cutting pattern which can be used in the manufacture of the stent 10 pursuant the first or second embodiment of the invention. This enables a one-piece stent 10 to be cut from a portion of tube, in particular a small metal tube. It is evident that, on the one hand, the inventive stent 10 dispenses with fixed-body joints or other similar connective devices between the individual components of stent 10 (positioning arch, retaining arch, auxiliary arch). On the other hand, a stent 10 is provided which exhibits, with minimum longitudinal extension, the functionality of positionability as provided by the positioning arches 15a, 15b, 15c on the one hand and, on the other, the functionality of the defined fastening of a valvular prosthesis 100, as provided by the fastening portions 11 configured in the respective arms 16a', 16a'', 16b', 16b'', 16c', 16c'' of the retaining arch 16a, 16b, 16c.

In addition to its retaining arches 16a, 16b, 16c, the stent 10 further comprises auxiliary arches 18a, 18b, 18c which enable a particularly secure anchoring of stent 10 in the site of implantation in the heart.

A stent 10 according to a third embodiment of the invention also has a one-piece structure cut from a portion of a tube, in particular from a small metal tube. The cutting pattern used to form the stent design is shown in a two-dimensional projection in FIG. 3.

The differences between the third embodiment of the stent and the first or second embodiments can be seen by referring to the two-dimensional cutting pattern shown in FIG. 3. As is also the case in the first or second embodiment, the third embodiment of the stent 10 has a total of three positioning arches 15a, 15b, 15c, which undertake the function of automatic positioning of the cardiac valve stent in the plane of the pulmonary valve or the aortic valve.

The stent 10 is made from nitinol and positioning arches 15a, 15b, 15c are programmed during manufacture, by a suitable heat treatment of the positioning arches 15a, 15b, 15c, so that, in the stent's expanded state i.e. when the permanent shape has been assumed after exceeding the switching temperature, the positioning arches not only spread apart in a radial direction, as illustrated in FIGS. 1b, 1d and 2b, 2d, but simultaneously curve in a slightly convex manner in the direction of the stent 10. This measure makes it possible for the head portions 20 of the positioning arches 15a, 15b, 15c to lie parallel with the longitudinal axis L of the expanded stent 10 in an ideal manner. As a result, during the implantation of the cardiac valve stent 10, the head portions 20 of the positioning arches 15a, 15b, 15c can be inserted particularly easily into the pockets T of the native heart valve H (see FIG. 12a). In particular, this minimizes damage to surrounding tissue when the positioning arches 15a, 15b, 15c are inserted into the pockets T of the native heart valve H. The shape also allows the positioning arches 15a, 15b, 15c to exert an additional clipping force on the native valve leaflets by pinching the native leaflet at the bottom of each arch.

In addition, the convex curvature of the positioning arches 15a, 15b, 15c enables an especially secure support of the stent 10 at the implantation site since the positioning arches 15a, 15b, 15c are better adapted to the anatomy of the pockets T of the native heart valves H and their surroundings.

As in a stent 10 according to the first and second embodiment (see for example FIGS. 1b, 1c, 1d and 2b, 2c, 2d), a stent 10 of the third embodiment, has catheter retaining means 23 with eyelets 24. As with previously described embodiments, a suitable catheter system can be releasably coupled to the catheter retaining means 23 to facilitate a minimally-invasive, transvascular implantation and explantation of the stent 10.

As with the stent 10 of the first or second embodiment, the retaining arches 16a, 16b, 16c and auxiliary arches 18a, 18b, 18c serve to secure radial fixing of the stent 10 at the implantation site and for stretching a valvular prosthesis fastened to the stent by way of fastening arches 19a, 19b, 19c. No further discussion is needed to explain that the retaining arches 16a, 16b, 16c and the auxiliary arches 18a, 18b, 18c of this embodiment of the stent also function to seal an implanted valvular prosthesis. Similarly, the retaining arches 16a, 16b, 16c and positioning arches 15a, 15b, 15c clamp the native heart valve H like a paperclip and consequently contribute to the secure anchoring of the stent 10 at the implantation site in the heart.

Stent 10 according to the third embodiment differs from the first and second embodiments in that the respective arms 16a', 16a", 16b', 16b", 16c', 16c" of each retaining arch 16a, 16b, 16c extend from the fastening portion 11 to the lower end 2 of the cardiac valve stent and are connected together by means of a connecting portion 30. The connecting portion 30 has a different shape when compared with the U-shaped or V-shaped connecting portions 30 in the embodiments according to FIGS. 1b, 1c, 1d and 2b, 2c, 2d. In particular, the connecting portion 20 has a waist just above the corresponding connecting portion 30' of the fastening arch. The waists in the retaining and fastening arches accommodate an enlarged head 31 at the lower end of each auxiliary arch 18a, 18b, 18c.

Looking at FIG. 3 in detail, each connecting portion 30 which connects the two arms 16a', 16a", 16b', 16b", 16c', 16c" of a retaining arch 16a, 16b, 16c has almost an O-shaped configuration. This shape offers more space for fastening a valvular prosthesis 100 to the stent 10 and also effectively counteracts the occurrence of load peaks which can occur in the implanted state of the endoprosthesis during the transmission of loads between the valvular prosthesis and the stent.

The alternative shape of the connecting portion 30 further increases the effective contact area between the lower end of the retaining arch 16a, 16b, 16c and the vessel wall, when the stent is positioned at the implantation site in its expanded state. Because of this, an improved seal can be obtained between the stent with the valvular prosthesis attached to it and the vessel wall. Furthermore, the radial forces acting in the expanded state of the stent, which are transmitted via the retaining arches 16a, 16b, 16c to the vessel wall, are distributed over a discrete contact area, thereby counteracting the occurrence of load peaks. The risk of damage from the retaining arches 16a, 16b, 16c to the vessel wall is also reduced.

Each connecting portion 30' which connects the two arms 19a', 19a", 19b', 19b", 19c', 19c" of a fastening arch 19a, 19b, 19c has a more angular shape that assists with anchoring of a valvular prosthesis 100 to the stent 10.

The alternative shapes of the closed ends of the retaining and fastening arches (16, 19) accommodates the enlarged heads 31 of shortened auxiliary arches 18a, 18b, 18c. The enlarged head 31 enables the auxiliary arches to be used to support the valve material 100, as well as providing additional radial force. The heads 31 include fastening holes 12 for additional attachment of the prosthetic valve 100 which further stabilizes the prosthetic valve 100 attached to the stent. The additional fastening holes 12 also reduce the likelihood of mis-aligning the valve 100 within the stent 10 and minimize any longitudinal movement of the valve 100 once the endoprosthesis 1 has been implanted. In addition and as already discussed in relation to the retaining arches 16a, 16b, 16c, an enlarged contact area is provided with the widened head portions 31, which improves the anchorage of the stent 10 at the implantation site while minimizing the risk of damage to the vessel wall.

As can be seen from the cutting pattern of FIG. 3, the upper arm portions of the respective retaining arches 16a, 16b, 16c are connected to the lower region 14 of the associated fastening portion 11, while the upper arm portions of the auxiliary arches 18a, 18b, 18c are connected to the central region of the associated fastening portion 11. In this way, it is possible to form secure connections between the arms 16a', 16a", 16b', 16b", 16c', 16c" of the retaining arches 16a, 16b, 16c, and between the arms 18a', 18a", 18b', 18b", 18c', 18c" of the auxiliary arches 18a, 18b, 18c and the fastening portion 11 without having to enlarge the overall size of the stent 10.

A yet further difference between the stent of the third embodiment and the stents of the first and second embodiments is the inclusion of notches 26. As shown in FIG. 3, the notches 26 are located at the lower end of the fastening portion 11 and are formed in the arms of the auxiliary arches 18a, 18b, 18c and the retaining arches 16a, 16b, 16c. To ensure the strength of the stent is maintained, the notches are shaped in the arms rather than being cut out of the arms. The notches 26 function as additional guides and anchoring points for suture thread or wire.

To accommodate the notches 26, the auxiliary arches 18a, 18b, 18c extend from the fastening portion 11 mid-way along the length of the fastening portion 11, rather than from the lower end of the fastening portion 11. This provides each auxiliary arch 18a, 18b, 18c with sufficient flexibility that would otherwise be lacking from a shorter auxiliary arch.

FIG. 4 shows a two-dimensional projection of a cutting pattern suitable for the manufacture of a stent 10 according to a fourth embodiment of the invention.

The fourth embodiment of the stent 10 is similar to the third embodiment. However, the stent of the fourth embodiment includes additional fastening holes 12a provided for fastening a valvular prosthesis. Specifically, the additional fastening holes 12a are at the lower end 17p of the first connecting webs 17. The additional fastening holes 12a are configured as eyelets on the first connecting webs 17 between the fastening portion 11 and the connecting portion 22. It is of course conceivable that the additional fastening holes 12a are not configured as eyelets but are directly formed in the first connecting webs. The additional fastening holes 12a enable the upper region of a valvular prosthesis to be additionally secured to the stent 10.

The size of the additional fastening holes 12a may be adapted to the thickness of particular thread or wire used to fasten the valvular prosthesis to the stent 10. The cross-sectional shape of the additional fastening holes 12a may also be adapted to the cross-sectional shape of the thread or wire used for fastening the valvular prosthesis. Due to the presence of a number of additional fastening holes 12a for fixing the valvular prosthesis to the cardiac valve stent, the fastening position of the valvular prosthesis to the cardiac valve stent can be precisely defined.

As an alternative to fastening holes 12a, the same region of the stent 10 may be provided with one or more additional notches. These notches perform the same function as the fastening holes 12a and assist with additional anchoring of a prosthetic valve within the stent 100.

A stent 10 according to the fifth embodiment of the invention is shown in FIGS. 5a-c with the stent 10 in its expanded state. FIGS. 5a and 5b show side views of the stent 10, while FIG. 5c shows a plan view on the upper end 3 of the stent 10. FIG. 5d shows a two-dimensional projection of a cutting pattern suitable for the manufacture of a stent according to the fifth embodiment of the invention, the stent being cut integrally from a portion of tube, in particular a small metal tube.

The stent 10 according to the fifth embodiment is comparable in structural and functional respect to the stent of the third embodiment. In particular, the stent 10 of the fifth embodiment similarly has a total of three positioning arches 15a, 15b, 15c, which again undertake the function of automatic positioning of the stent 10 in the plane of the valve of the pulmonary valve or the aortic valve. As in other embodiments of the stent 10, the positioning arches 15a, 15b, 15c have a radiused head portion 20, which engages in the pockets of the (insufficient) heart valve H being treated during positioning of the stent 10 at the implantation site in the heart (see FIG. 12a).

A total of three retaining arches 16a, 16b, 16c and three fastening arches 19a, 19b, 19c are also provided.

The fifth embodiment stent 10 differs from the stent of the third embodiment in that further notches 26a are provided in addition to the fastening holes 12 in the fastening portion 11. As can be seen in FIG. 5d, a series of notches 26a are provided which serve as additional anchoring means for the prosthetic valve 100 and guides for the suture thread or wire. These additional notches 26a also minimize movement of the suture thread or wire thereby reducing wear on the thread or wire by rubbing on the first connecting web 17 when the endoprosthesis 1 is implanted. The additional notches 26a also ensure that the upper region of a valvular prosthesis can be fastened firmly to the cardiac valve stent 10 allowing minimal movement of the prosthesis thereby further minimising the likelihood of wear induced by friction on the suture thread or wire.

It is conceivable of course that the additional notches 26a are adapted to the thickness of the suture thread or wire. In particular, the additional notches 26a may be radiused to minimise damage to the suture thread or wire.

The fifth embodiment of the stent 10 also includes radial arches 32a, 32b, 32c extending from the positioning arches 15a, 15b, 15c towards the upper end 3 of the stent 10. As is shown most clearly in FIGS. 5a and 5b, the stent 10 has three radial arches 32a, 32b, 32c, with each arch 32a, 32b, 32c located between the two arms 15a, 15a', 15b, 15b', 15c, 15c' of each positioning arch 15a, 15b, 15c. Each radial arch 32a, 32b, 32c has a shape that is roughly inverse to each positioning arch 15a, 15b, 15c and extends in the opposite direction to each one of the positioning arches 15a, 15b, 15c.

As can be seen in particular in the cutting pattern shown in FIG. 5d, each arm 32', 32" of a radial arch 32 merges at about the mid-point of the length of the stent 10 into an arm 15a', 15a", 15b', 15b", 15c', 15c" of an opposing positioning arch 15a, 15b, 15c.

The two arms 32', 32" of each radial arch 32a, 32b, 32c are connected together at the upper end 3 of the stent 10 by means of a radiused connecting portion or head 33. This head 33 is not only radiused but also widens at the tip so that the head 33 abuts against the interior wall of the vessel over as large a contact area as possible when the stent 10 is in its expanded and implanted state.

The heads 33 of each radial arch 32a, 32b, 32c also serve as additional means by which the stent 10 may be retained in a catheter before and during implantation and/or to recapture the stent after implantation.

FIG. 5c shows a perspective plan view from the upper end 3 of the stent 10 and illustrates that the radial arches 32a, 32b, 32c are programmed so that they extend in a radial direction outside the circumference of the stent 10 when the stent 10 is in its expanded state. In this way an increased contact force can be applied to the vessel wall by the upper end region of the stent 10. This, in turn, allows an increased security in the fixing of the stent 10 in situ, thereby reducing the likelihood of migration of the stent. Therefore, in its expanded state, in addition to the clamping effect of the positioning arches, the stent 10 of the fifth embodiment is secured in place on implantation via radial forces exerted by the retaining arches 16a, 16b, 16c, the auxiliary arches 18a, 18b, 18c and the radial arches 32a, 32b, 32c, all of which project outwards in a radial direction from the circumference of the stent 10.

It can be seen from the cutting pattern shown in FIG. 5d that the radial arches 32a, 32b, 32c do not project in the longitudinal direction L of the stent 10 beyond the plane in which the catheter retaining means 23 or the fastening means with fastening eyelets 24 are situated. This ensures that the catheter retaining means 23 can co-operate with corresponding means within a suitable implantation catheter without interference from the heads 33 of the radial arches 32a, 32b, 32c. Indeed, as explained above, the heads 33 themselves can be used as additional catheter retaining means or additional means to effect explanation of the stent 10.

In principle, the stent 10 may have more than three radial arches 32 in order to increase the radial contact force further. It is also possible to provide barb elements on all or some of the radial arches 32a, 32b, 32c, for example, to allow a still better anchoring of the stent 10 at the implantation site.

A stent 10 according to a sixth embodiment of the invention is shown in FIGS. 6a-d and FIGS. 6f-i. FIGS. 6a-c show various perspective side views the stent 10 in its expanded state while a two-dimensional projection of a cutting pattern suitable for the manufacture of the stent according to the sixth embodiment is shown in FIG. 6d.

FIG. 6e shows a perspective side view of an endoprosthesis for treating a narrowed cardiac valve or a cardiac valve insufficiency, where the endoprosthesis comprises a cardiac valve stent which is similar to the sixth embodiment of the invention for holding a valvular prosthesis. In detail, FIG. 6e shows a valvular prosthesis 100 attached to a stent 10 as an example on how to fix a valvular prosthesis 100 to a stent 10. This example is applicable to the stent embodiments described herein.

Figure 6A:
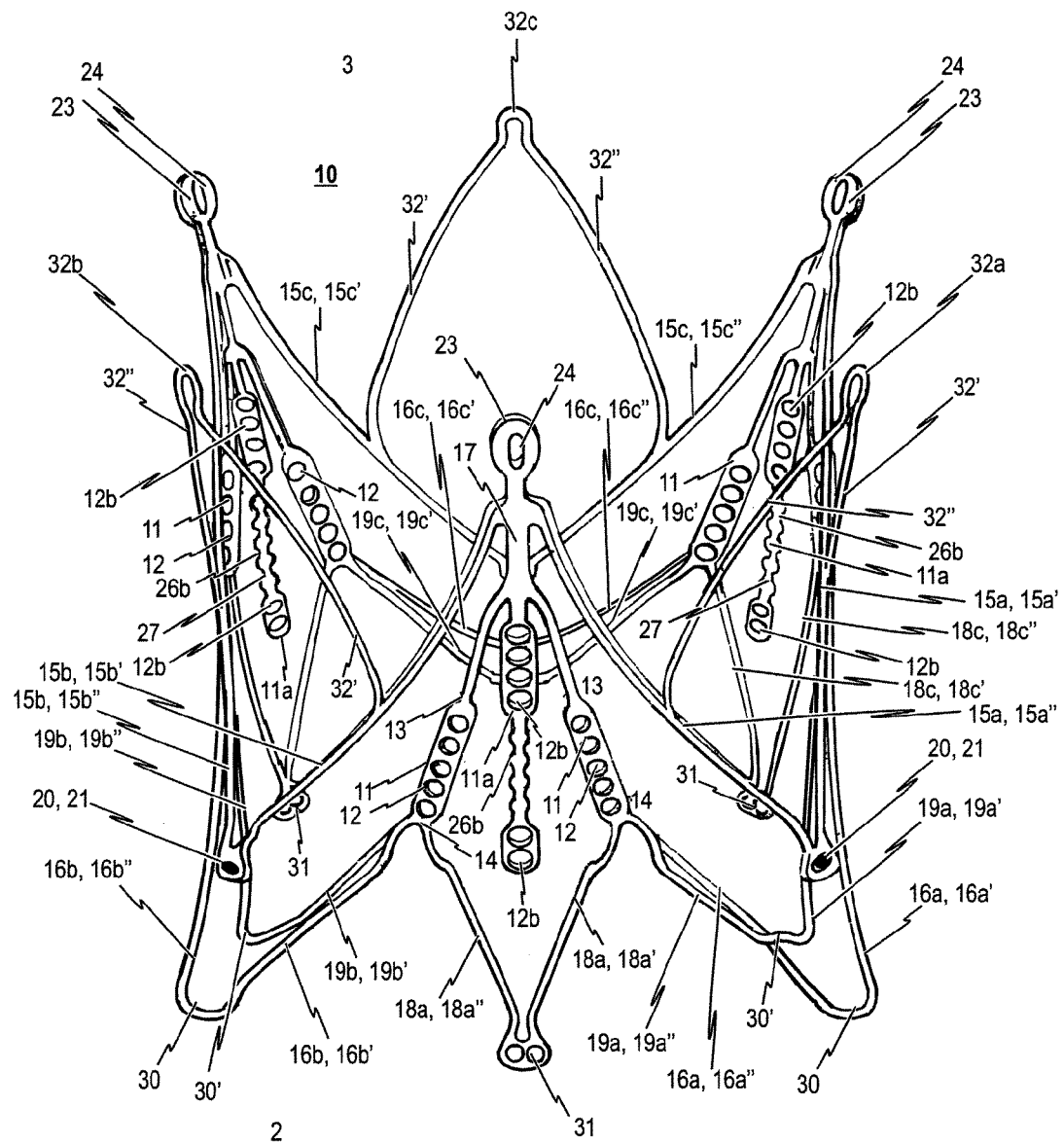
FIG. 6f show a perspective side view of an endoprosthesis for treating a narrowed cardiac valve or a cardiac valve insufficiency, where the endoprosthesis comprises the cardiac valve stent according to the sixth embodiment of the invention for holding a valvular prosthesis.
FIGS. 6g and 6h show various perspective detail views of the endoprosthesis shown in FIG. 6f.
FIG. 6i shows a top view of the lower end of the endoprosthesis shown in FIG. 6f.
Figure 6B:
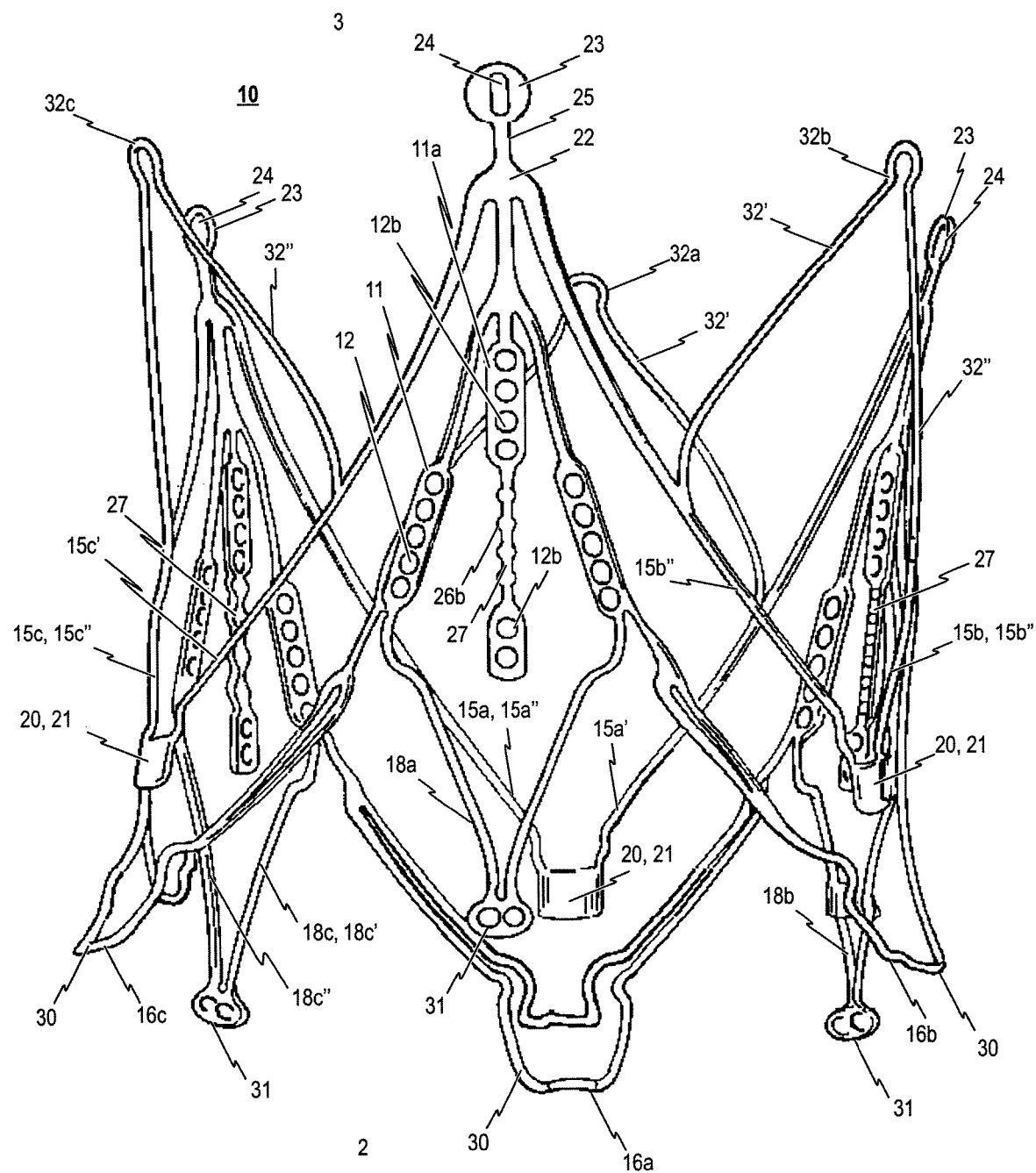
Figure 6C:
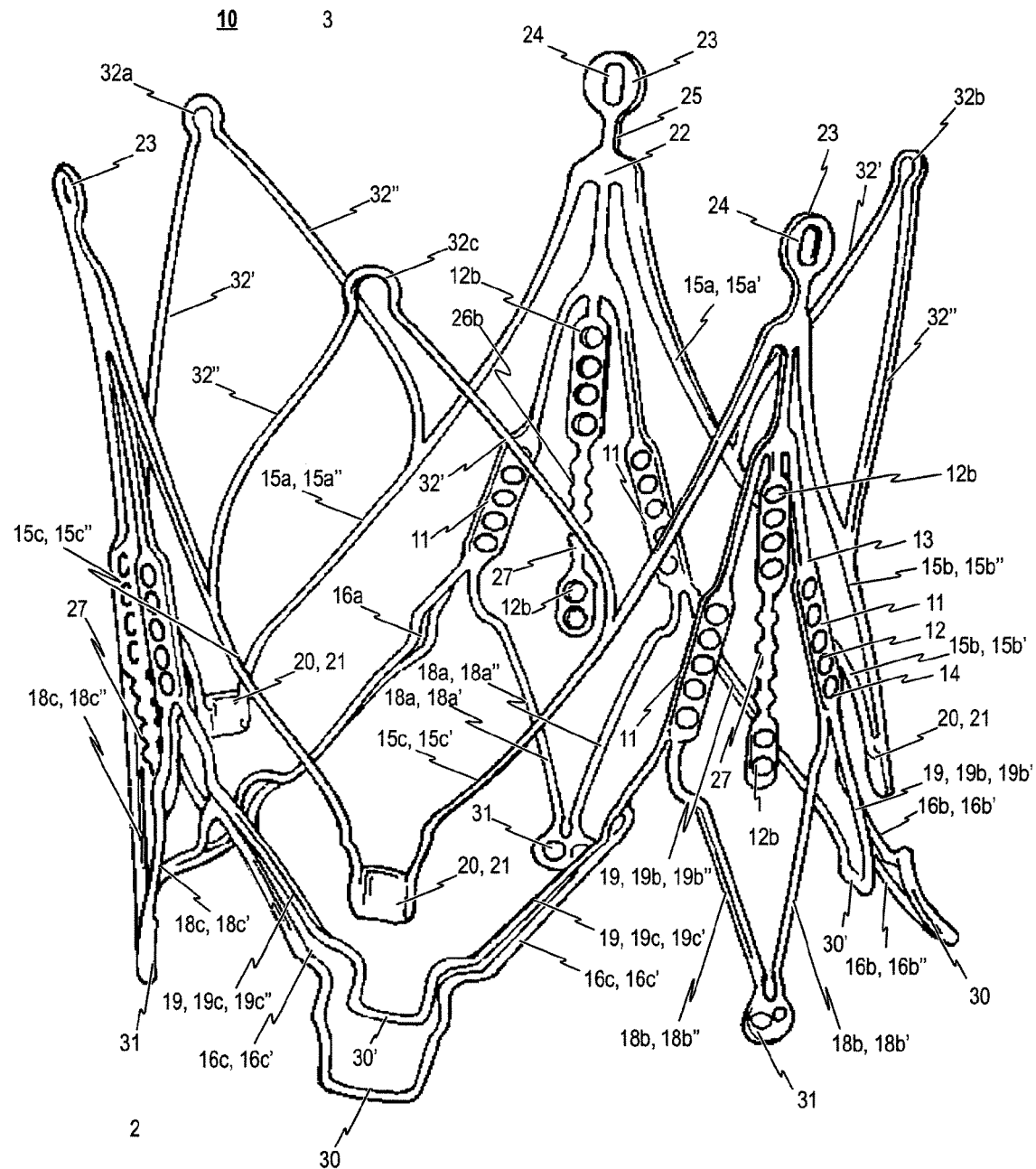
Figure 6D:
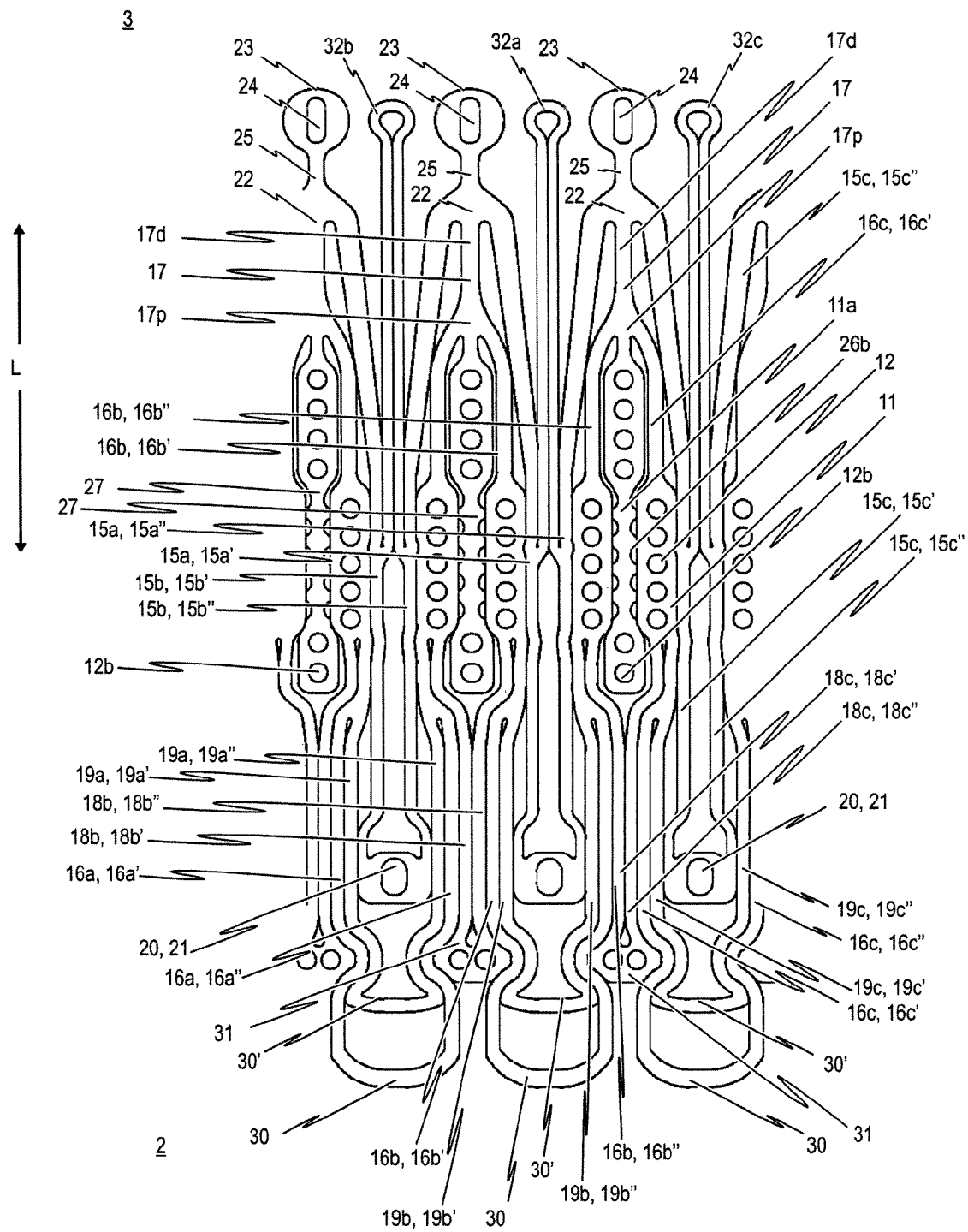

As in the embodiments previously described, the stent 10 of the sixth embodiment is again configured as a one-piece structure cut from a portion of tube, in particular from a small metal tube, the cutting pattern being shown as a two-dimensional projection in FIG. 6d.

The sixth embodiment of the stent 10 is in principle similar in structure and function with respect to the fifth embodiment. To avoid repetition, reference is therefore made to the above description of the fifth embodiment. In particular, essentially U-shaped or V-shaped radial arches 32a, 32b, 32c are likewise provided to increase the radially acting contact force in the upper region of the stent 10.

The sixth embodiment differs from the fifth embodiment in that fixing bridges 27 with additional fastening portions 11a are provided for additional fastening of a valvular prosthesis or parts of a valvular prosthesis. The presence of fixing bridges 27 with additional fastening portions 11a is a particular advantage when a valve constructed from a sheet of biological material, such as pericardium, is used as a valvular prosthesis, i.e. a valvular prosthesis which is made up of several pieces of material. When pericardial valves are used, care must be taken to ensure that the pericardial material can be securely attached to the stent 10. For this reason, the stent 10 according to the sixth embodiment has a total of three fixing bridges 27 each comprising additional fastening portions 11a. Each fixing bridge 27 is attached to one of the first connecting webs 17 and extends in the direction of the lower end 2 of the stent 10.

The additional fastening portions 11a provided on the fixing bridges 27 have yet more fastening holes 12b and/or other fastening means, for example notches 26b, to anchor a thread or a thin wire which is used to fastened the pericardial material or the valvular prosthesis to the stent 10 allowing minimal, preferably no, movement of the valvular prosthesis. It is of course conceivable to provide fastening holes or fastening eyelets, the diameter of which is adapted to the thickness of the thread or wire used for fastening the valvular prosthesis. In general, the fastening holes 12b or notches 26b should be radiused to minimize wear of the thread or the wire induced by friction so far as is possible.

Figure 6E:
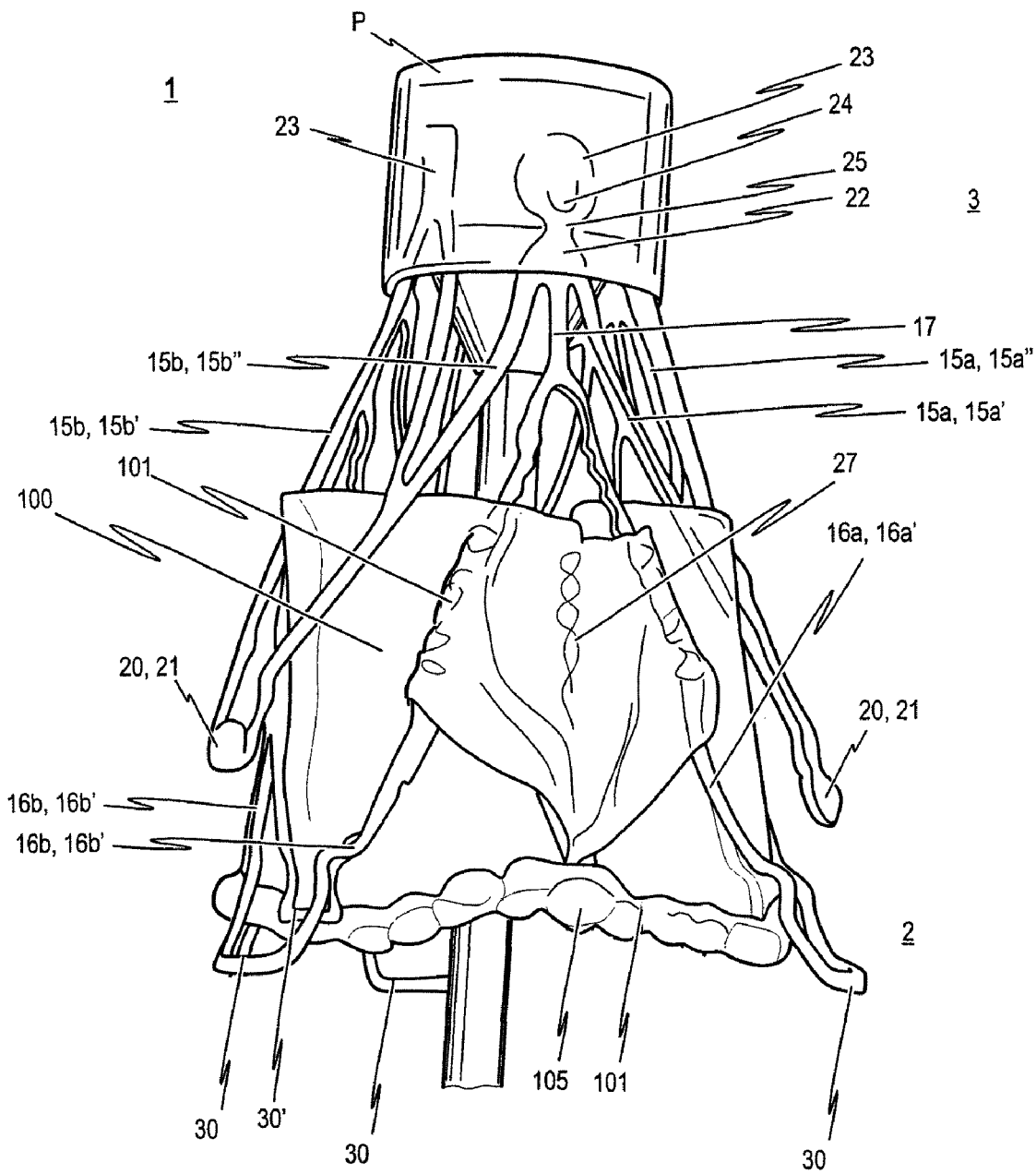
Figure 6F:
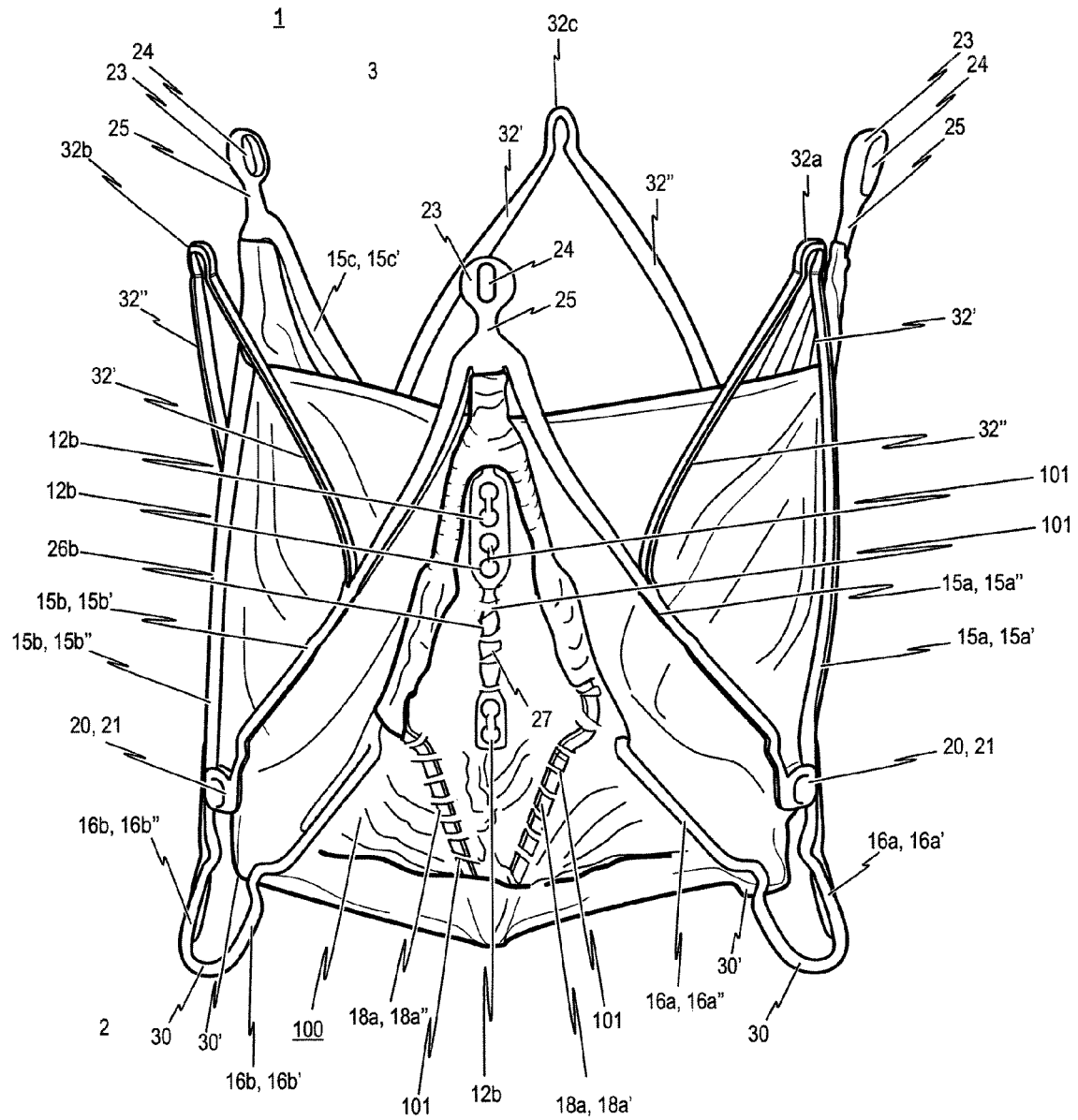

Reference is made to FIGS. 6e and 6f which show perspective side views of an endoprosthesis 1 for treating a narrowed cardiac valve or a cardiac valve insufficiency. In the embodiment depicted in FIG. 6f, the stent 10 corresponds to a stent pursuant the sixth embodiment of the invention for holding a valvular prosthesis 100. The description of how the valvular prosthesis 100 is fixed to the stent 10 with respect to the sixth embodiment is also applicable to a stent 10 according to the other embodiments described herein.

Figure 6G:
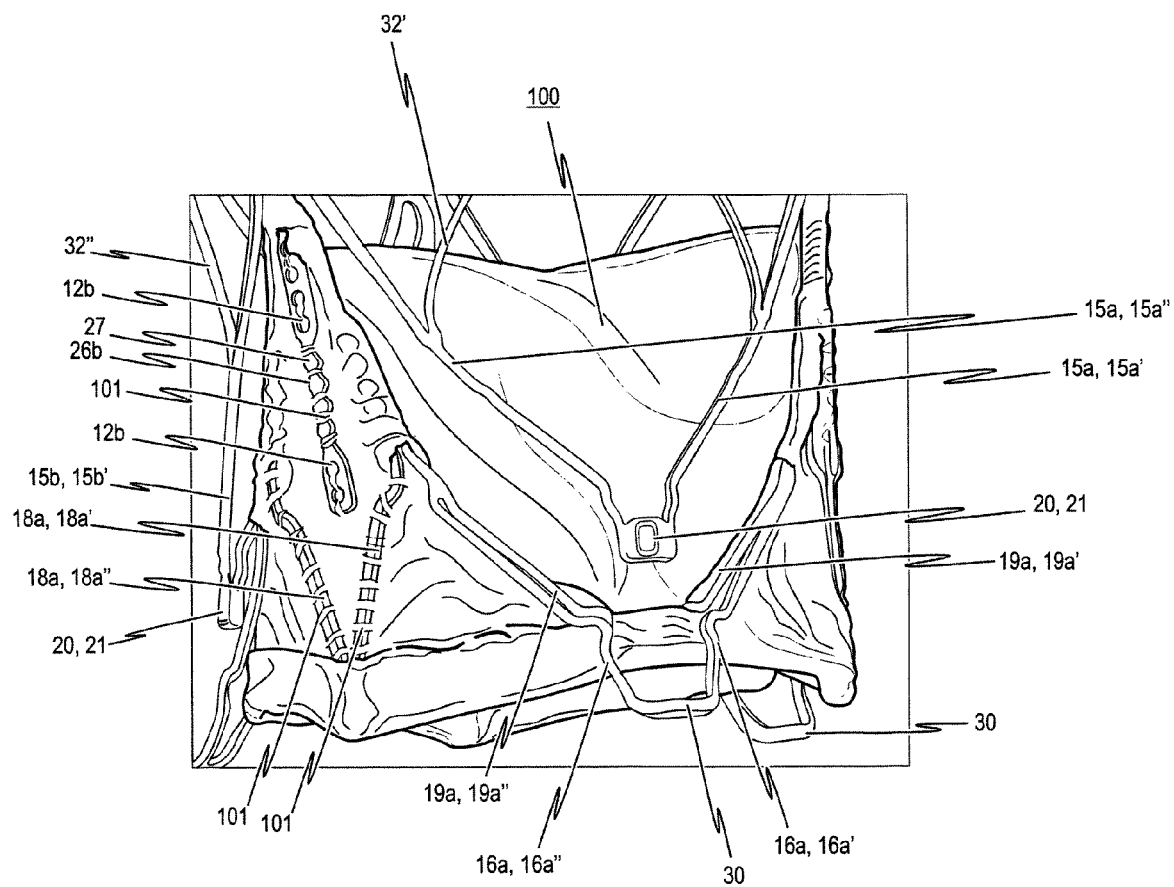
Figure 6H:
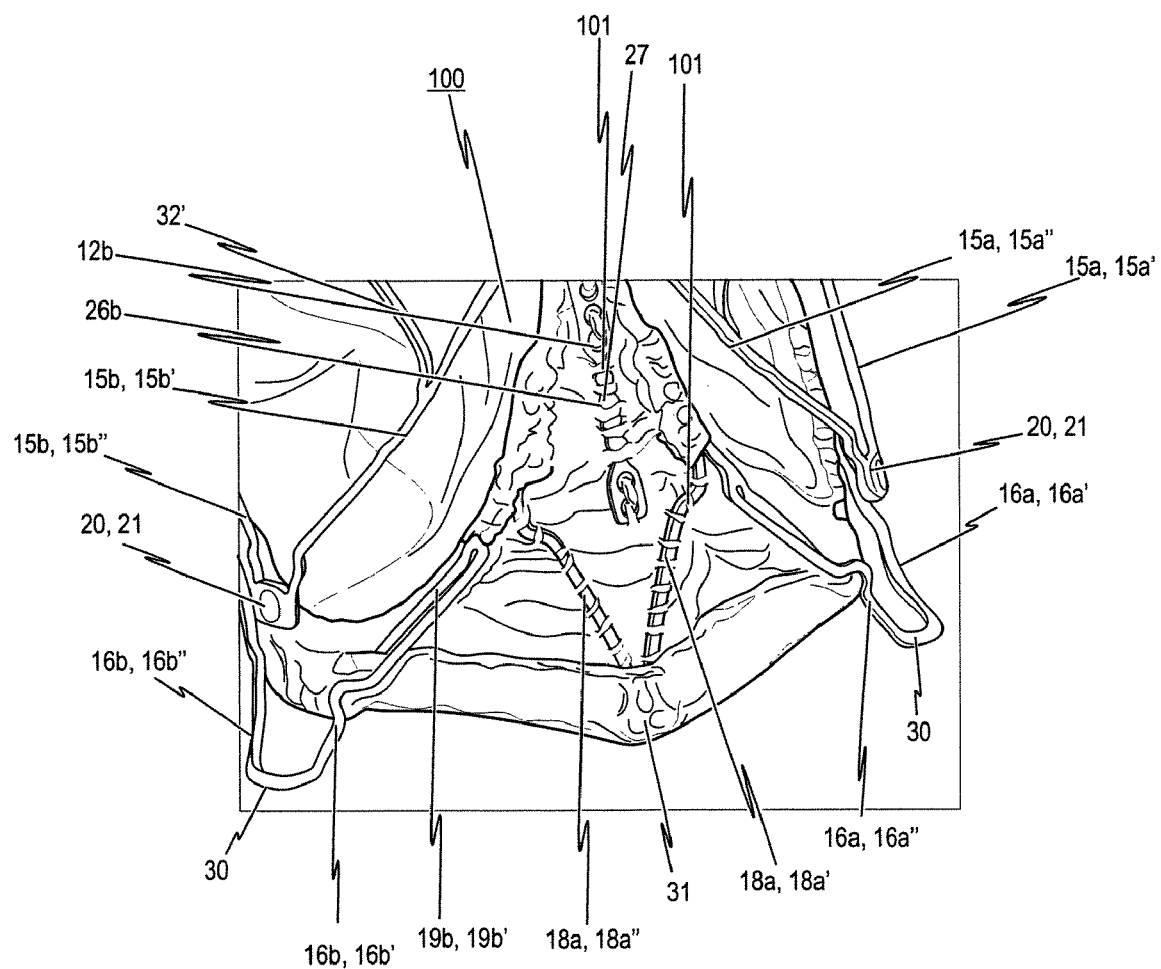
Figure 6I:
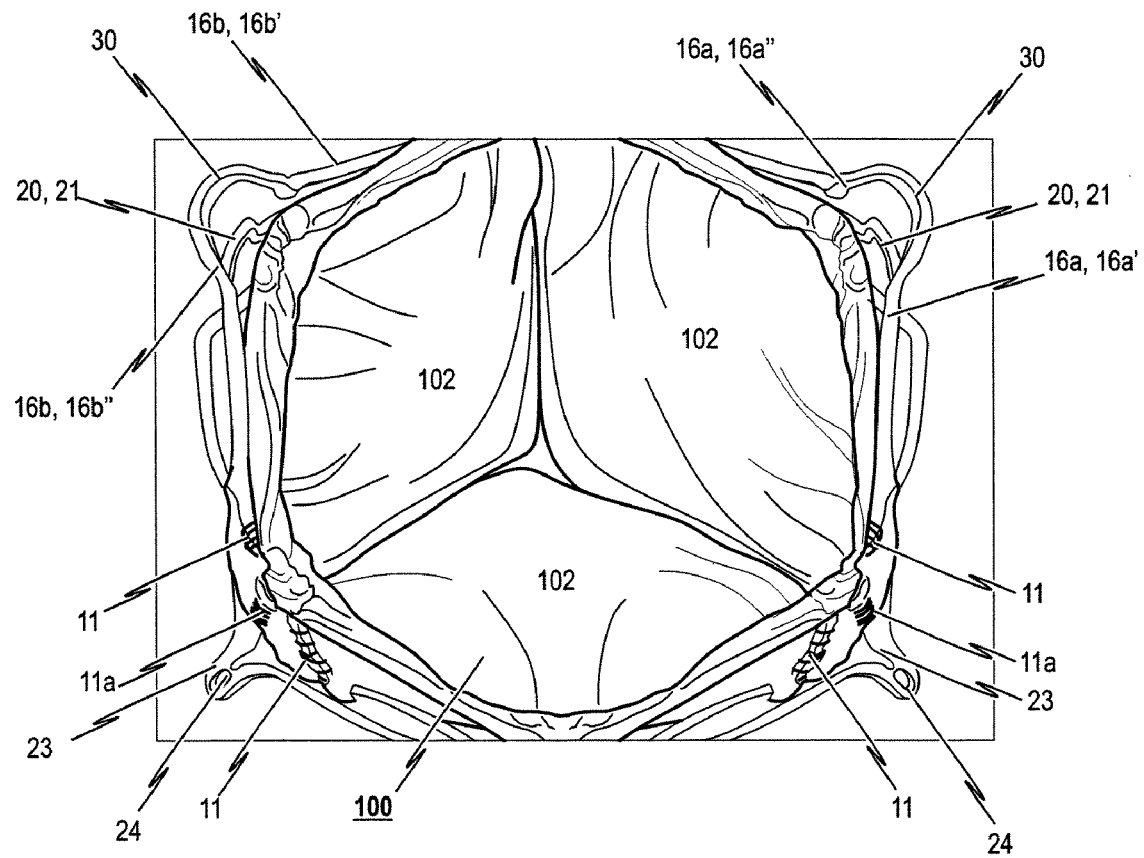

The valvular prosthesis 100 comprises at least one valve flap 102 (see FIG. 6h) made from a biological or synthetic material. In particular, FIG. 6e shows a perspective side view of the endoprosthesis 1, whereby the cardiac stent 10 is shown in a partially expanded state. FIG. 6f shows a perspective side view of the endoprosthesis 1, whereby the cardiac stent 10 is shown in a fully expanded state. FIGS. 6g-i show various perspective detail views of the endoprosthesis 1 depicted in FIG. 6f. In detail, FIG. 6g is a perspective detail view of the head portion 30 of a retaining arch 16a and FIG. 6h is a perspective detail view of an additional fastening portion 11a. FIG. 6i is a top view of the lower end 2 of the endoprosthesis 1 shown in FIG. 6f.

To ensure that minimal longitudinal displacement of the valvular prosthesis 100 affixed to stent 10 can occur relative stent 10, even during the peristaltic movement of the heart and the blood vessel in which stent 10 is deployed, the stent 10 according to the sixth embodiment of the invention comprises a plurality of fastening portions 11 extending in the longitudinal direction L of stent 10. In addition, the stent 100 according to the sixth embodiment is provided with additional fastening portions 11a, each of which is attached to one of the first connecting webs 17 and extends in the direction of the lower end 2 of the stent 10. By means of both the fastening portions 11 and the additional fastening portions 11a the valvular prosthesis 100 is affixed to the stent 10.

In detail, the valvular prosthesis 100 is fastened to the stent 10 by means of a thread 101 or a thin wire which is guided through each respective fastening hole 12, 12b of the fastening portions 11 and the additional fastening portions 11a, respectively. This allows fixing of the valvular prosthesis 100 to the stent 10 at a precise predefined position relative to the stent 10. By providing of a plurality of fastening holes 12 to anchor the valvular prosthesis 100 to the stent 10, precise positioning of the valvular prosthesis 100 on stent 10 is achieved.

Reference is made to FIG. 6e which shows an endoprosthesis 1 with a stent 10 which is a variant of the stent according to the sixth embodiment of the invention. The stent 10 shown in FIG. 6e is not yet fully expanded. An endoprosthesis 1 with a fully-expanded stent 10 according to the sixth embodiment of the invention is shown in FIG. 6f.

The stent 10 according to the present invention is—as will be described in detail below with reference to the illustrations of FIGS. 12a-c—advanced in the collapsed state in minimally-invasive fashion via an insertion catheter system either from the apex cordis (i.e. transapical) or through the femoral artery and the aortic arch (i.e. transfemoral) to the site of implantation at the heart. During the insertion procedure, the stent 10 with the valvular prosthesis 100 affixed thereto is accommodated in the tip K of the catheter system in the collapsed state (cf. FIG. 12a). Upon reaching the site of implantation at the heart, the stent 10 with the valvular prosthesis 100 affixed thereto is sequentially released by the selective manipulating of parts of the catheter tip K.

Figure 12C:
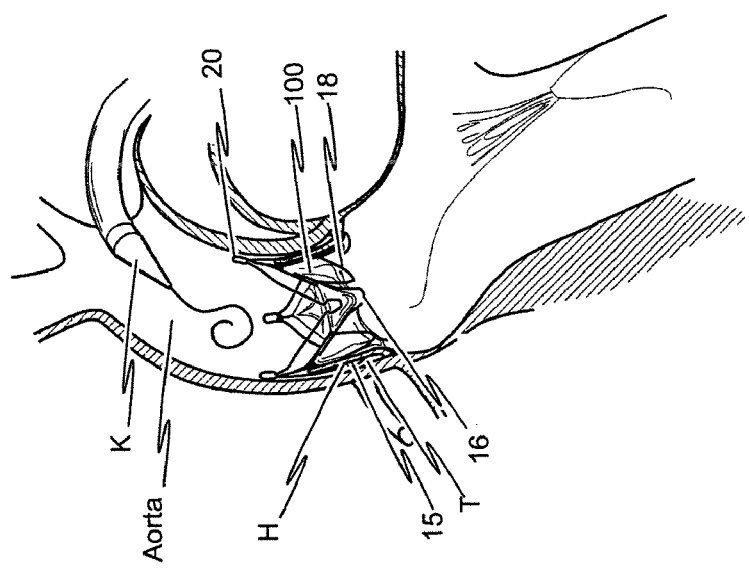
Figure 12B:
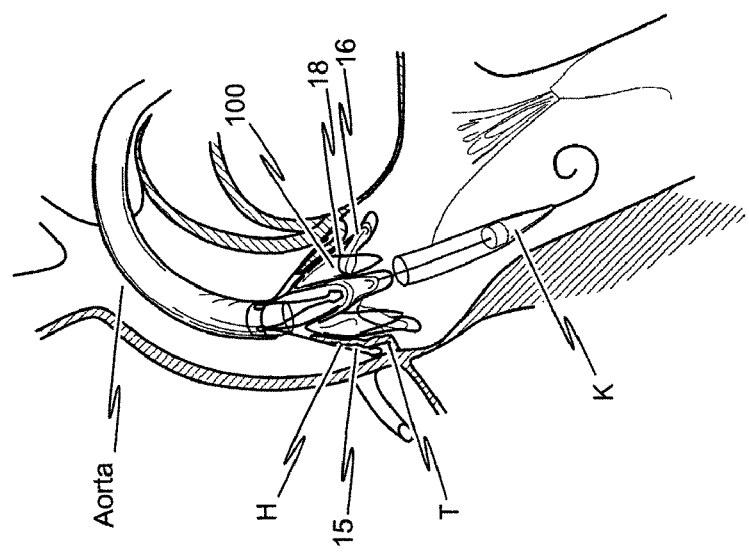
Figure 12A:
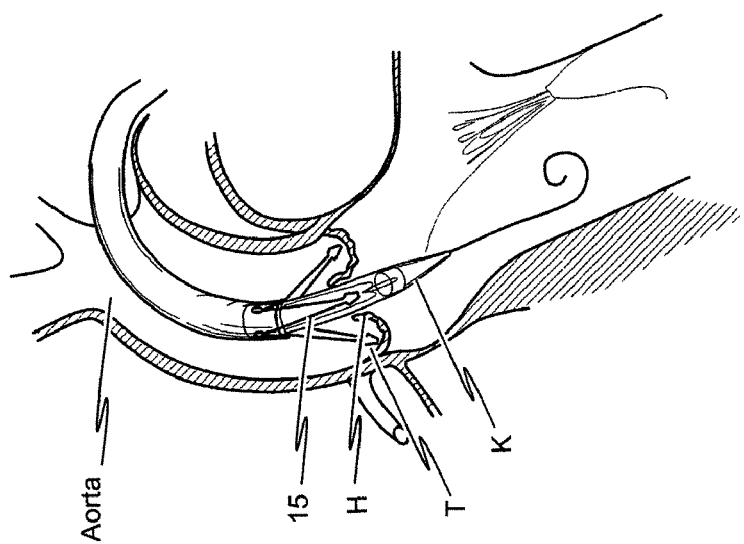

In detail, during a first release step, the catheter tip K of the insertion catheter system is manipulated such that the positioning arches 15a-c of stent 10 are released while the remaining parts of the stent 10, in particular the retaining arches 16a-c, the auxiliary arches 18a-c and the radial arches 32a-c are still in their collapsed state (cf. FIG. 12a). The positioning arches 15a-c released during the first release step expand and spread radially outward. The expanded positioning arches 15a-c can then be inserted into the pockets T of the patient's native cardiac valve H by suitably moving the catheter tip K (cf. FIG. 12a).

In the second release step which follows, the catheter tip K of the insertion catheter system is manipulated such that the arches forming the lower end 2 of the stent 10 (auxiliary arches 18a-c and retaining arches 16a-c) are released while the upper end 3 of the stent 10 is however still firmly affixed to the catheter tip K and is not released (cf. FIG. 12b).

The positioning arches 15a-c disposed on stent 10 and also the retaining arches 16a-c may be curved in convex and arched fashion in the proximal direction; i.e. toward the lower end 2 of stent 10, whereby such a rounded form may reduce injuries to the artery as well as facilitate the unfolding during the self-expansion. Such a design may enable an easier insertion of the positioning arches 15a-c into the pockets of the native cardiac valve without correspondingly injuring the neighboring tissue or blood vessels.

In FIG. 6e, the endoprosthesis 1 exhibiting the stent 10 in accordance with one embodiment of the invention with a valvular prosthesis 100 affixed to said stent 10 is shown in a state after the second release step in which only the upper end 3 with the catheter retaining means 23 is firmly connected to the tip K of the insertion catheter system while the remaining portions of the stent 10 have already been released and radially expanded. It can be seen from the FIG. 6e illustration that due to the self-expansion of the retaining arches 16a-c and the auxiliary arches 18a-c, the valvular prosthesis 100 affixed thereto has already expanded (at least partly).

As shown in FIG. 6e, the distal portion of stent 10 is still accommodated in a sleeve-like portion P within the catheter tip K. This remains the case until the unfolding and positioning of the valvular prosthesis 100 has taken place to the extent that it can be checked for functionality.

If the functional test shows that the valvular prosthesis 100 satisfactorily functions, the sleeve-like portion P can be, as shown in FIG. 12c, distally pushed further in the proximal direction so that also the distal portion of stent 10 with the catheter retaining means 23 is fully released (cf. FIG. 12c).

It can further be seen from the FIG. 6e illustration how the valvular prosthesis 100 can be affixed to the stent 10 by means of threads 101. A pericardial valvular prosthesis 100 is used in the embodiment depicted which is sewn to fastening holes 11a and 11b of a fixing bridge 27 extending between two neighboring retaining arches 16a, 16b. See FIG. 6c and FIG. 6f. The valvular prosthesis 100 may be virtually tubular with a substantially circular cross-section. At the lower end 2 of the stent 10, the valvular prosthesis 100 exhibits a bead 105. This bead 105, which is annular in the top view of endoprosthesis 1, is formed by turning the lower end of the valvular prosthesis 100 inside out by rolling it over on itself. As shown in FIG. 6*e*, the annular bead 105 is overedged by thread 101. The annular bead 105 may be of a different configuration.

The annular bead 105 at the lower end of the valvular prosthesis 100 may provide a secure anchoring of the peripheral area of the valvular prosthesis 100 to the blood vessel in the implanted state of the endoprosthesis 1, even given the peristaltic motion, and thus may provide a secure seal relative the vascular wall.

The annular bead 105 may achieve a secure seal of the valvular prosthesis 100 at the vascular wall despite the basic triangular structure to the stent 10 in a top view of the expanded endoprosthesis 1. When implanting the endoprosthesis 1 in a native blood vessel any leakage between the peripheral area of the annular bead 105 and the vascular wall is sealed by naturally-occurring accretion, in particular calcification. Accordingly, the bead-shaped area 105 provides a secure seal, particularly also during the filling phase of the heart cycle (diastole).

FIG. 6*i* likewise shows a top view of the lower end 2 of the endoprosthesis 1 depicted for example in FIG. 6*f*, whereby the stent 10 for the endoprosthesis 1 is shown in its fully-expanded state.

As shown in FIG. 6*i* the flap segments 102 of the valvular prosthesis 100 are closed in the top view according to FIG. 6*i*, as is the case during diastole of the heart.

As shown in FIGS. 6*f* and 6*g* in detail, the fixing bridges 27 with the additional fastening portions 11*a* also have notches 26*b* to anchor the thread or thin wire which is used to fastened the pericardial material or the valvular prosthesis 100 to the stent 10 allowing minimal, preferably no, movement of the valvular prosthesis. Further, the auxiliary arches 18*a-c* are used as fastening means for anchoring the valvular prosthesis 100 to the stent 10.

It can also be noted from FIGS. 6*f* and 6*g* that lower part of the valvular prosthesis 100 is turned inside out such as to form a circumferential flap in which the respective head portions 30' of the fastening arches 19*a-c* and the respective head portions 31 of the auxiliary arches 18*a-c* engage. The valvular prosthesis 100 is thus fastened to the stent 10 with minimal play such that relative movement between the stent 10 and the valvular prosthesis 100 due to the peristaltic motion of the heart can be effectively prevented when the endoprosthesis 1 is implanted.

Figure 7A:
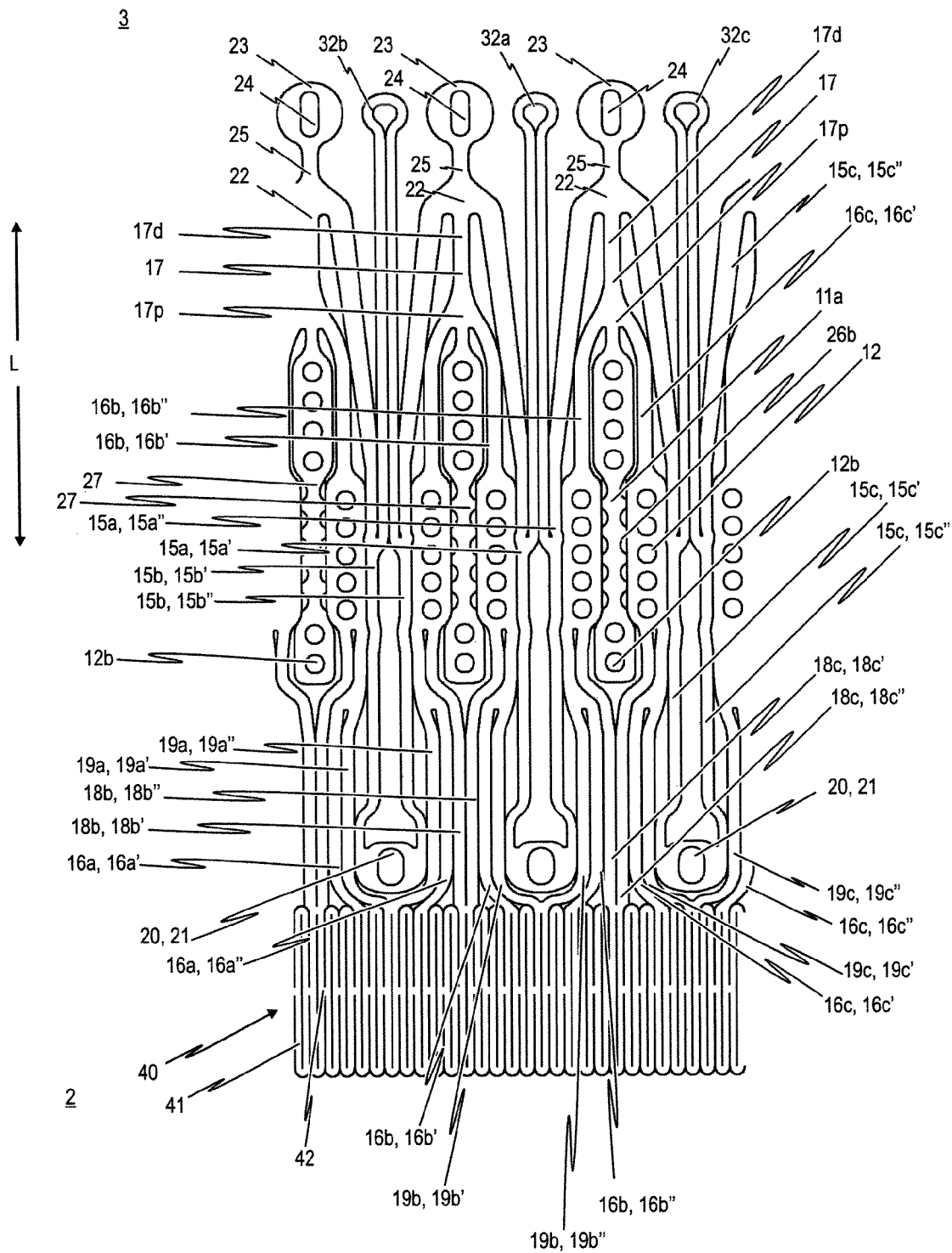

A seventh embodiment of the inventive stent 10 will be described in the following with reference to FIGS. 7*a-c*. Here, FIGS. 7*b* and 7*c* each show perspective side views of the fully-expanded stent 10, while FIG. 7*a* shows a two-dimensional projection of a cutting pattern used in the production of the cardiac valve stent according to the seventh embodiment of the invention in order to enable a cardiac valve stent according to e.g. FIG. 7*b* or FIG. 7*c* to be integrally cut from a section of tube, in particular a small metal tube.

Except for the lower end section, the stent 10 according to the seventh embodiment essentially corresponds to the stent according to the sixth embodiment of the present invention described above with reference to FIGS. 6*a-d* and FIGS. 6*f-i*.

Hence, the stent 10 according to the seventh embodiment has also a total of three positioning arches 15*a*, 15*b*, 15*c*, which again undertake the function of automatic positioning of the stent 10 in the plane of the valve of the pulmonary valve or the aortic valve. As in other embodiments of the stent 10, the positioning arches 15*a*, 15*b*, 15*c* have a radiused head portion 20, which engages in the pockets of the (insufficient) heart valve H being treated during positioning of the stent 10 at the implantation site in the heart (see FIG. 12*a*).

A total of three retaining arches 16*a*, 16*b*, 16*c* and three fastening arches 19*a*, 19*b*, 19*c* are also provided.

Also, fixing bridges 27 with additional fastening portions 11*a* are provided for additional fastening of a valvular prosthesis or parts of a valvular prosthesis. Each fixing bridge 27 is attached to one of the first connecting webs 17 and extends in the direction of the lower end 2 of the stent 10. The additional fastening portions 11*a* provided on the fixing bridges 27 have yet more fastening holes 12*b* and notches 26*b* to anchor a thread or a thin wire which is used to fastened the pericardial material or the valvular prosthesis to the stent 10 allowing minimal, preferably no, movement of the valvular prosthesis. It is of course conceivable to provide fastening holes or fastening eyelets, the diameter of which is adapted to the thickness of the thread or wire used for fastening the valvular prosthesis.

The seventh embodiment of the stent 10 also includes radial arches 32*a*, 32*b*, 32*c* extending from the positioning arches 15*a*, 15*b*, 15*c* towards the upper end 3 of the stent 10. As is shown most clearly in FIGS. 7*b* and 7*c*, the stent 10 has three radial arches 32*a*, 32*b*, 32*c*, with each arch 32*a*, 32*b*, 32*c* located between the two arms 15*a*, 15*a'*, 15*b*, 15*b'*, 15*c*, 15*c'* of each positioning arch 15*a*, 15*b*, 15*c*. Each radial arch 32*a*, 32*b*, 32*c* has a shape that is roughly inverse to each positioning arch 15*a*, 15*b*, 15*c* and extends in the opposite direction to each one of the positioning arches 15*a*, 15*b*, 15*c*.

Since in the implanted state of the endoprosthesis 1, substantial forces act on the valvular prosthesis 100 during the filling phase of the heart cycle (diastole), which are transmitted to the stent affixed with the valvular prosthesis 100, the secure anchoring of the stent 10 with the valvular prosthesis 100 affixed thereto at the site of implantation may of distinct importance. The seventh to eleventh embodiments of the stent 10 described in the following incorporate further measures which can be provided additionally to the above-described embodiments of retaining arches, auxiliary arches and radial arches which may more securely anchor of stent 10, endoprosthesis 1 respectively, at the site of implantation and which may prevent a positional displacement of endoprosthesis 1.

Figure 7B:
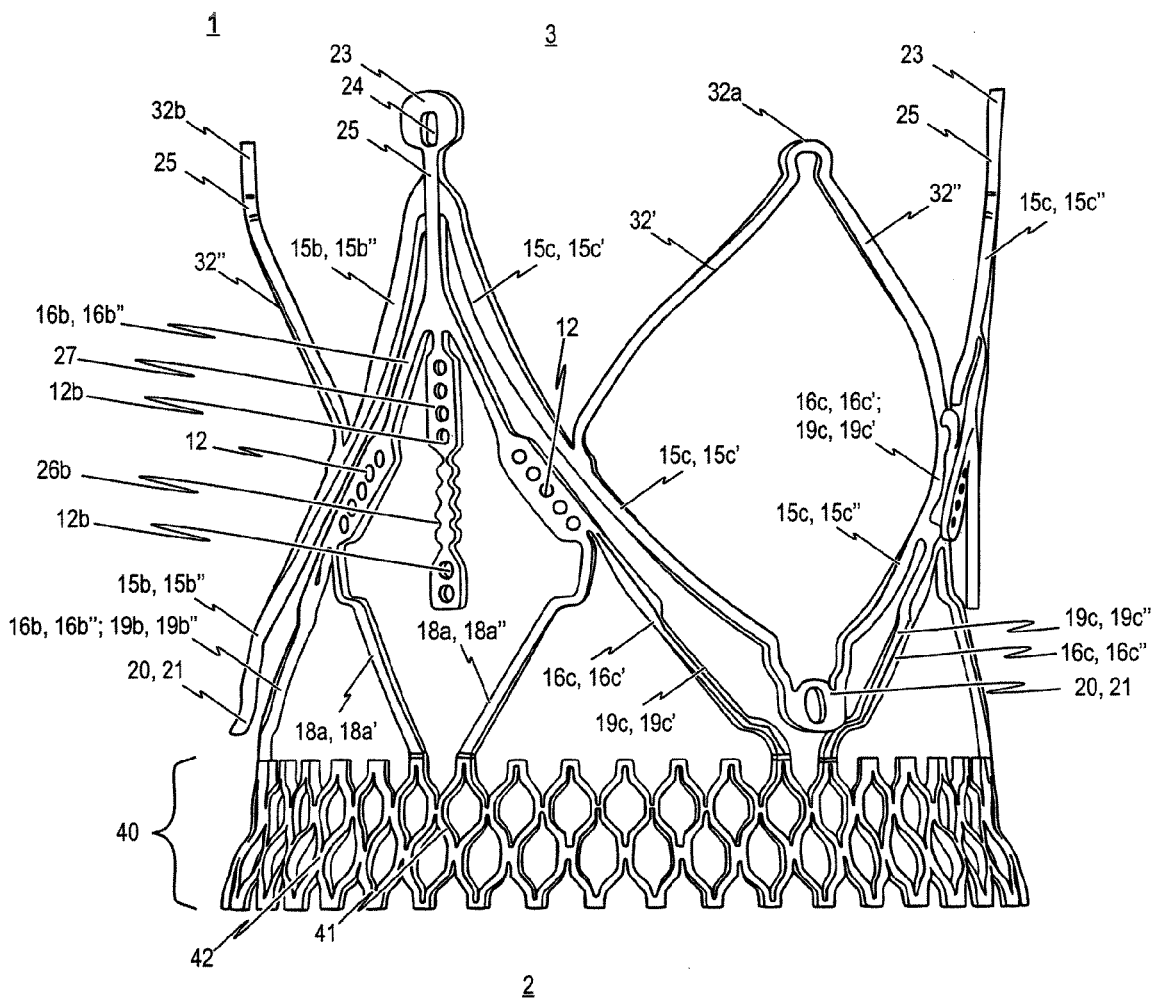
Figure 7C:
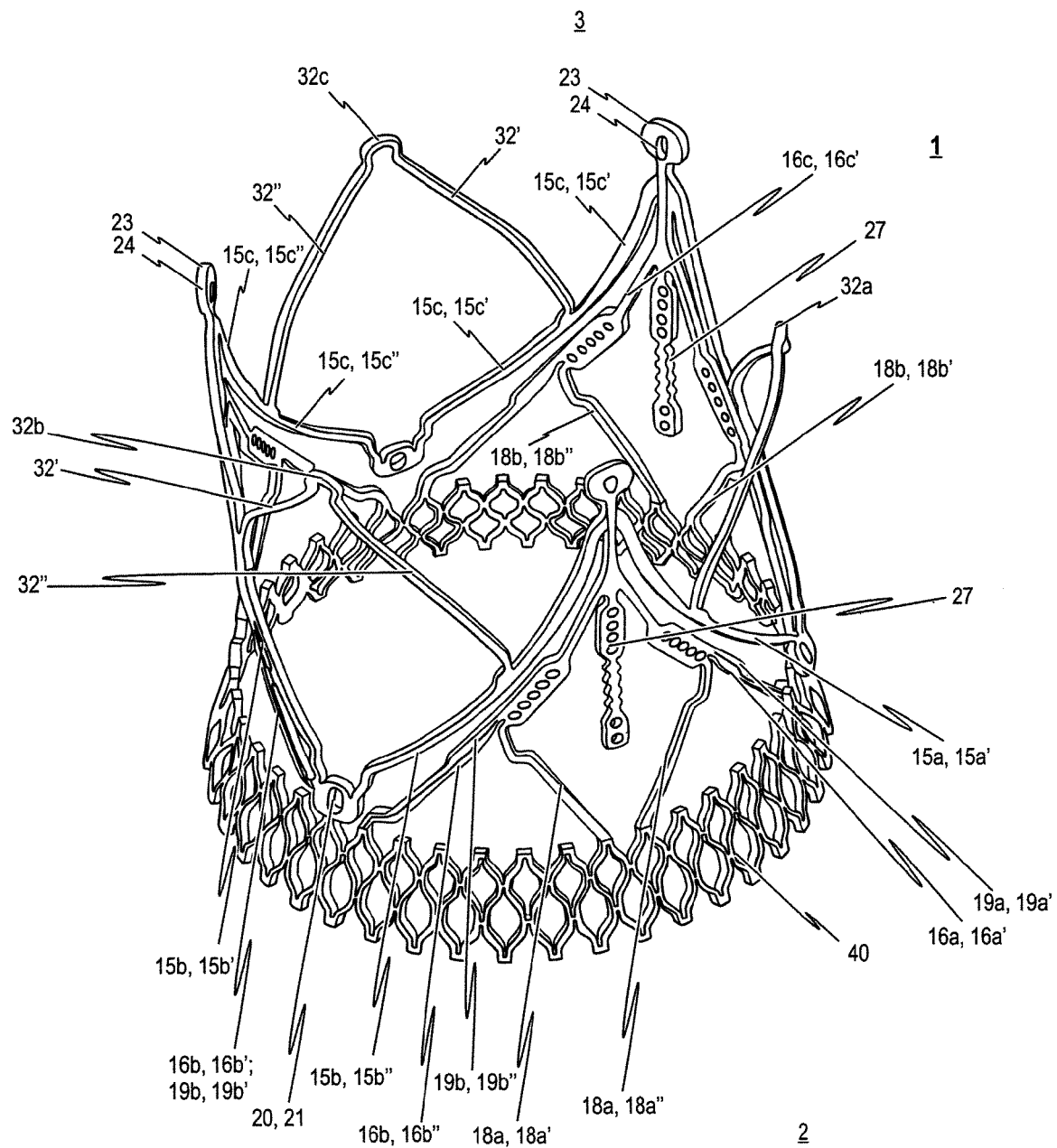

In detail, at least one annular collar 40, which forms the lower end 2 of the stent 10, is provided in accordance with the seventh embodiment as an additional anchoring measure for the stent 10 depicted in FIGS. 7*a-c*. Said annular collar 40 may be connected to each or a part of the lower end sections of the respective retaining arms 16*a'*, 16*a'''*, 16*b'*, 16*b'''*, 16*c'*, 16*c'''* of retaining arches 16*a-c* and the lower end sections of the respective arms 19*a'*, 19*a'''*, 19*b'*, 19*b'''*, 19*c'*, 19*c'''* of the fastening arches 19*a-c*, as can be seen in particular from the cutting pattern pursuant FIG. 7*a*. Also, the lower end sections of the respective arms 18*a'*, 18*a'''*, 18*b'*, 18*b'''*, 18*c'*, 18*c'''* of the auxiliary arches 18*a*, 18*b*, 18*c* may be connected to the annular collar 40.

The annular collar 40 exhibits a plurality of supporting webs 41 which run parallel to the longitudinal axis of the stent 10 in the non-expanded state of said stent 10 and are interconnected by transversal webs 42 (cf. FIG. 7*a*). In the expanded state of stent 10, the supporting webs 41 and the transversal webs 42 form a serrated, rhomboidal or serpentine-like annular collar 40 which abuts against the vascular wall in the implanted state of endoprosthesis 1, stent 10 respectively. FIGS. 7*b* and 7*c* show the annular collar 40 in the expanded state.

The annular collar 40 serves as a supporting body through which the radial forces developing due to the self-expansion are transmitted to the vascular wall. Since a relatively large contact area of the stent 10 interacts with the vascular wall, and because of the serrated, rhomboidal or serpentine structure to the annular collar 40, there may be a decreased risk of injury to the artery or the tissue despite the increased radial forces.

Accordingly, not only the rigidity of the stent 10 can be increased after its self-expansion by the providing of the annular collar 40, but also the anchorage of the stent 10 in the implanted state can be improved or strengthened. Additionally, the annular cross-sectional shape to annular collar 40 increases the seal between the vascular wall and the endoprosthesis 1.

Such an annular collar 40 is advantageously configured as a self-expandable supporting structure which advantageously effects an even further improved anchoring of the stent 10 at the site of implantation due to its radially-outward-acting contact pressure and its design such that a displacing or rotating of the stent 10 with the valvular prosthesis 100 can be further prevented.

Figure 8A:
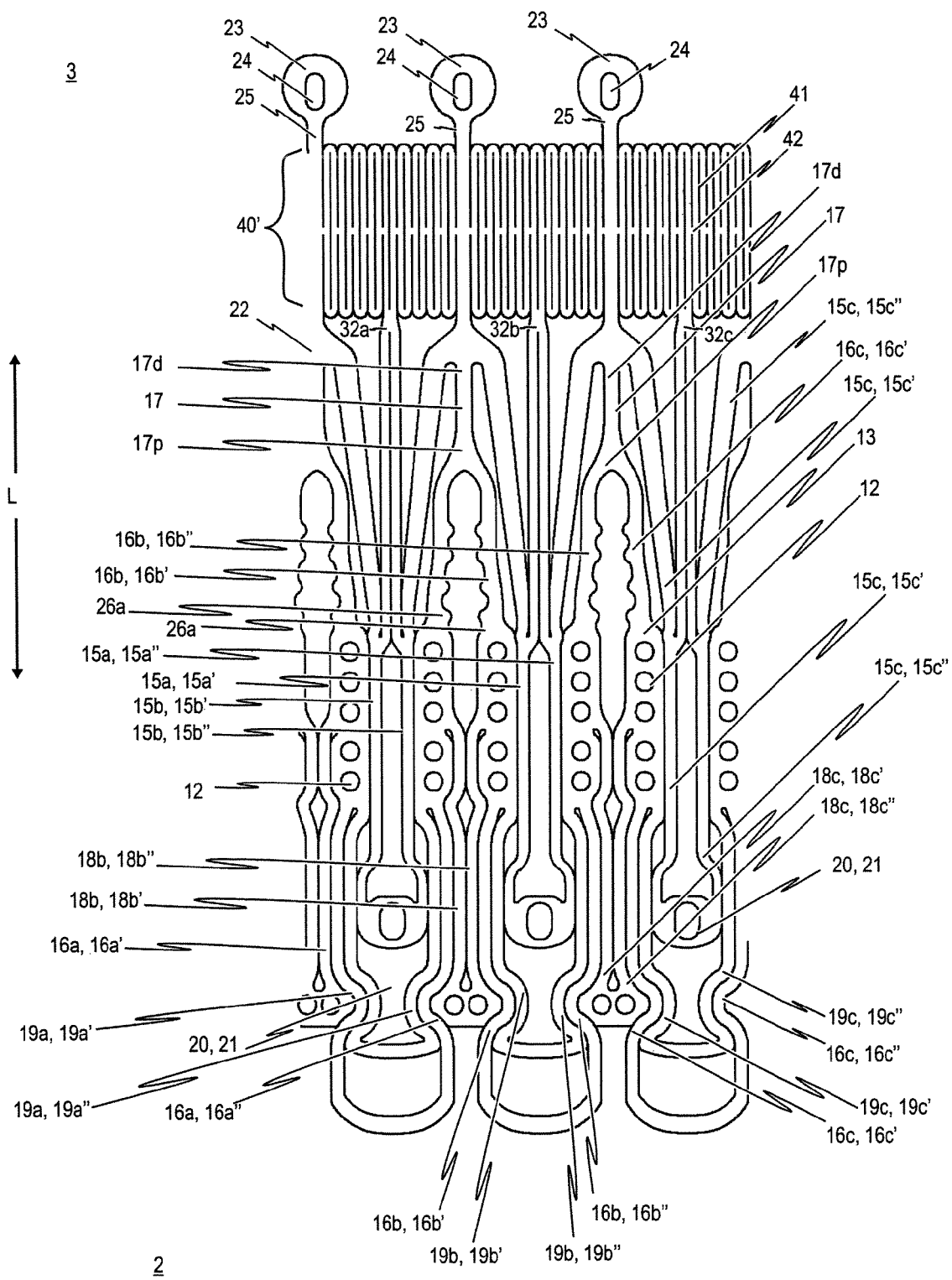
Figure 8B:
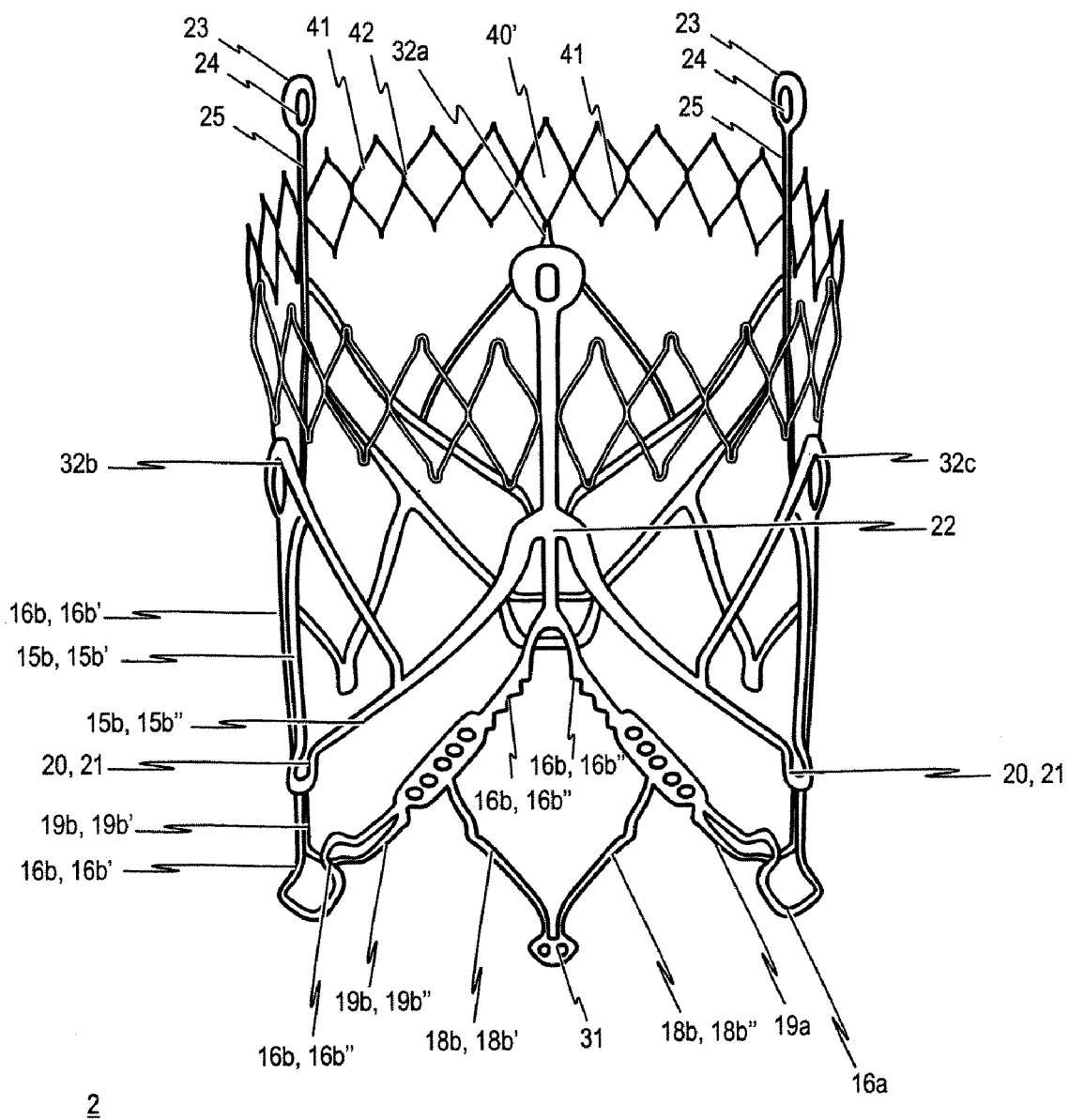
Figure 8C:
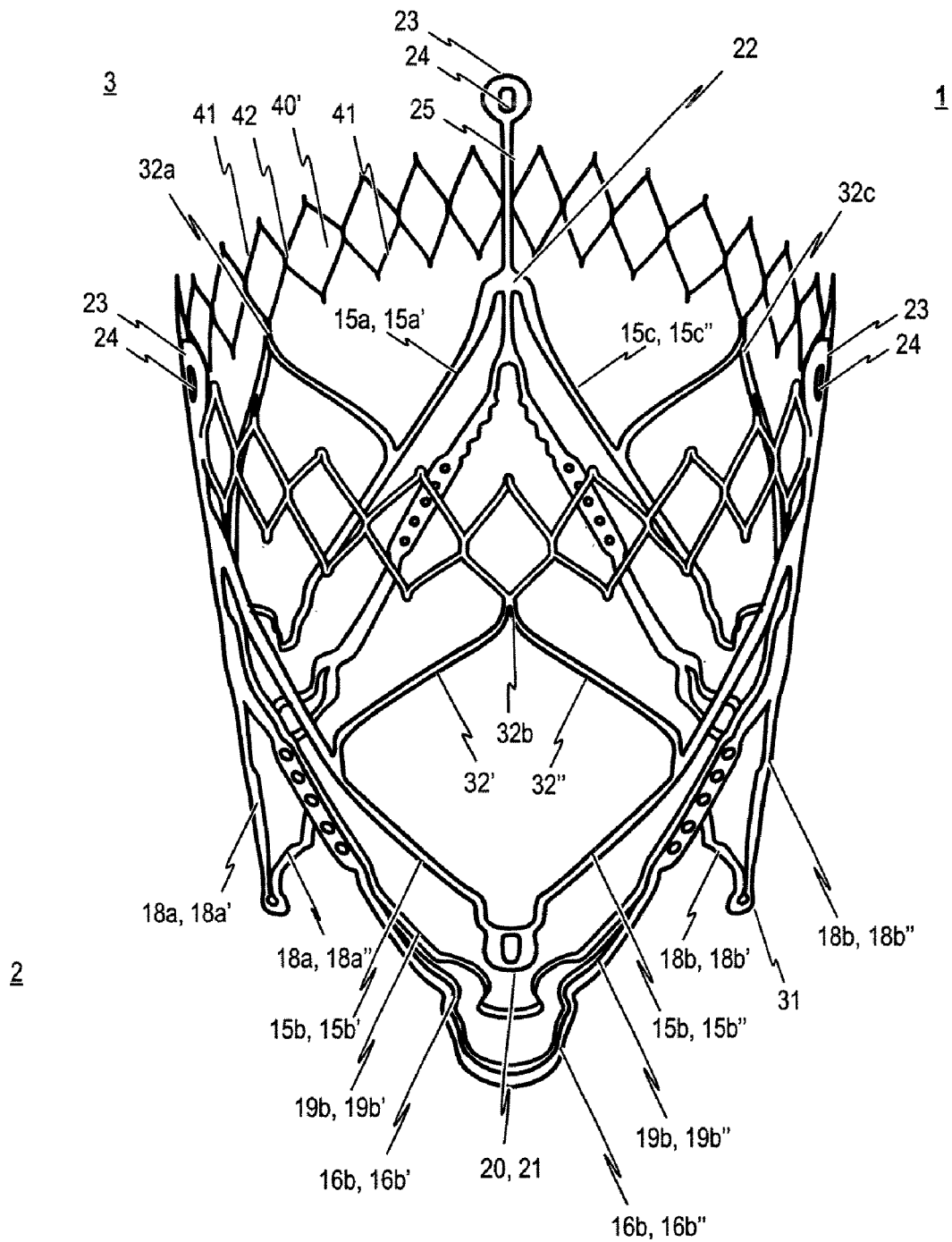

An eighth embodiment of the inventive stent 10 is shown in FIGS. 8a-c. In detail, FIG. 8b and FIG. 8c each show the stent 10 of the eighth embodiment in a perspective side view, whereby the stent 10 is fully expanded. FIG. 8a shows a two-dimensional projection of a cutting pattern applicable to manufacturing a cardiac valve stent according to the eighth embodiment of the invention in order to cut a cardiac valve stent pursuant to FIG. 8b or FIG. 8c integrally from a portion of a tube, in particular a small metal tube.

Except for the upper end section, the stent 10 according to the eight embodiment essentially corresponds to the stent according to the fifth embodiment of the present invention described above with reference to FIGS. 5a-d.

Hence, the stent 10 of the eight embodiment similarly has a total of three positioning arches 15a, 15b, 15c, which again undertake the function of automatic positioning of the stent 10 in the plane of the valve of the pulmonary valve or the aortic valve. As in other embodiments of the stent 10, the positioning arches 15a, 15b, 15c have a radiused head portion 20, which engages in the pockets of the (insufficient) heart valve H being treated during positioning of the stent 10 at the implantation site in the heart (see FIG. 12a).

A total of three retaining arches 16a, 16b, 16c and three fastening arches 19a, 19b, 19c are also provided.

Furthermore, in the eight embodiment stent 10, further notches 26a are provided in addition to the fastening holes 12 in the fastening portion 11 which serve as additional anchoring means for the prosthetic valve 100 and guides for the suture thread or wire. These additional notches 26a also minimize movement of the suture thread or wire thereby reducing wear on the thread or wire by rubbing on the first connecting web 17 when the endoprosthesis 1 is implanted. The additional notches 26a also ensure that the upper region of a valvular prosthesis can be fastened firmly to the cardiac valve stent 10 allowing minimal movement of the prosthesis thereby further minimizing the likelihood of wear induced by friction on the suture thread or wire.

A total of three retaining arches 16a, 16b, 16c and three fastening arches 19a, 19b, 19c are also provided.

In contrast to the seventh embodiment (cf. FIG. 7a-c), however, the lower (proximal) end 2 of the stent 10 remains unchanged in the eighth embodiment while an upper annular collar 40' is formed at the upper (distal) end 3 of the stent 10. As FIGS. 8b and 8c show, the annular collar 40' is constructed of supporting webs 41 and transversal webs 42 and forms a rhombic supporting structure in the expanded state.

To be seen from the illustration of the cutting pattern according to FIG. 8a is that the upper annular collar 40' utilized in the eighth embodiment is connected to the upper head portions of radial arches 32a, 32b, 32c. On the other hand, the upper annular collar 40' is connected to the second connecting web 25 such that it is disposed at a distance from the plane in which the catheter retaining means 23 are positioned in the expanded state (cf. FIGS. 8b, 8c). Specifically, the annular collar 40' in the eighth embodiment is situated between the plane in which the catheter retaining means 23 lies and the plane in which the connecting portion 22 of the two arms of neighboring positioning arches 15a-c lies. To this end, the connecting web 25 is—compared to the connecting web in the fifth embodiment—configured to be somewhat longer.

Since the upper annular collar 40' utilized in the eighth embodiment is comparable to the lower annular collar 40 utilized in the seventh embodiment in terms of functioning, and is not further described for clarification purposes.

Figure 9A:
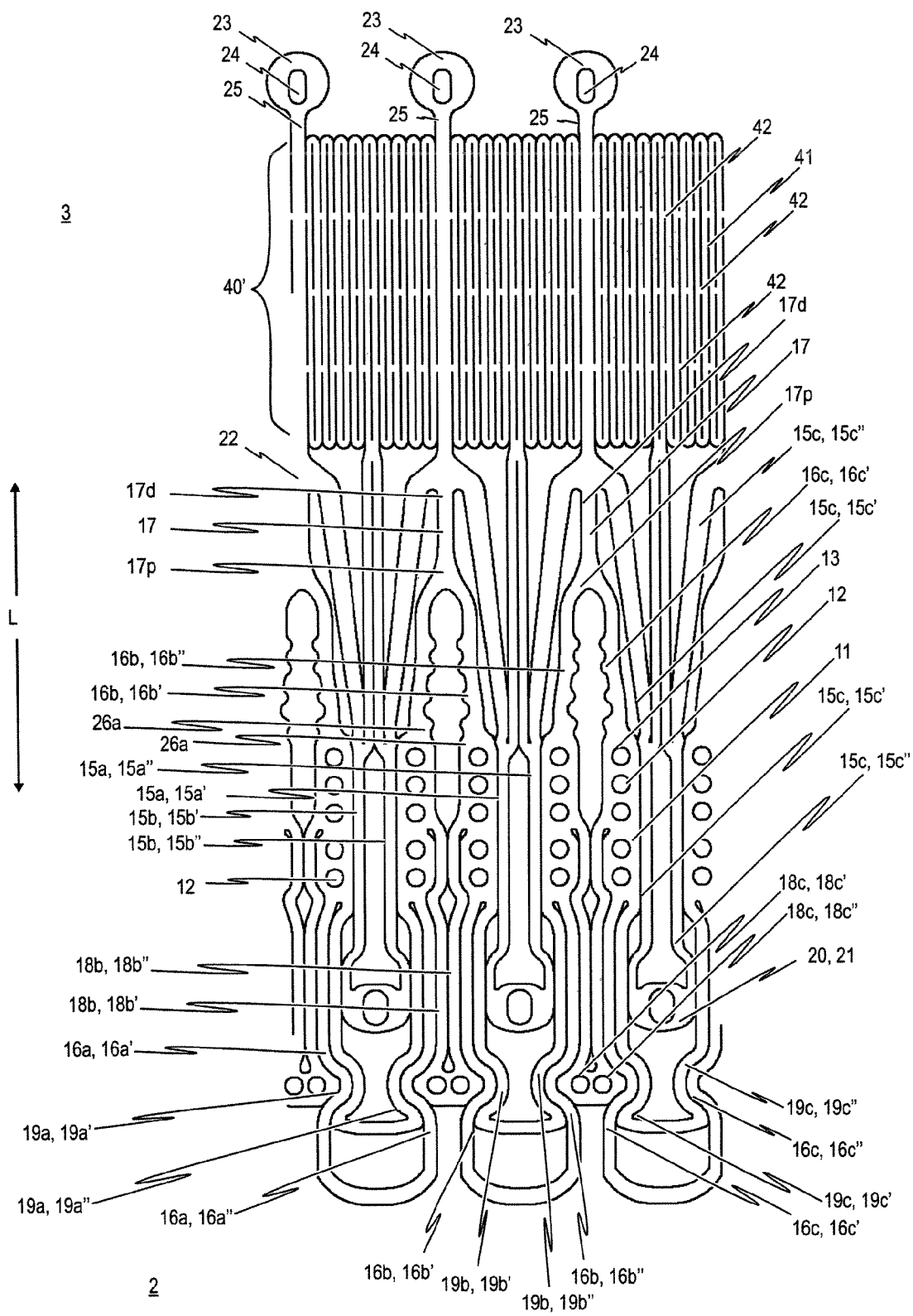
Figure 9B:
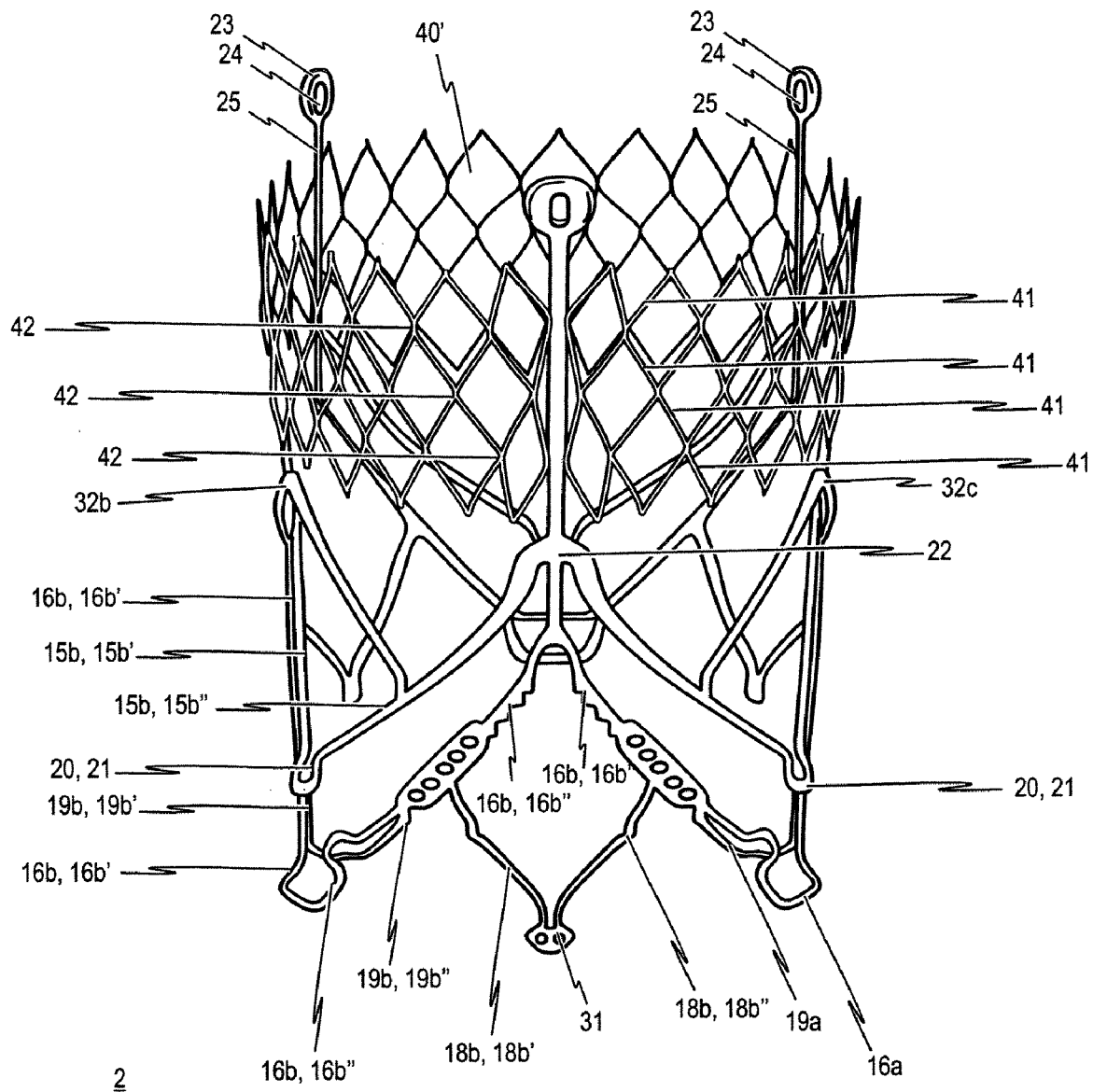

The following will reference FIGS. 9a and 9b in describing a ninth embodiment of the stent 10 according to the invention. FIG. 9b thereby shows a perspective view of the stent 10 in the expanded state. FIG. 9a shows a two-dimensional projection of a cutting pattern applicable to manufacturing a cardiac valve stent to the ninth embodiment of the invention in order to cut a cardiac valve stent pursuant to FIG. 9b integrally from a portion of a tube, in particular a small metal tube.

Since an upper annular collar 40' is likewise formed at the upper end 3 of the stent 10, the stent 10 in accordance with the ninth embodiment is similar to the previously-described stent according to FIGS. 8a-c (eighth embodiment). In contrast to the eighth embodiment, the upper annular collar 40' in the ninth embodiment is configured to be longer in the longitudinal direction of the stent 10. Specifically, a comparison of FIG. 9b and FIG. 8b shows that in the ninth embodiment, two rhombic annular bodies lying atop one another are employed as the annular collar 40'. This may increase the radial contact force that the stent 10 exerts from its upper end 3. A correspondingly elongated connecting web 25 is again utilized in the embodiment according to FIGS. 9a-b.

Figure 10:
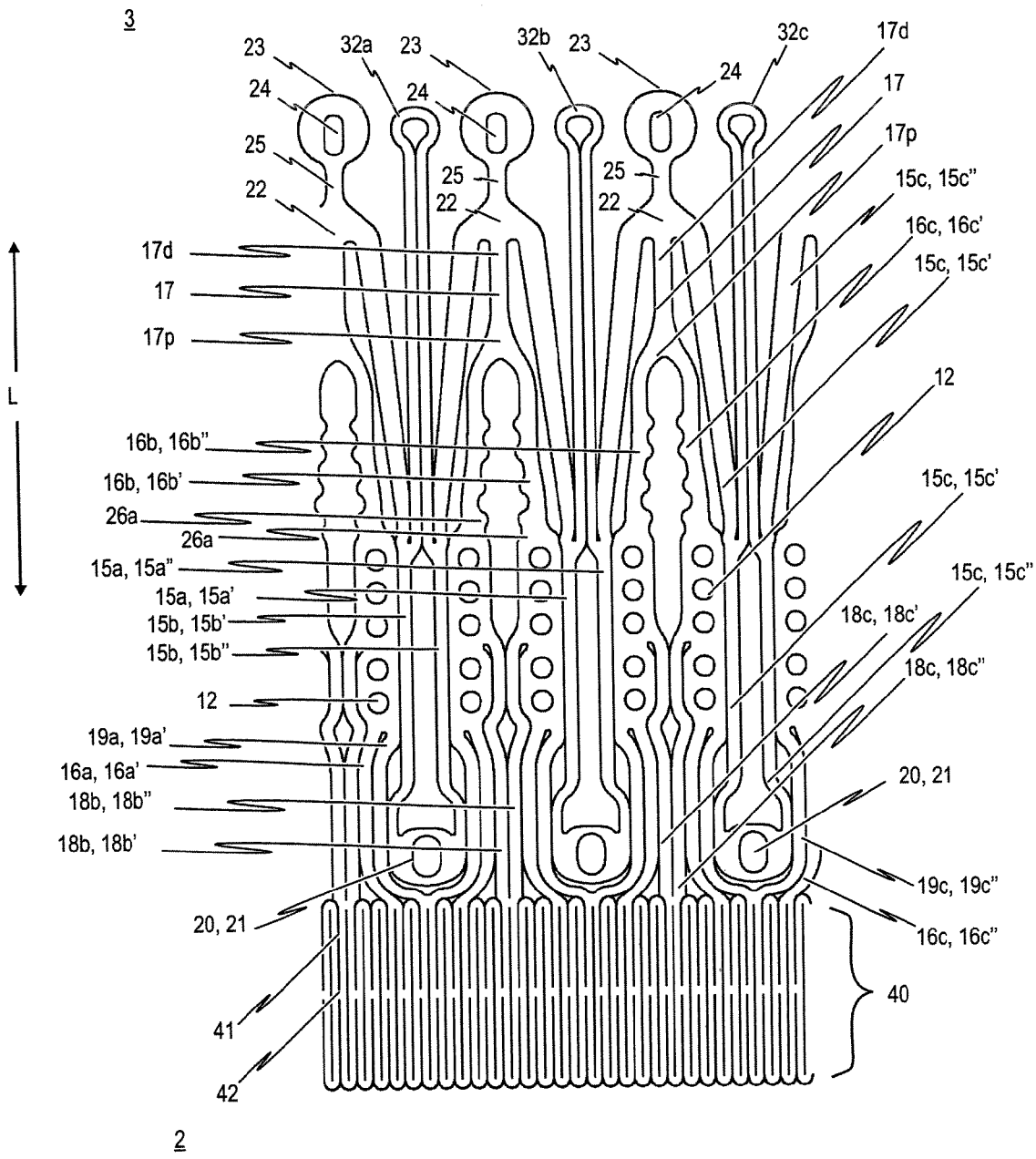

FIG. 10 shows a two-dimensional projection of a cutting pattern which can be used to cut a cardiac valve stent 10 in accordance with a tenth embodiment of the invention as one integral piece from a portion of a tube, in particular a small metal tube.

As also with the eight embodiment described above with reference to FIGS. 9a-b and the ninth embodiment described above with reference to FIGS. 8a-b, the tenth embodiment of the inventive stent 10 essentially corresponds to the embodiment described with reference to FIGS. 5a-d.

In contrast, for example, to the eight embodiment (cf. FIG. 8a-c), however, the upper (distal) end 3 of the stent 10 remains unchanged in the tenth embodiment while a lower annular collar 40 is formed at the lower (proximal) end 2 of the stent 10. As FIG. 10 shows, the annular (lower) collar 40 is also constructed of supporting webs 41 and transversal webs 42 and forms a rhombic supporting structure in the expanded state.

To be seen from the illustration of the cutting pattern according to FIG. 10 is that the lower annular collar 40 utilized in the tenth embodiment is connected to the lower head portions of retaining arches 16a, 16b, 16c, of fastening arches 19a, 19b, 19c, and of auxiliary arches 18a, 18b, 18c. On the other hand, the lower annular collar 40 is connected to the retaining arches 16a, 16b, 16c, of fastening arches 19a, 19b, 19c, and of auxiliary arches 18a, 18b, 18c such that it is disposed at a distance from the plane in which the catheter retaining means 23 is positioned in the expanded state.

Figure 11:
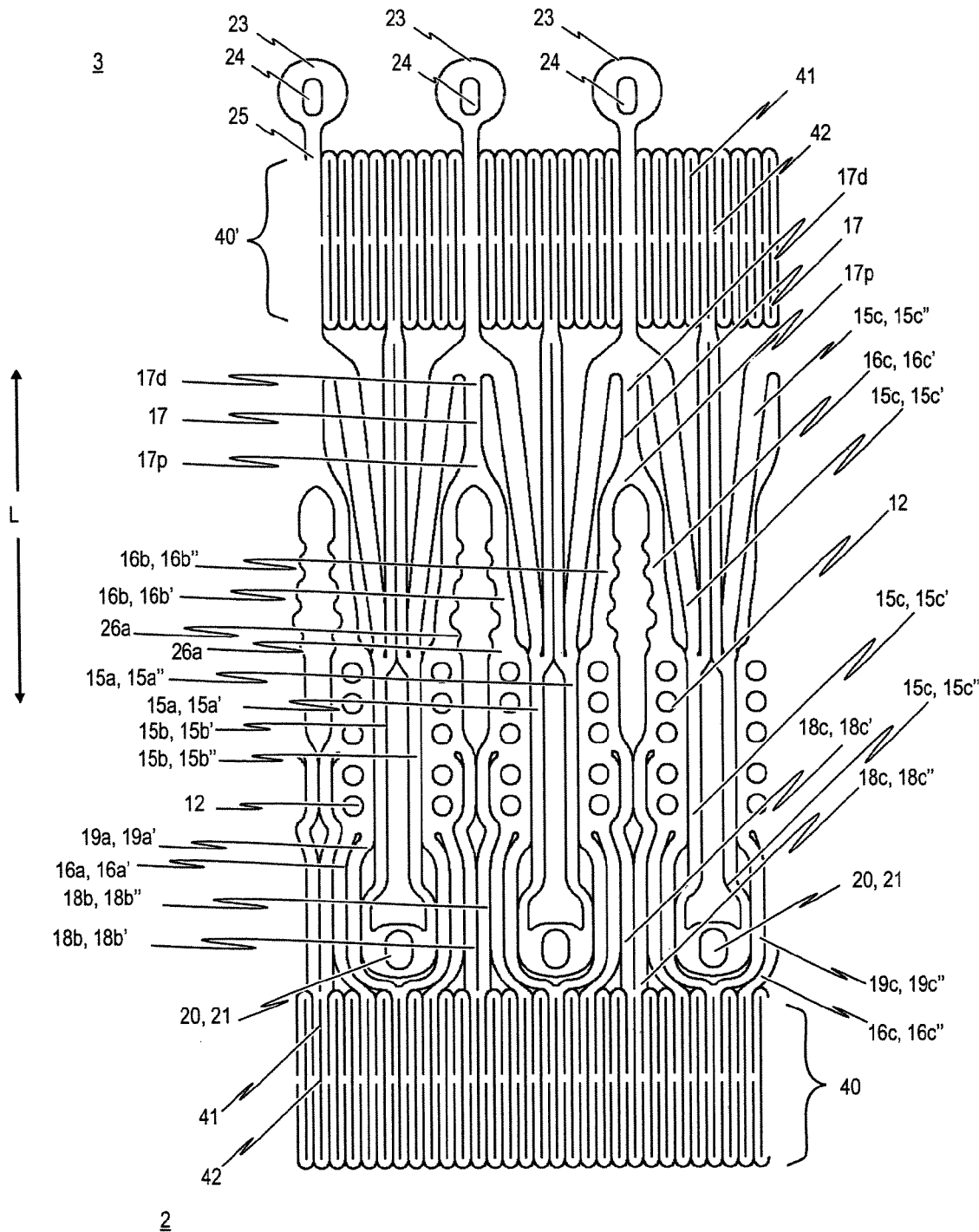

Since the lower annular collar 40 utilized in the tenth embodiment is comparable to the lower annular collar 40 utilized in the seventh embodiment in terms of functioning, and is not further described for clarification purposes FIG. 11 shows a two-dimensional projection of a cutting pattern which can be used to cut a cardiac valve stent 10 in accordance with a eleventh embodiment of the invention as one integral piece from a portion of a tube, in particular a small metal tube.

Except for the upper and lower end section, the stent 10 according to the eleventh embodiment is similar to the stent according to the fifth embodiment of the present invention described above with reference to FIGS. 5a-d.

Hence, the stent 10 according to the eleventh embodiment has also a total of three positioning arches 15a, 15b, 15c, which again undertake the function of automatic positioning of the stent 10 in the plane of the valve of the pulmonary valve or the aortic valve. As in other embodiments of the stent 10, the positioning arches 15a, 15b, 15c have a radiused head portion 20, which engages in the pockets of the (insufficient) heart valve H being treated during positioning of the stent 10 at the implantation site in the heart (see FIG. 12a).

A total of three retaining arches 16a, 16b, 16c and three fastening arches 19a, 19b, 19c are also provided.

The eleventh embodiment of the stent 10 also includes radial arches 32a, 32b, 32c extending from the positioning arches 15a, 15b, 15c towards the upper end 3 of the stent 10. As is shown in FIG. 11, the stent 10 has three radial arches 32a, 32b, 32c, with each arch 32a, 32b, 32c located between the two arms 15a, 15a', 15b, 15b', 15c, 15' of each positioning arch 15a, 15b, 15c. Each radial arch 32a, 32b, 32c has a shape that is roughly inverse to each positioning arch 15a, 15b, 15c and extends in the opposite direction to each one of the positioning arches 15a, 15b, 15c.

The eleventh embodiment of the stent (cf. FIG. 11) differs from the fifth embodiment of the present invention described above with reference to FIGS. 5a-d in that two annular collars 40, 40', which forms the lower and upper ends 2, 2' of the stent 10, are provided in accordance with the eleventh embodiment as an additional anchoring measure for the stent 10. As in the seventh embodiment described above with reference to FIGS. 7a-c, the lower annular collar 40 is connected to the lower end sections of the respective retaining arms 16a', 16a", 16b', 16b", 16c', 16c" of retaining arches 16a-c and the lower end sections of the respective arms 19a', 19a", 19b', 19b", 19c', 19c" of the fastening arches 19a-c, as can be seen in particular from the cutting pattern pursuant FIG. 11. On the other hand, the upper annual collar 40' utilized in the eleventh embodiment is connected to the upper head portions of radial arches 32a, 32b, 32c. In detail, the annual collar 40' in the eleventh embodiment is situated between the plane in which the catheter retaining means 23 lies and the plane in which the connecting portion 22 of the two arms of neighboring positioning arches 15a-c lies.

As already described with respect to the seventh to tenth embodiment of the present invention, the upper and lower annular collars 40, 40' exhibits a plurality of supporting webs 41 which run parallel to the longitudinal axis of the stent 10 in the non-expanded state of said stent 10 and are interconnected by transversal webs 42 (cf. FIG. 11). Again, in the expanded state of stent 10, the supporting webs 41 and the transversal webs 42 form a serrated, rhomboidal or serpentine-like annular collars 40, 40' which abuts against the vascular wall in the implanted state of endoprosthesis 1, stent 10 respectively.

A comparison of FIG. 11 with the cutting patterns according to FIGS. 8a and 9a shows that the stent 10 in accordance with the eleventh embodiment of the invention basically proceeds from the stent 10 according to the eighth embodiment (cf. FIGS. 8a-c), whereby for the purpose of improved anchoring, an additional (lower) annular collar 40 is formed at the lower end 2 of the stent 10. This additional lower annular collar corresponds substantially to the lower annular collar employed in the seventh embodiment (cf. FIGS. 7a-c). To avoid repetition, reference is made to the foregoing remarks with respect to the seventh and eighth embodiments.

Naturally, the annular collar 40 or 40' can in principle also be arranged in a plane in which the valvular prosthesis is situated. It is furthermore not imperative for the annular collar 40 to be connected to all the end sections of the retaining arches 16a-c or the auxiliary fastening arches 19a-c respectively. Nor does the upper annular collar 40' necessarily have to be connected to all the end sections of the radial arches 32.

Figure 1A:
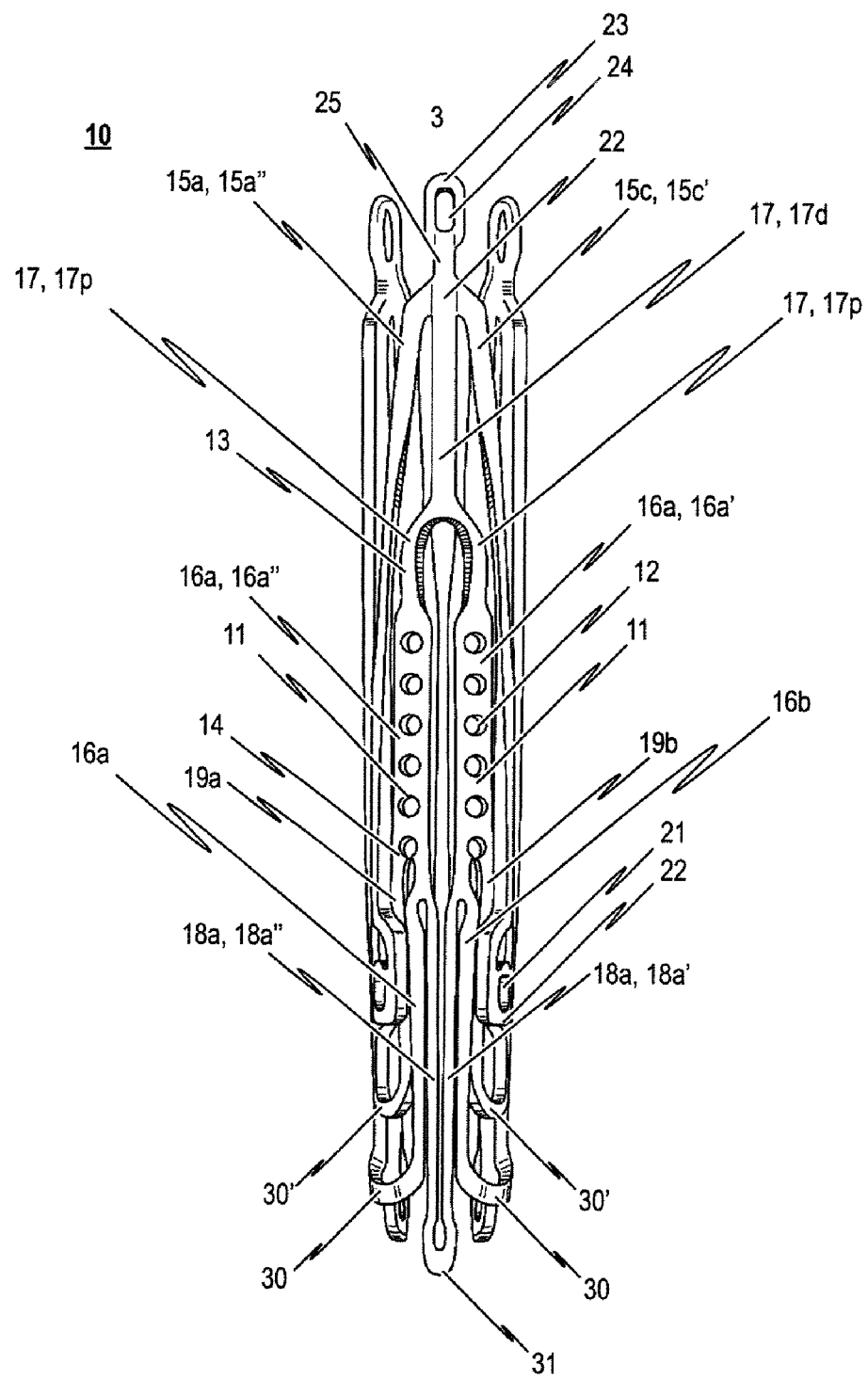
Figure 1B:
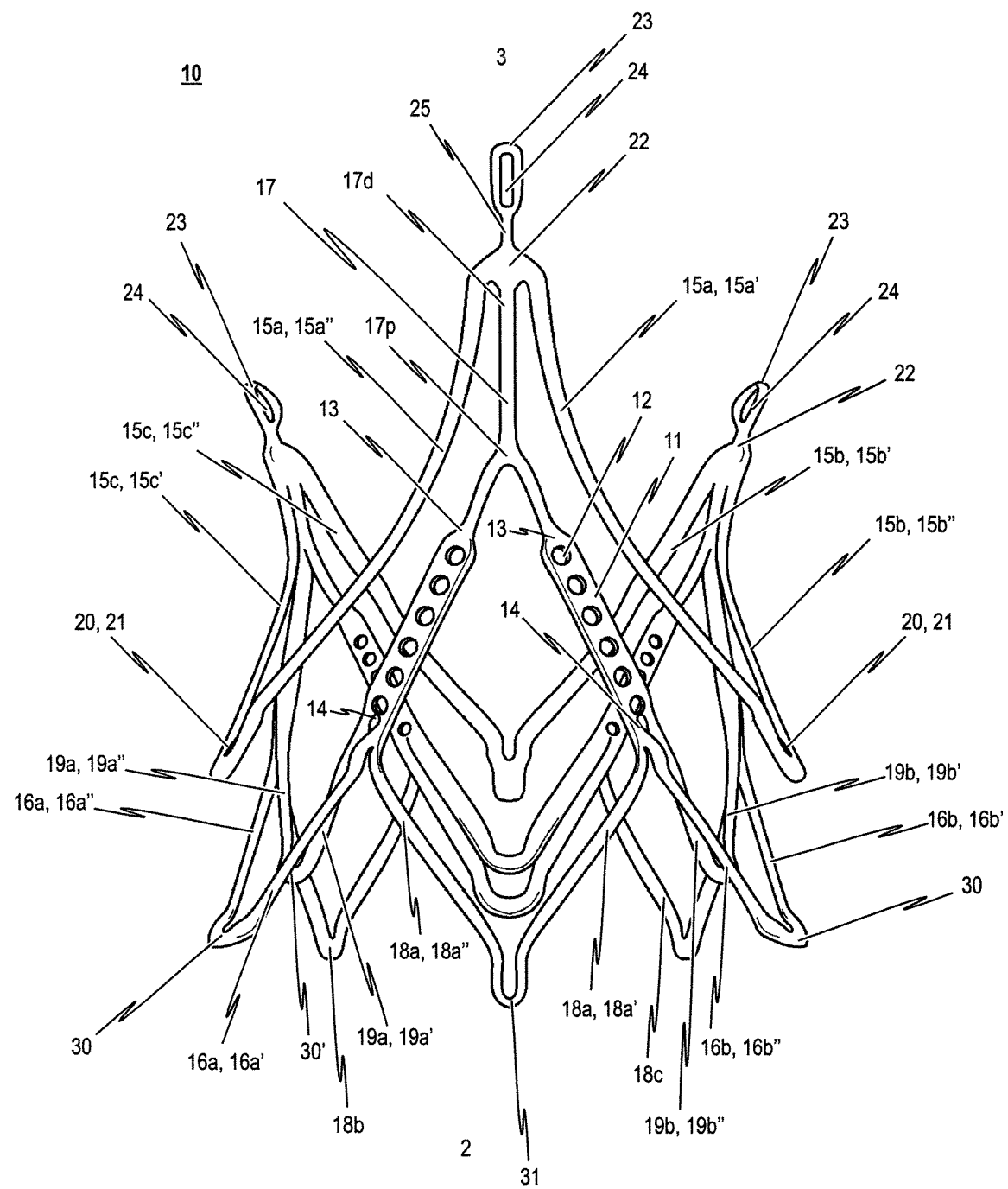
Figure 1C:
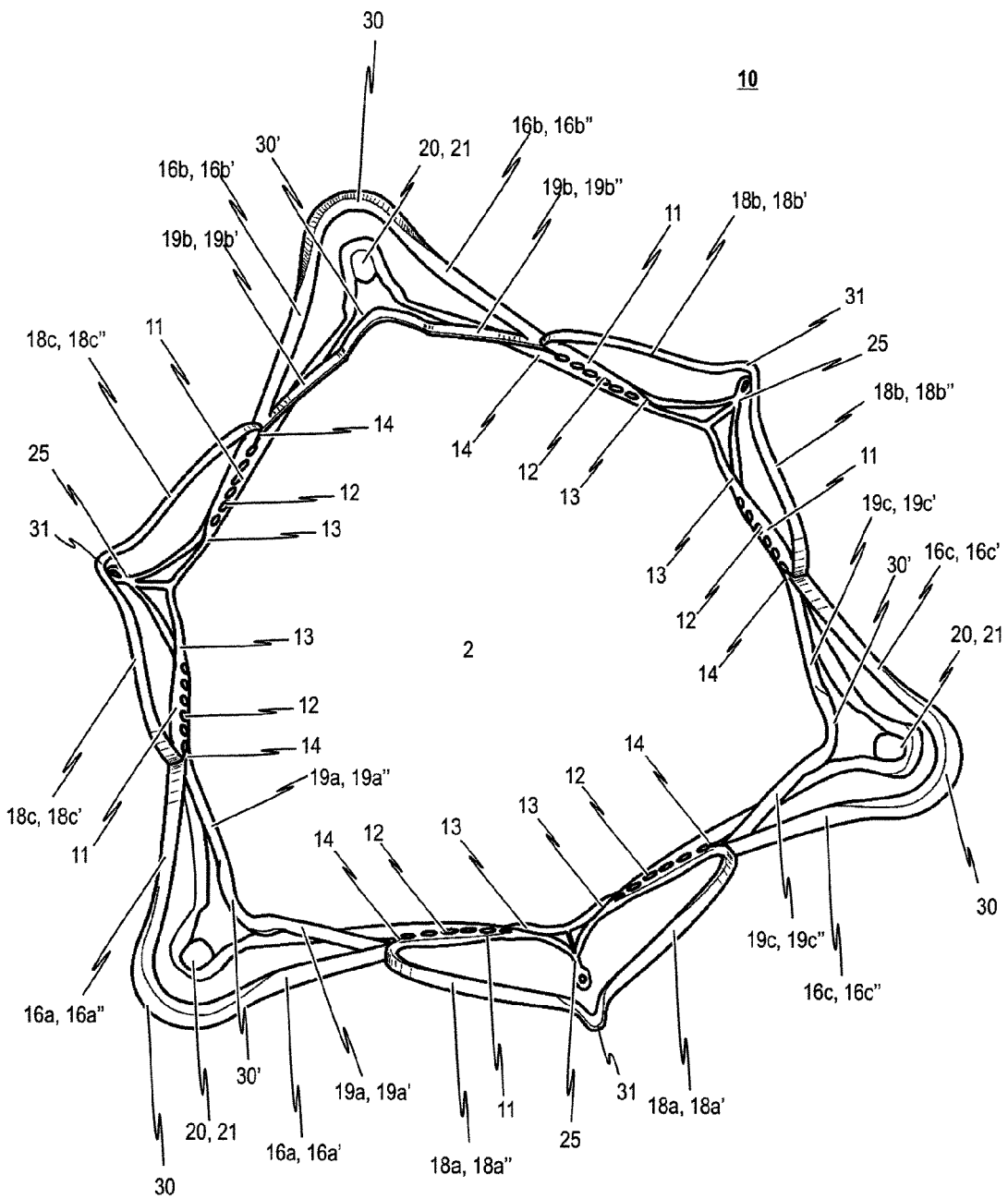
Figure 1D:
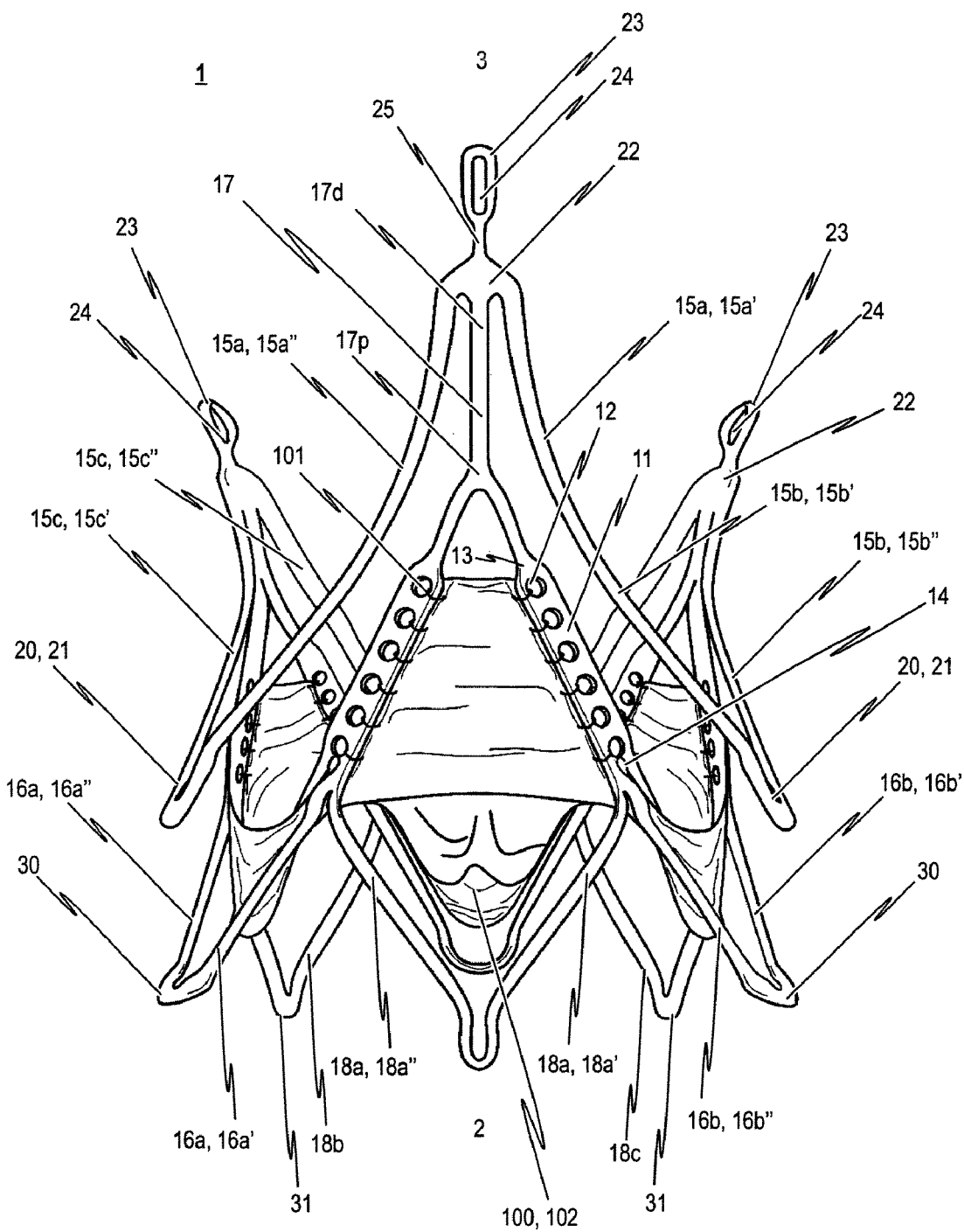
Figure 1E:
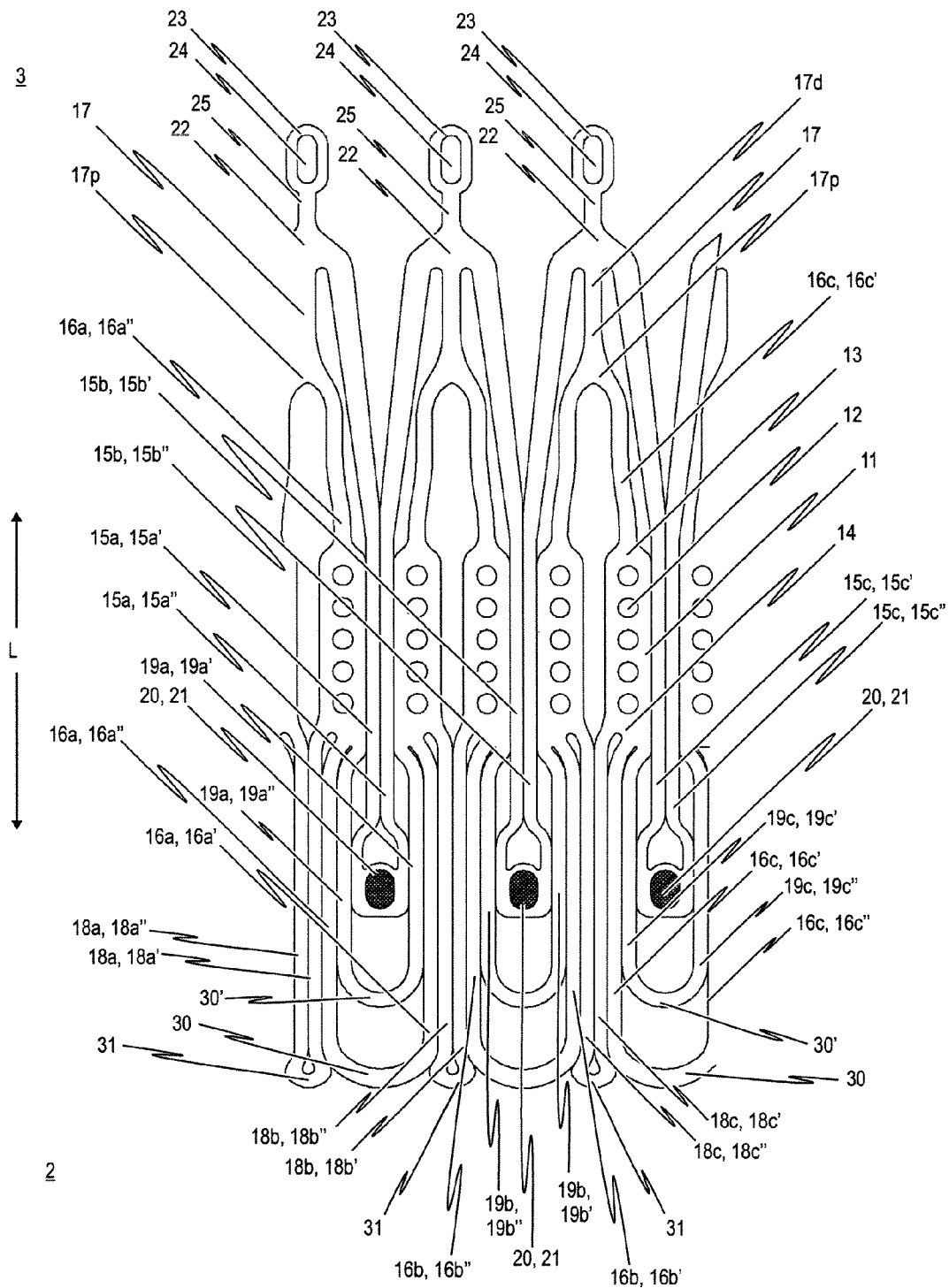
Figure 2A:
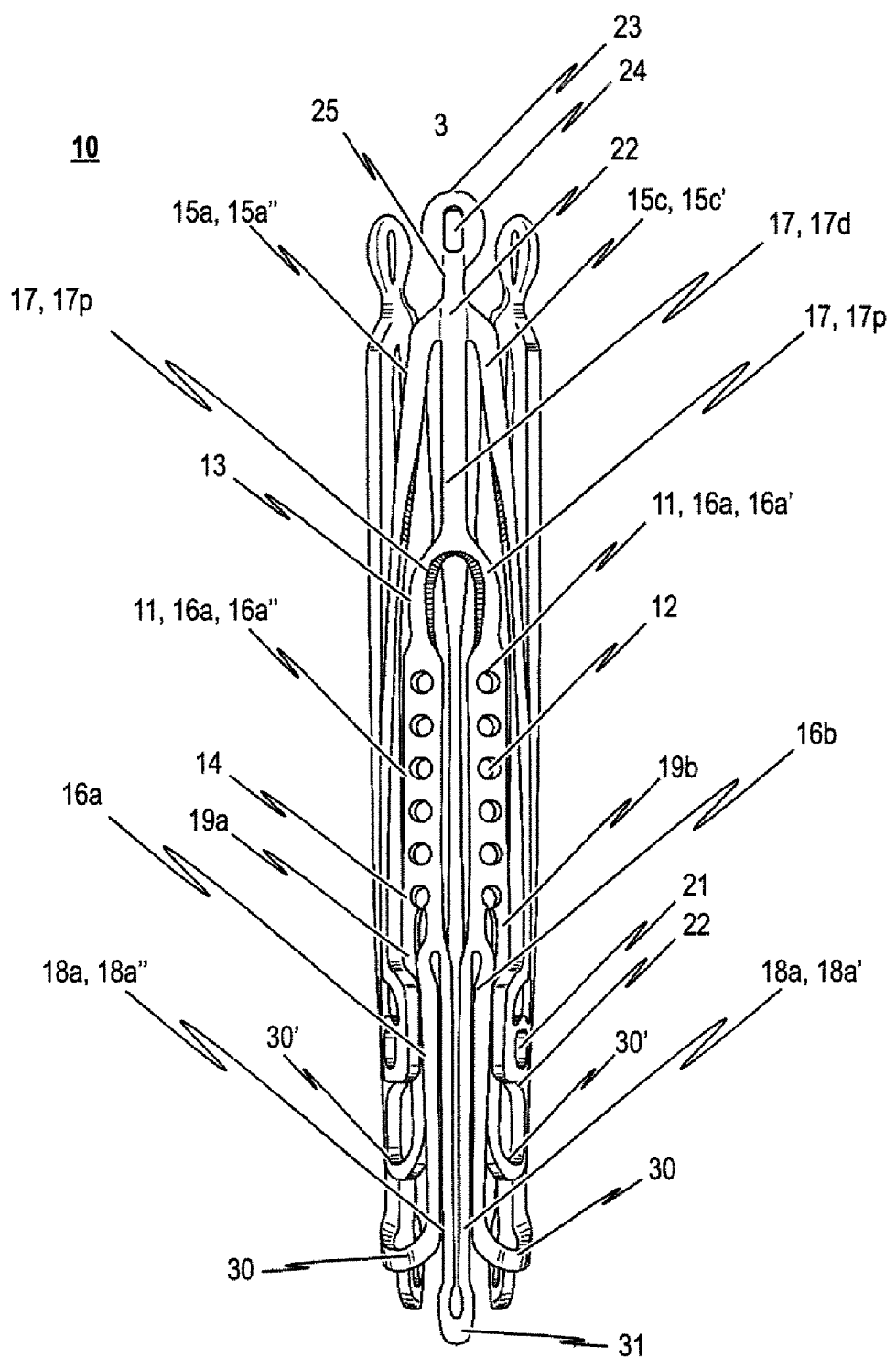
Figure 2B:
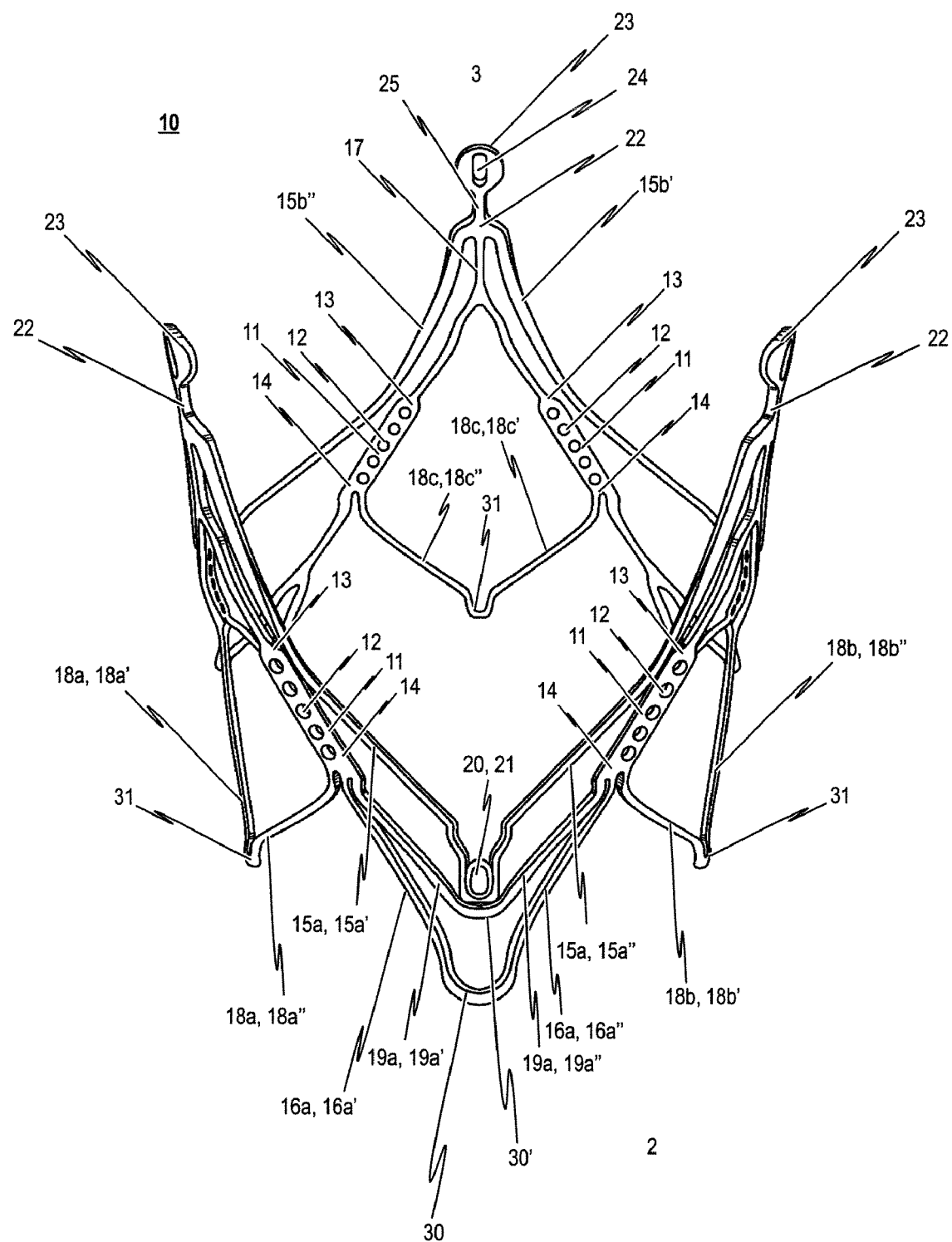
Figure 2C:
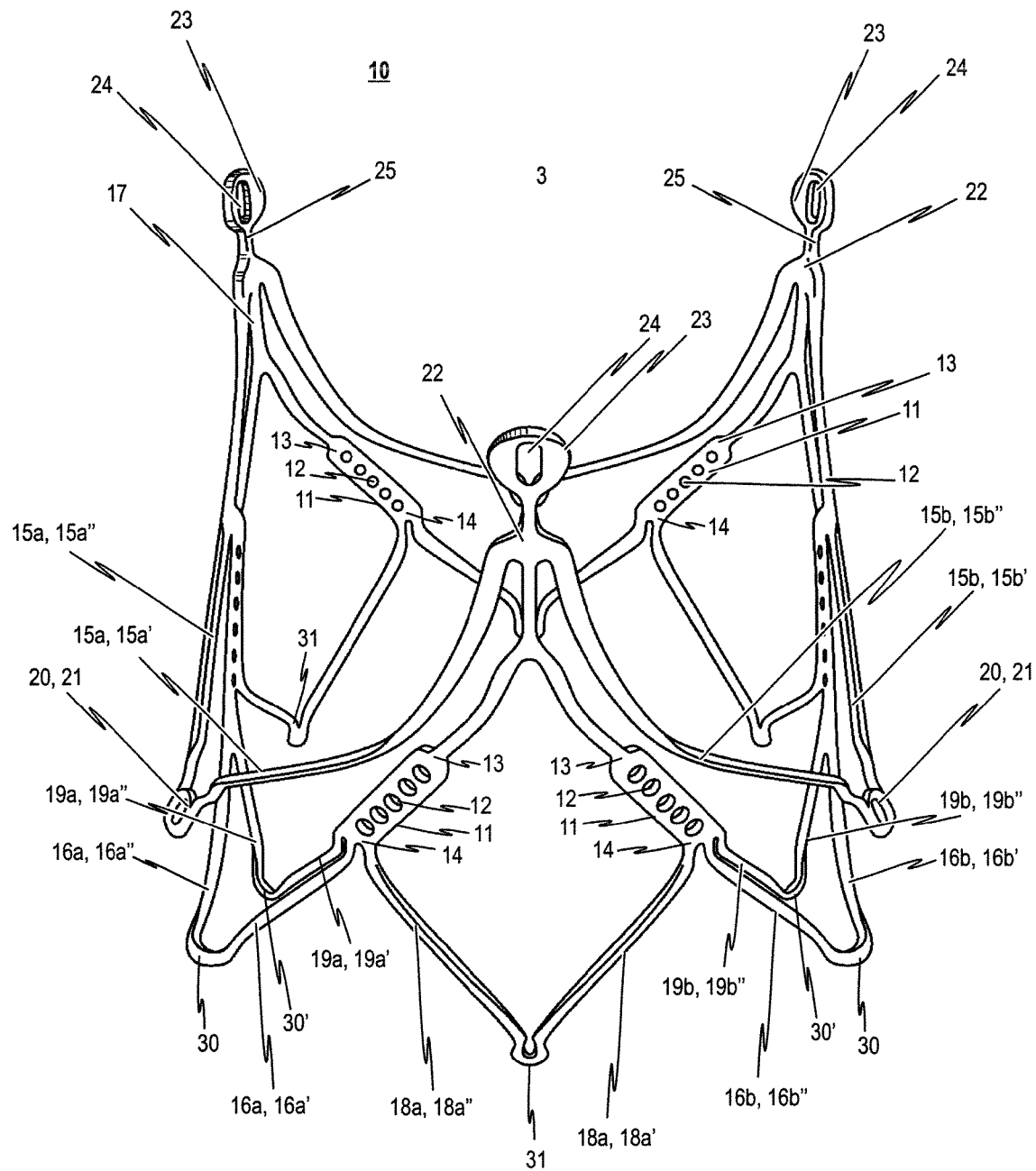
Figure 2D:
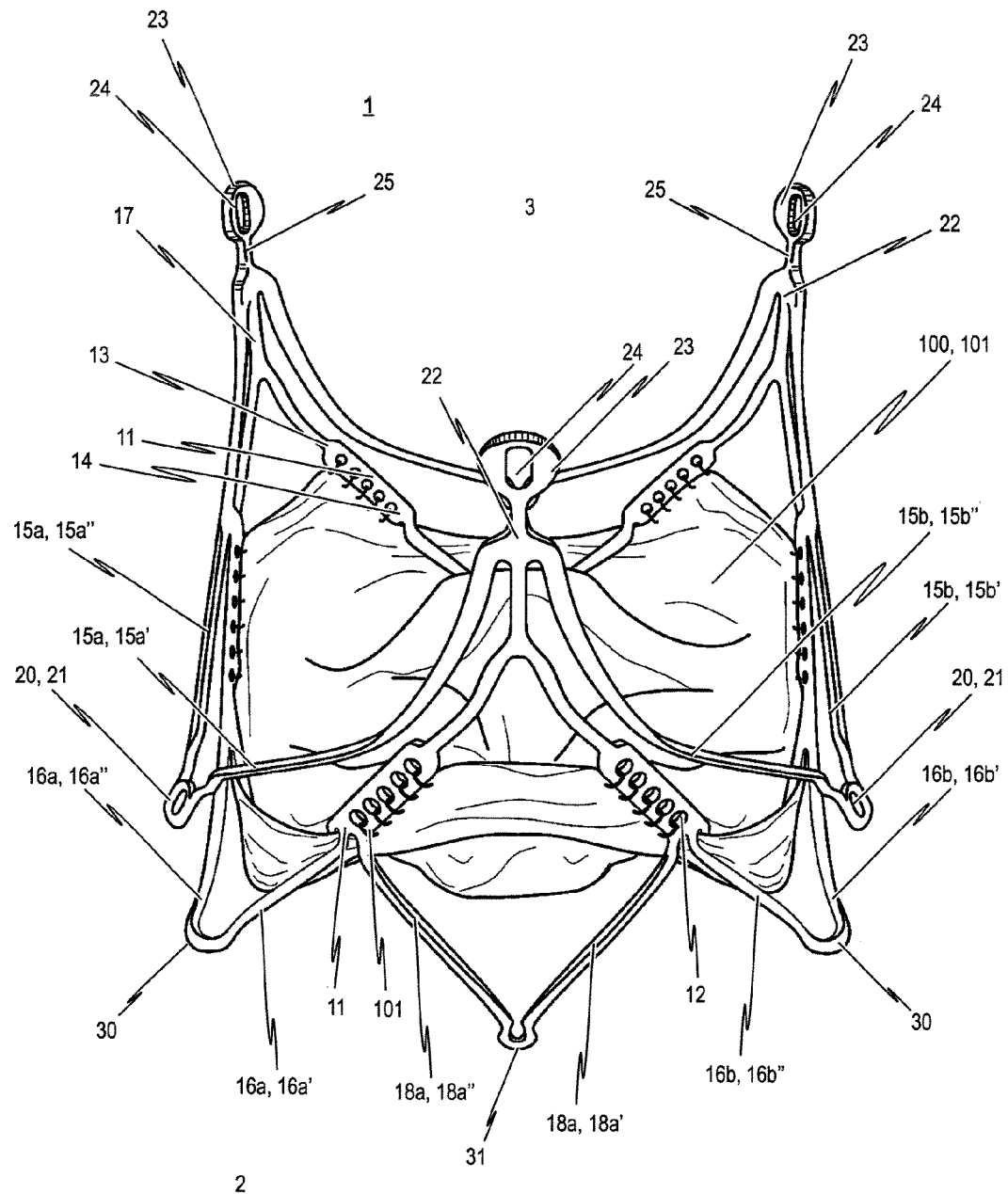
Figure 2E:
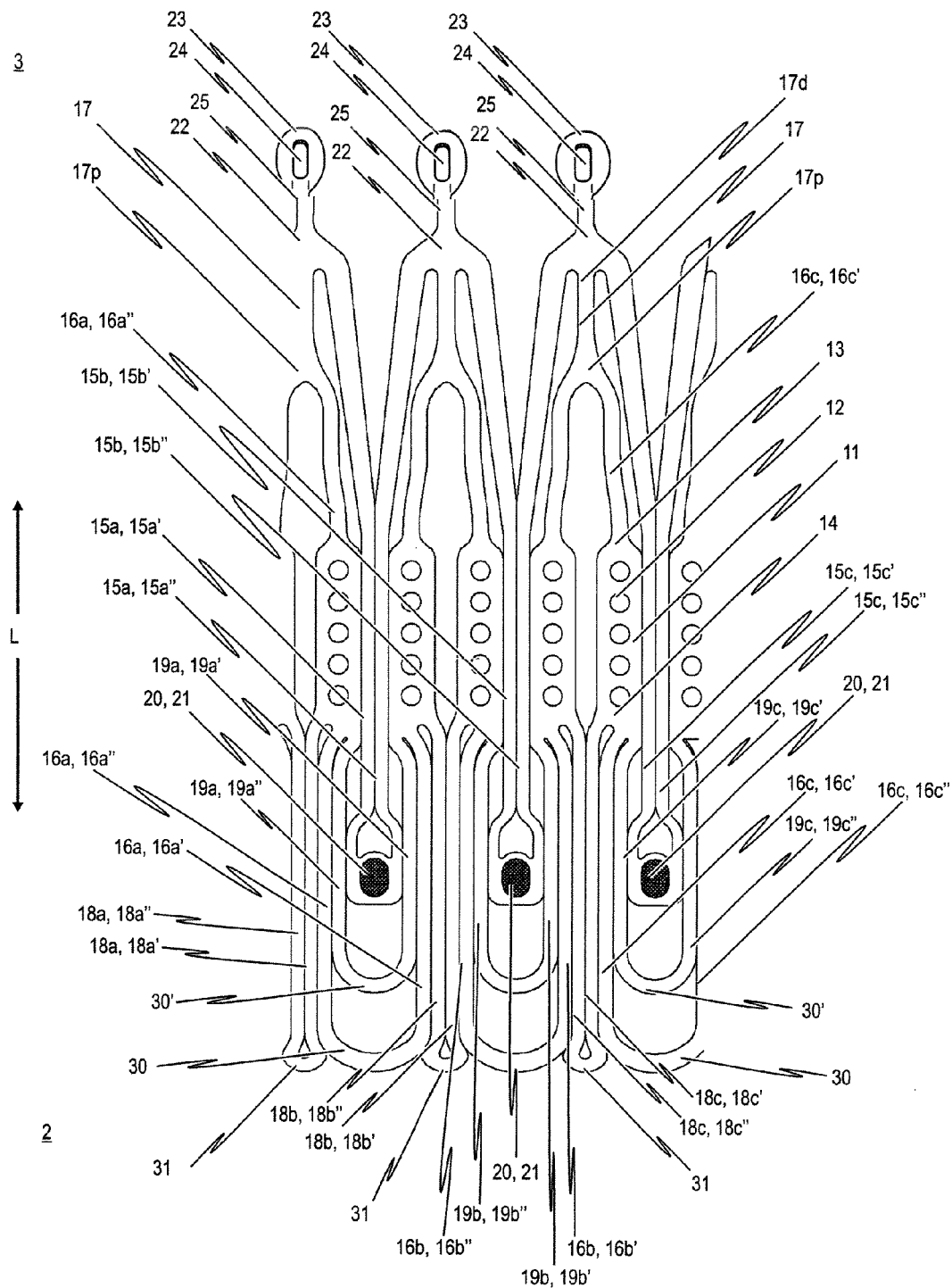
Figure 3:
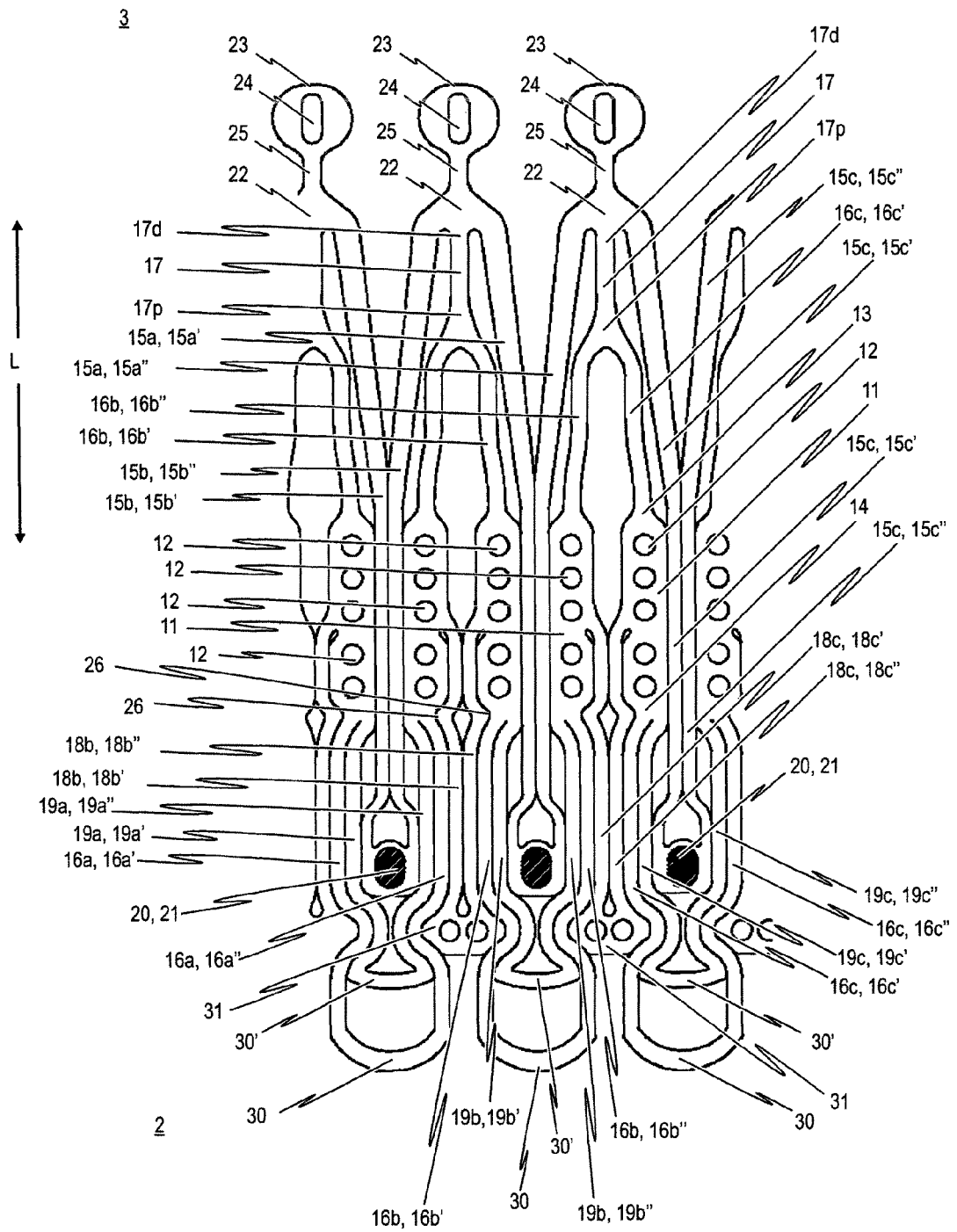
Figure 4:
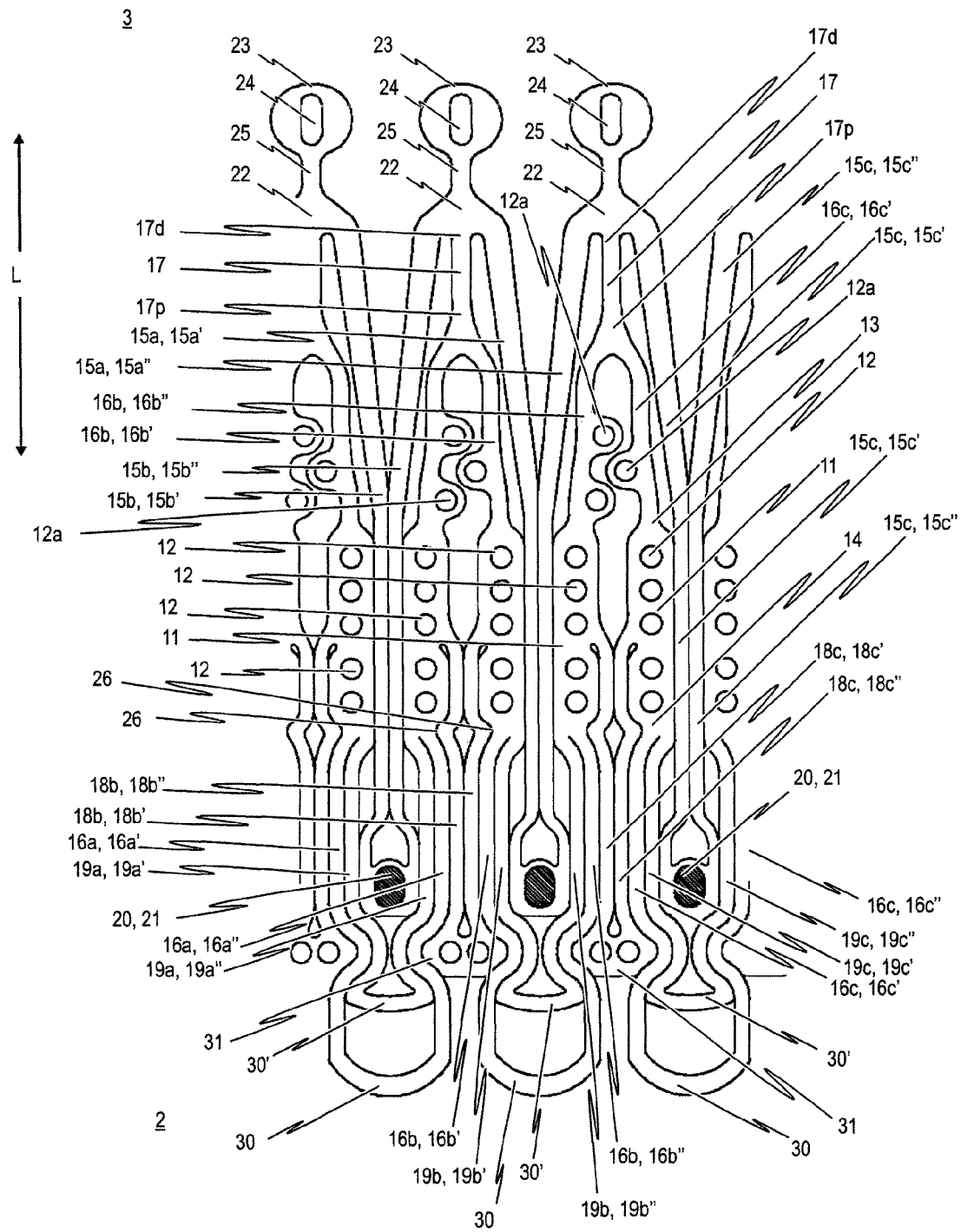
Figure 5A:
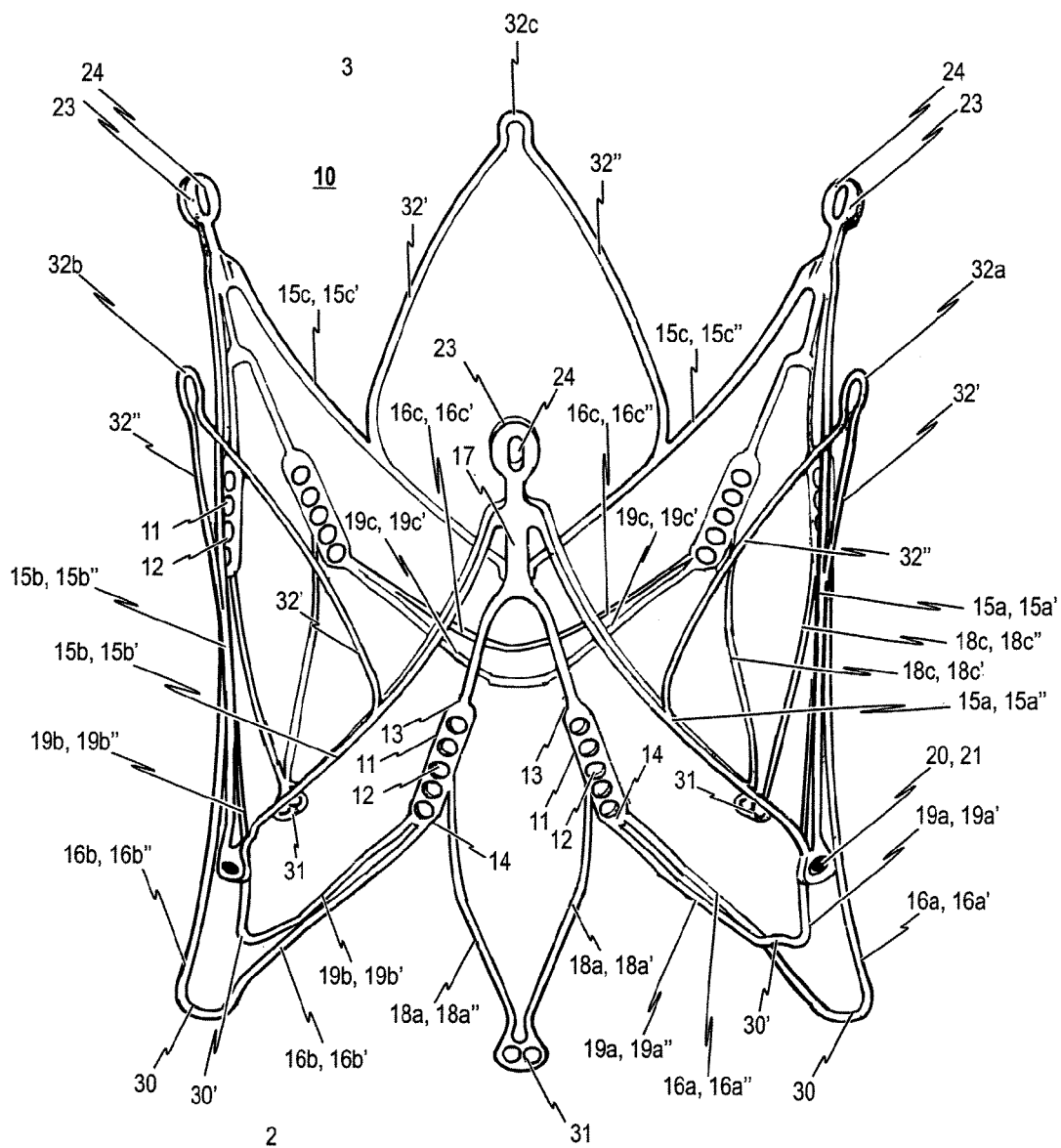
Figure 5B:
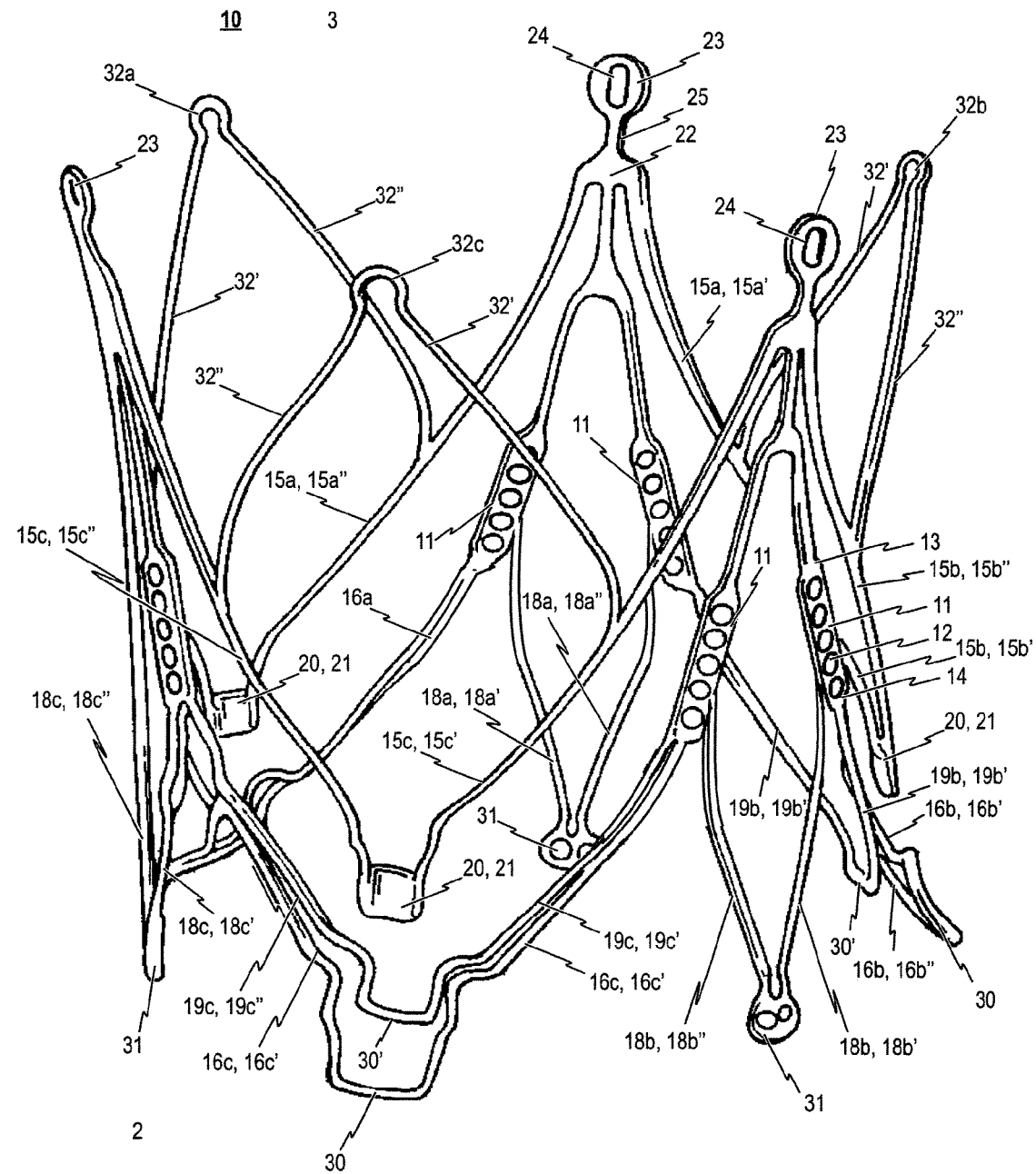
Figure 5C:
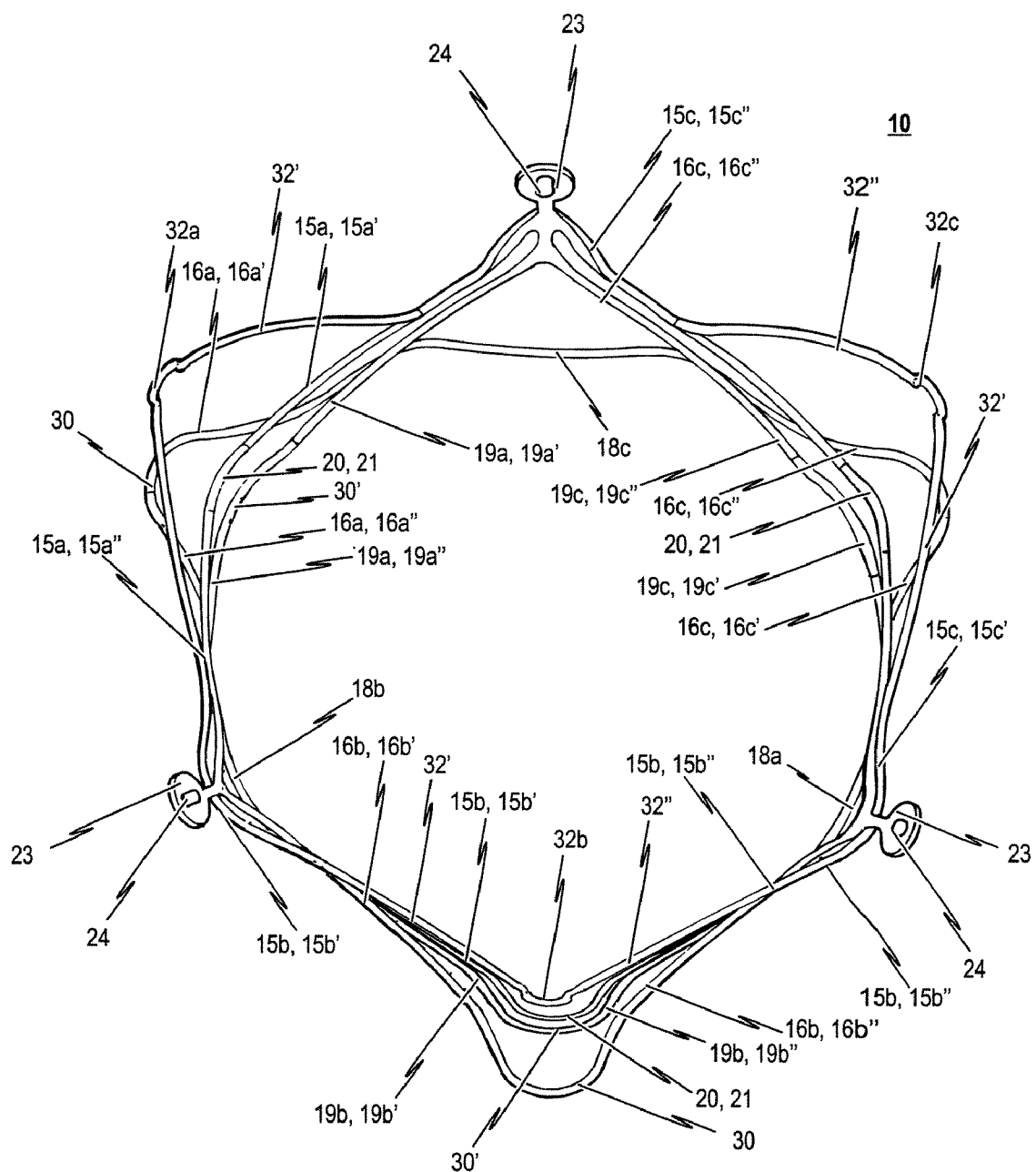
Figure 5D:
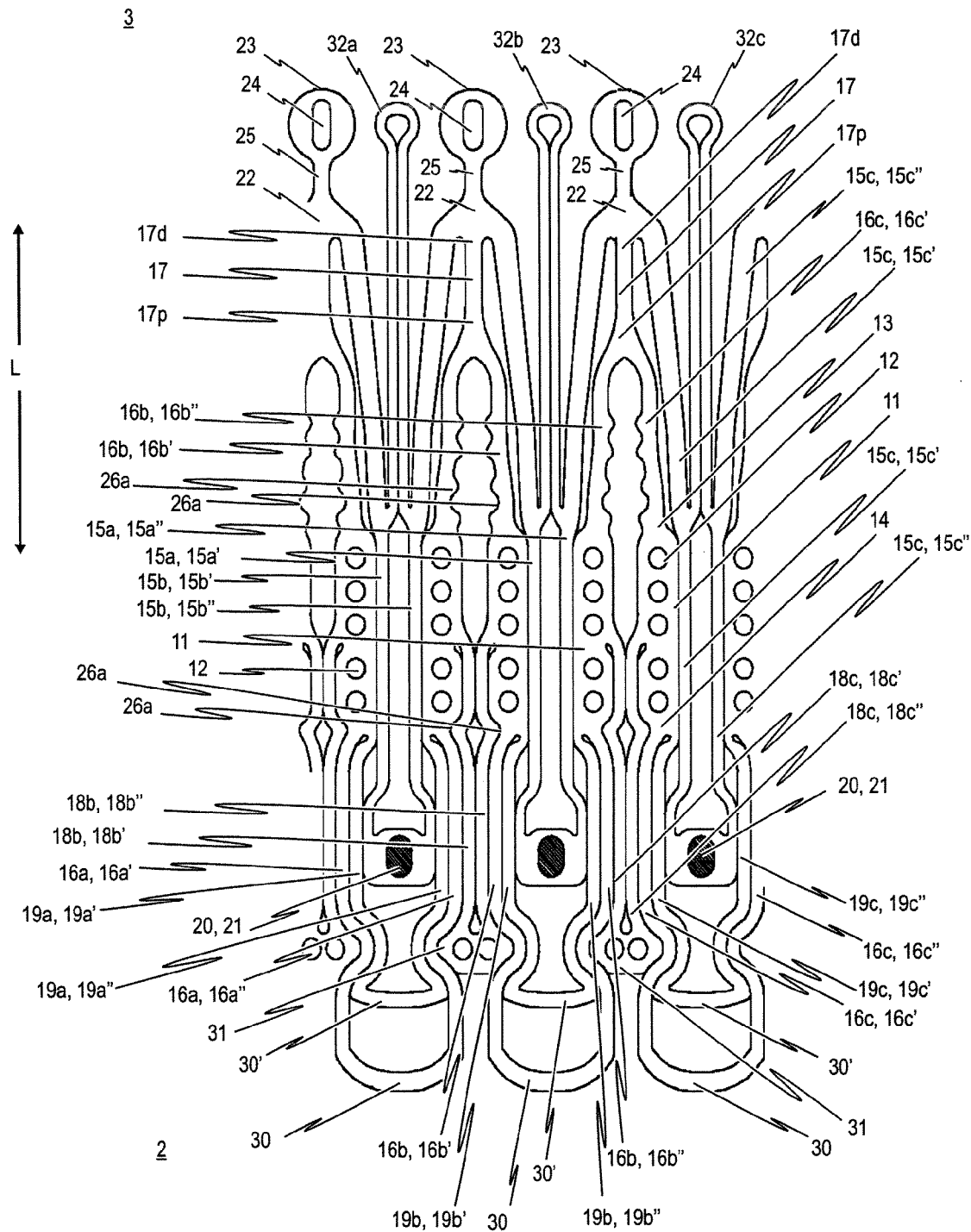

The stent 10 is preferably made from a shape memory material. The state of stent 10 shown in FIG. 1a or FIG. 2a, in which the stent 10 is in its first shape and thus in its collapsed state, is the so-called "temporary" shape of the stent structure made from a shape memory material. When an external stimulus acts on the stent structure according to FIG. 1a or FIG. 2a, the shape memory effect is activated and thus the predefined permanent shape saved during the manufacture of the stent 10 as pursuant, for example, FIG. 1b or FIG. 2b, is restored.

Said external stimulus is preferably a specifiable switching temperature whereby, to activate the shape memory effect and thus regenerate the saved permanent shape of the stent 10, the stent material is warmed to a higher temperature than the switching temperature. By selecting a suitable chemical composition of the material used for stent 10, a specific switching temperature can be predefined. In the preferred embodiment of the inventive solution, the switching temperature ranges from between about 20° C. and the body temperature of the patient.

When implanting the stent 10, it is conceivable for the stent 10 to be cooled during the insertion procedure. Once the stent 10 has been guided to its desired site of implantation, i.e. to the native cardiac valve H (cf. FIG. 12a), preferably using a suitable insertion catheter system, the cooling can be stopped. The stent 10 is then allowed to warm up to the patient's body temperature (36° C.) and the shape memory effect of the stent material is thus activated. Due to the self-expanding property of stent 10 having been triggered, radial forces are generated which act on the individual components of the stent, in particular on the positioning arches 15a, 15b, 15c, the retaining arches 16a, 16b, 16c and the auxiliary arches 18a, 18b, 18c of the stent 10.

The inventive stent 10, as well as the insertion catheter system used to implant the stent, are preferably configured so that the stent 10 with the valvular prosthesis 100 affixed thereto can be introduced transarterially into the body of the patient. In one example, the stent 10 is accommodated in the tip of the catheter of the insertion catheter system, the catheter tip being introduced into the body via, for example, puncture of the A. femoris communis (inguinal artery). A suitable catheter system is described in WO2006/076890 and PCT/EP2008/003803, the details of which are incorporated herein by reference.

Alternatively, the stent 10 according to certain embodiments of the invention is also suited for transapical implantation, in which—coming from the apex of the heart—the catheter tip of the insertion catheter system is advanced to the aortic valve through, for example, the left ventricle. With a catheter tip modified accordingly, an analogous implantation of the stent 10 with the valvular prosthesis 100 is thus possible. A suitable catheter system is described in PCT/EP2008/003803, the details of which are incorporated herein by reference Regardless of whether the stent 10 is delivered to the site of implantation via a transarterial or transapical approach, the tip of the catheter of the insertion catheter system is preferably advanced to the implantation site using angiographic (angiography) and echocardiographic (ultrasound) control. The actual implantation of stent 10 with the attached valvular prosthesis 100 then follows.

FIGS. 12a to 12c schematically show the process sequence to illustrate trans-arterial implantation of an endoprothesis 1 comprising a stent 10 in accordance with certain embodiments of the invention. As shown, the implantation of the stent 10 with the valvular prosthesis 100 attached thereto ensues such that the individual components of the stent 10 accommodated in the catheter tip K are successively released by appropriately manipulating the catheter tip K of an insertion catheter system.

The catheter system used to implant the inventive stent 10 is ideally configured such that a liquid cooling agent can be fed through a hollow interior of the catheter system to catheter tip K. The liquid cooling agent, for example in the form of a saline solution, maintains the stent 10 accommodated in the catheter tip K at a temperature below the switching temperature while the catheter tip K is being advanced to the site of implantation. This is of particular advantage when a shape memory material is provided as the material of the stent 10. This is because the stent 10 transforms from a temporary shape into a permanent shape upon the influence of an external stimulus. The temporary shape is the first shape of stent 10 (in collapsed state, when the stent 10 is accommodated in the catheter tip K of the insertion system) and the "permanent shape" is the second shape of stent 10 (the expanded state of the stent 10 after the stent 10 has been released from the catheter tip K).

It is to be noted that the "permanent shape" of the expanded stent 10 conforms to the native shape of its environment. This allows for variations in the shape of the environment at the site of implantation which will vary from patient to patient. This property of the stent 10, related to the "permanent shape" of the expanded stent 10 automatically adapting completely to the native shape of its environment, will thus always ensure that the valvular prosthesis 100 is optimally implanted.

Because a shape memory material such as nitinol, i.e. an equiatomic alloy of nickel and titanium, can be used for the inventive stent 10, a particularly gentle implantation procedure is achievable when implanting the stent 10 with the valvular prosthesis 100 affixed thereto.

The stent 10 accommodated in the catheter tip K can be cooled by flushing the insertion catheter system with a suitable cooling agent while the catheter tip K is being advanced to keep the temperature of the stent material below the critical transition temperature. Once the catheter tip K with the cooled stent 10 has been advanced to the site of implantation, cooling of the stent 10 should be stopped, as a consequence of which the stent 10 warms up to the body temperature (36° C.) of the patient and the shape memory effect of the stent material is thus activated.

Once the self-expanding property of the individual components of the stent 10 have been activated, radial forces are generated which act on the individual components of stent 10, in particular on the positioning arches 15a, 15b, 15c, the retaining arches 16a, 16b, 16c and the auxiliary arches 18a, 18b, 18c of stent 10. Since the respective components of stent 10 are still situated in the catheter tip K, the radial forces developing upon the critical switching temperature being exceeded and acting on the individual components of the stent 10 are still compensated by the wall of the catheter tip K, so that—despite the activation of the shape memory effect—the stent 10 is forcibly kept in its first (collapsed) shape.

Upon the subsequent manipulation of catheter tip K—by the appropriate incremental release of the stent 10—the individual components of stent 10, are then discharged from the catheter tip K. As FIG. 12a shows, the positioning arches 15a, 15b, 15c of stent 10 spread out radially due to the acting radial forces. The expanded positioning arches 15a, 15b, 15c can then be positioned into the pockets T of the native cardiac valve H.

Thereafter—as depicted in FIG. 12b—the remaining components of stent 10 are sequentially released from the catheter tip K. The released remaining components of stent 10, in particular the auxiliary arches 18a, 18b, 18c and the retaining arches 16a, 16b, 16c with the valvular prosthesis 100, then spread out radially and the valvular prosthesis 100 attached to the fastening portions 11 unfolds like an umbrella.

The radial forces acting on both the retaining arches 16a, 16b, 16c and the auxiliary, arches 18a, 18b, 18c of the stent 10 as well as the radial forces acting on the upper end region 3 of stent 10, result in the stent 10 being pressed radially against the vascular wall (cf. FIG. 12c). This effects a secure anchoring of stent 10 with the expanded valvular prosthesis 100 at the site of implantation on the one hand and, on the other, a reliable seal of the valvular prosthesis 100 at the lower end 2 of stent 10.

The catheter tip K of the insertion catheter system is then manipulated further to release the eyelets 24 of the stent 10, thereby allowing the upper end region 3 of the stent 10 to expand. In so doing, the valve leaflets of the native cardiac valve H are clamped between respective positioning and retaining arches and the valvular prosthesis 100 disposed on the lower end 2 of stent 10 can spread open.

After the successful implantation of the stent 10 and valvular prosthesis 100, the catheter is then removed from the body of the patient.

The stent 10 is not limited to being made from shape memory material which self-expands from its first (collapsed) shape into its second (expanded) shape in response to an external stimulus. Rather, it is also categorically conceivable for the stent 10 to be expanded using a conventional balloon system.

It will be appreciated that the inventive solution is also not limited to the specific embodiments as described with reference to the attached drawings. Rather, the invention encompasses combinations of the individual features exemplified in the embodiments described.

For example, with respect to fixing the upper area 3 of stent 10 to the wall of the blood vessel into which the stent 10 is deployed, it would be conceivable for the stent 10 to comprise barb members arranged, for example, on the eyelets 24, the tips of the barbs pointing toward the lower end 2 of stent 10.

In addition, a liner or sheath, typically a fabric, polymeric or pericardial sheet, membrane, or the like, may be provided over at least a portion of the exterior of the stent 10 to cover all or most of the surface of the outside of the stent 10, extending from a near-proximal location to a near-distal location. The liner may be attached to the stent 10 at least one end, as well as at a plurality of locations between said ends thereby forming an exterior coverage. Such exterior coverage provides a circumferential seal against the inner wall of the blood vessel lumen in order to inhibit leakage of blood flow between the stent 10 and the luminal wall thereby and to prevent a blood flow bypassing the endoprosthesis 1.

For example, the liner may be stitched or otherwise secured to the stent 10 along a plurality of circumferentially spaced-apart axial lines. Such attachment permits the liner to fold along a plurality of axial fold lines when the stent 10 is radially compressed. The liner will further be able to open and conform to the luminal wall of the tubular frame as the frame expands. Alternatively, the liner may heat welded, or ultrasonically welded to the stent 10. In an exemplary embodiment where the stent 10 is provided with a plurality of independent fastening portions 11, 11a, the liner may be secured at these fastening portions 11, 11a. In a second exemplary embodiment where a plurality of independent arches (positioning arches 15a, 15b, 15c, retaining arches 16a, 16b, 16c, auxiliary arches 18a, 18b, 18c and/or fastening arches 19, 19a, 19b, 19c) are provided, the liner is secured to these arches preferably along axial lines. The liner will preferably be circumferentially sealed against the stent 10 at least one end.

By covering at least a part of the outside surface of the stent 10 with the liner or sheath, thrombogenicity of the endoprosthesis 1 resulting from exposed stent elements is greatly reduced or eliminated. Such reduction of thrombogenicity is achieved while maintaining the benefits of having a stent structure which is used for spreading up a valvular prosthesis 100 and for anchoring the valvular prosthesis 100 in place.

As already mentioned, the stent 10 can be compressed from a relaxed, large diameter configuration to a small diameter configuration to facilitate introduction. It is necessary, of course, that the outer liner remain attached to the stent 10 both in its radially compressed configuration and in its expanded, relaxed configuration.

The liner is composed of pericardial material or conventional biological graft materials, such as polyesters, polytetrafluoroethylenes (PTFE's), polyurethanes, and the like, usually being in the form of woven fabrics, non-woven fabrics, polymeric sheets, membranes, and the like. A presently preferred fabric liner material is a plain woven polyester, such as Dacron® yarn (Dupont, Wilmington, Del.).

LIST OF REFERENCE NUMERALS

1 endoprosthesis
2 lower end of the stent/endoprosthesis
3 upper end of the stent/endoprosthesis
10 cardiac valve stent/stent
11 fastening portion of the stent
11a additional fastening portion of the stent
12 fastening holes
12a additional fastening holes
12b auxiliary fastening holes
13 upper end of the fastening portion
14 lower end of the fastening portion
15a-15c positioning arches
15a'-15a" arms of the first positioning arch
15b'-15b" arms of the second positioning arch
15c'-15c" arms of the third positioning arch
16a-16c retaining arches
16a'-16a" arms of the first retaining arch
16b'-16b" arms of the second retaining arch
16c'-16c" arms of the third retaining arch
17 first connecting web
17d upper end of the first connecting web
17p lower end of the first connecting web
18a-18c auxiliary arches
18a'-18a" arms of the first auxiliary arch
18b'-18b" arms of the second auxiliary arch
18c'-18c" arms of the third auxiliary arch
19, 19a-19c fastening arches
19a'-19a" arms of the first fastening arch
19b'-19b" arms of the second fastening arch
19c'-10c" arms of the third fastening arch
20 head portion of the positioning arch
21 reference marker
22 connecting portion between the arms of neighbouring positioning arches
23 catheter retaining means
24 eyelet
25 second connecting web
26 notches
26a additional notches
26b auxiliary notches
27 fixing bridge
30 head portion/connecting portion of the retaining arch
30' head portion/connecting portion of the fastening arch
31 head portion/connecting portion of the auxiliary arch
32a-32c radial arches
33 head/connecting portion of a radial arch
40 annular collar
40' upper annular collar
41 supporting web
42 transversal web
100 valvular prosthesis
101 thread
102 flap segment of the valvular prosthesis
105 annular bead of the valvular prosthesis
H native cardiac valve
K catheter tip of an insertion catheter system
L longitudinal direction of the stent
T pocket of the native cardiac valve
P sleeve-like bead of the valvular prosthesis

What is claimed is:

1. An expandable stent, comprising:
 a plurality of positioning arches, each having an apex projecting toward a proximal end of the stent, the plurality of positioning arches being configured to be positioned within a plurality of pockets of a native heart valve radially outward of a plurality of native heart valve leaflets,
 a plurality of retaining arms, each having a proximal end, the plurality of retaining arms being configured to be positioned radially inward of the plurality of native heart valve leaflets, and
 a first annular collar having a distal end connected to a proximal end of at least one of the plurality of retaining arms and a proximal end defining a proximalmost end of the stent,
 wherein the proximal ends of the plurality of retaining arms are positioned closer to the proximalmost end of the stent than the proximal end of the plurality of positioning arches.

2. The expandable stent according to claim 1, wherein each of the plurality of positioning arches includes a substantially U-shaped or V-shaped structure.

3. The expandable stent according to claim 1, wherein the first annular collar includes a substantially lattice structure.

4. The expandable stent according to claim 1, further including a collapsed mode when being introduced into a patient's body and an expanded mode when implanted.

5. The expandable stent according to claim 1, further including at least one radial arch substantially circumferentially aligned with at least one of the plurality of positioning arches, wherein the at least one radial arch includes first and second arms joined to one another at a radiused head portion.

6. The expandable stent according to claim 5, wherein the at least one radial arch includes a plurality of radial arches.

7. The expandable stent according to claim 1, further including a second annular collar.

8. The expandable stent according to claim 7, wherein the second annular collar is positioned at a distal end of the stent.

9. The expandable stent according to claim 7, wherein the second annular collar includes a substantially lattice structure.

10. An expandable stent, comprising: a plurality of positioning arches configured to be positioned within a plurality of pockets of a native heart valve radially outward of a plurality of leaflets of the native valve, a plurality of retaining arches configured to support a heart valve prosthesis, and a first annular collar having a substantially lattice structure, wherein each retaining arch is associated with a corresponding positioning arch and has a distal end portion axially aligned, along a longitudinal direction of the stent, with and joined to a distal end portion of the corresponding positioning arch, and wherein the heart valve prosthesis is attached to the plurality of retaining arches such that at least part of the prosthetic valve extends from the plurality of retaining arches transversely across an interior of the stent.

11. The expandable stent according to claim 10, further including a collapsed mode when being introduced into a patient's body and an expanded mode when implanted.

12. The expandable stent according to claim 10, wherein the plurality of positioning arches includes only three arches.

13. The expandable stent according to claim 10, further including a second annular collar having a substantially lattice structure, wherein the first annular collar is positioned at a distal end of the stent and the second annular collar is positioned at a proximal end of the stent.

14. An expandable stent comprising:

a plurality of positioning arches configured to be positioned within a plurality of pockets of a native heart valve, each of the plurality of positioning arches having an apex projecting toward a proximal end of the stent;

a plurality of retaining arms configured to support a heart valve prosthesis;

at least one strut member, interspaced between two adjacent positioning arches, the at least one strut member including a first end connected to at least one of the plurality of positioning arches, a second cantilevered end projecting toward the proximal end of the stent, and a plurality of fastening holes configured to receive a suture; and a collar connected to each of the plurality of retaining arms.

15. The expandable stent according to claim 14, wherein the at least one strut member further includes a plurality of notches configured to anchor a suture.

16. The expandable stent according to claim 14, wherein the at least one strut member is a plurality of strut members, each strut member circumferentially interspaced between two adjacent positioning arches.

17. The expandable stent according to claim 14, wherein a valvular prosthesis is connected to the stent via at least one suture guided through at least a portion of the plurality of fastening holes.

18. The expandable stent according to claim 17, wherein the valvular prosthesis is made from pericardium.

19. The expandable stent according to claim 14, further including at least one radial arch interspaced between two adjacent positioning arches.

20. The expandable stent according to claim 14, wherein the collar includes a substantially lattice structure.

* * * * *